US 008268326B2

(12) United States Patent
Paterson et al.

(10) Patent No.: US 8,268,326 B2
(45) Date of Patent: Sep. 18, 2012

(54) COMPOSITIONS COMPRISING HMW-MAA AND FRAGMENTS THEREOF, AND METHODS OF USE THEREOF

(75) Inventors: Yvonne Paterson, Philadelphia, PA (US); Paulo Maciag, Princeton, NJ (US); Matthew Seavey, Prospect Park, PA (US); Soldano Ferrone, Pittsburgh, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 793 days.

(21) Appl. No.: 12/244,828

(22) Filed: Oct. 3, 2008

(65) Prior Publication Data
US 2009/0202587 A1 Aug. 13, 2009

Related U.S. Application Data

(63) Continuation-in-part of application No. 11/889,715, filed on Aug. 15, 2007.

(60) Provisional application No. 60/960,538, filed on Oct. 3, 2007, provisional application No. 60/837,608, filed on Aug. 15, 2006.

(51) Int. Cl.
*A61K 39/02* (2006.01)
*A61K 39/00* (2006.01)
*A61K 39/385* (2006.01)
*A61K 45/00* (2006.01)
*A01N 63/00* (2006.01)
*C12P 21/04* (2006.01)

(52) U.S. Cl. ............... 424/200.1; 424/277.1; 424/184.1; 424/93.2; 424/193.1; 424/278.1; 424/93.4; 435/69.7

(58) Field of Classification Search .................. None
See application file for complete search history.

(56) References Cited

U.S. PATENT DOCUMENTS

| | | |
|---|---|---|
| 4,458,066 A | 7/1984 | Caruthers et al. |
| 4,521,382 A | 6/1985 | Kessick |
| 4,567,041 A | 1/1986 | Likhite |
| 4,777,239 A | 10/1988 | Schoolnik et al. |
| 4,816,253 A | 3/1989 | Likhite et al. |
| 4,879,213 A | 11/1989 | Fox et al. |
| 4,945,050 A | 7/1990 | Sanford et al. |
| 5,262,177 A | 11/1993 | Brown et al. |
| 5,342,774 A | 8/1994 | Boon et al. |
| 5,369,008 A | 11/1994 | Arlinghaus et al. |
| 5,681,570 A | 10/1997 | Yang et al. |
| 5,824,538 A | 10/1998 | Branstrom et al. |
| 5,830,702 A | 11/1998 | Portnoy et al. |
| 5,858,682 A | 1/1999 | Gruenwald et al. |
| 5,876,735 A | 3/1999 | Reed |
| 5,877,159 A | 3/1999 | Powell et al. |
| 6,015,567 A | 1/2000 | Hudziak et al. |
| 6,051,237 A | 4/2000 | Paterson et al. |
| 6,267,690 B1 | 7/2001 | Salmon |
| 6,306,404 B1 | 10/2001 | LaPosta et al. |
| 6,333,169 B1 | 12/2001 | Hudziak et al. |
| 6,479,258 B1 | 11/2002 | Short |
| 6,521,449 B1 | 2/2003 | Polack et al. |
| 6,565,852 B1 | 5/2003 | Paterson |
| 6,767,542 B2 | 7/2004 | Paterson et al. |
| 6,855,320 B2 | 2/2005 | Paterson |
| 7,135,188 B2 | 11/2006 | Paterson |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,700,344 B2 | 4/2010 | Paterson et al. |
| 2003/0028206 A1 | 2/2003 | Shiber |
| 2003/0202985 A1 | 10/2003 | Paterson |
| 2004/0228877 A1 | 11/2004 | Dubensky et al. |
| 2005/0118184 A1 | 6/2005 | Paterson et al. |
| 2005/0129715 A1 | 6/2005 | Paterson et al. |
| 2006/0051380 A1 | 3/2006 | Schulick et al. |
| 2006/0093582 A1 | 5/2006 | Paterson et al. |
| 2006/0121053 A1 | 6/2006 | Sweeney et al. |
| 2006/0205067 A1 | 9/2006 | Paterson et al. |
| 2006/0233835 A1 | 10/2006 | Paterson et al. |
| 2006/0269561 A1 | 11/2006 | Paterson et al. |
| 2007/0253976 A1 | 11/2007 | Paterson et al. |
| 2007/0264279 A1 | 11/2007 | Gravekamp et al. |
| 2008/0124354 A1 | 5/2008 | Paterson et al. |
| 2009/0081248 A1 | 3/2009 | Paterson et al. |
| 2009/0081250 A1 | 3/2009 | Paterson et al. |
| 2009/0202587 A1 | 8/2009 | Paterson et al. |

FOREIGN PATENT DOCUMENTS

| | | |
|---|---|---|
| CA | 2 109 176 | 4/1995 |
| EP | 0 902 086 | 3/1999 |
| JP | 63-173594 | 7/1988 |
| JP | 01-178592 | 7/1989 |
| WO | WO 92/20356 | 11/1992 |
| WO | WO 93/15212 | 8/1993 |
| WO | WO 94/17192 | 8/1994 |

(Continued)

OTHER PUBLICATIONS

Neve et al., Cancer Cell, 2006; 10: 515-527.*
U.S. Appl. No. 08/038,356, filed Mar. 26, 1993, Paterson et al.
U.S. Appl. No. 08/192,857, filed Feb. 7, 1994, Paterson et al.
Lauer et al., "Systematic mutational analysis of the amino-terminal domain of the *Listeria monocytogenes* ActA protein reveals novel functions in actin-based motility" Molecular Microbiology 42(5): 1163-1177, 2001.
Adams et al. (1992) "Cre-lox recombination in *Escherichia coli* cells Mechanistic diffrences from the in vitro reaction" J. Mol. Biol. 226:661-673.
Allison et al. (1997) "Cloning and characterization of a *Prevotella melaninogenica* hemolysin" Infect. Immun. 65(7): 2765-71.

(Continued)

*Primary Examiner* — Vanessa L. Ford
*Assistant Examiner* — Lakia Tongue
(74) *Attorney, Agent, or Firm* — Mark S. Cohen; Pearl Cohen Zedek Latzer, LLP

(57) ABSTRACT

This invention provides recombinant polypeptides comprising a fragment of a High Molecular Weight Melanoma-Associated Antigen (HMW-MAA), recombinant *Listeria* strains comprising same, and methods of inducing an anti-HMW-MAA and anti HER-2/neu immune response thus treating and impeding the growth of tumors, comprising administering same.

7 Claims, 21 Drawing Sheets

FOREIGN PATENT DOCUMENTS

| | | |
|---|---|---|
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 01/27295 | 4/2001 |
| WO | WO 01/72329 | 10/2001 |
| WO | WO 03/092600 | 11/2003 |
| WO | WO 2004/062597 | 7/2004 |
| WO | WO 2004/006837 | 12/2004 |
| WO | WO 2005/037233 | 4/2005 |
| WO | WO 2006/036550 | 4/2006 |
| WO | WO 2006/045750 | 5/2006 |
| WO | WO 2007/061848 | 5/2007 |
| WO | WO 2007/106476 | 9/2007 |
| WO | WO 2007/130455 | 11/2007 |
| WO | WO 2008/079172 | 7/2008 |
| WO | WO 2008/109155 | 9/2008 |
| WO | WO 2008/140812 | 11/2008 |
| WO | WO 2010/008782 | 1/2010 |

OTHER PUBLICATIONS

Anderson (1998) "Human gene therapy" Nature, Apr. 30, 392 (6679 Suppl.): 25-30.
Angelakopoulos et al. (2002) "Safetly and shedding of an attenuated strain of *Listeria monocytogenes* with a deletion of actA/plcB in adult volunteers: a dose escalation study of oral inoculation" Infect. Immun. 70(7):3592-601.
Awwad (1989) "Cyclophosphamide-induced immunologically meditated regression of a cyclophosphamide-resistant murine tumor: a consequence of eliminating precursor L3T4+ suppressor T-cells" Cancer Res. 49(7):1649-1654.
Barry et al. (1992) "Pathogenicity and immunogenicity of *Listeria monocytogenes* small-plaque mutants defective for intracellular growth and cell-to-cell spread" Infection and Immunity 60 (4): 1625-32.
Bast et al. (1975) "Antitumor activity of bacterial infection II effect of *Listeria monocytogenes* on growth of a guinea pig hepatoma" J. Natl. Cancer Inst., 54(3):757-761.
Bear (1986) "Tumor-specific suppressor T-cells which inhibit the in vitro generation of cytolytic T-cells from immune and early tumor-bearing host spleens" Cancer Res. Apr.; 46(4 Pt 1):1805-12.
Beatly, "A dual role for IFN-gamma in resolving the balance between tumor progression and regression" Dissertation Abstracts International, 2000, 61/10B: 5224 Abstract Only.
Bernhard et al. (2002) "Vaccination against the HER-2/neu oncogenic protein" Endocrine-Related Cancer, 9:33-44.
Billington et al. (1997) "The Arcanobacterium (Actinomyces) pyogenes hemolysin, pyolysin, is a novel member of the thiol-activated cytolysin family" J Bacteriol. Oct.; 179(19): 6100-6.
Bodmer et al. (1988) "Enhanced recognition of a modified peptide antigen by cytotoxic T cells specific for influenza nucleoprotein" Cell 52:253-258.
Boyer et al. (2005) "DNA prime *Listeria* boost induces a cellular immune response to SIV antigens in the rhesus macaque model that is capable of limited supperssion of SIV239 viral replication" Virology, Mar. 1; 333(1):88-101.
Brasseur et al. (1992) "Human gene MAGE-1, which codes for a tumor-rejection antigen, is expressed by some breast tumors" Int. J. Cancer 52(5):839-841.
Brockstedt et al., (2004) "*Listeria*-based cancer vaccines that segregate immunogenicity from toxicity" Proc. Natl. Acad. Sci. USA 101(38):13832-7.
Bron et al. (2004) "Identification of *Lactobacillus plantarum* genes that are induced in the gastrointestinal tract of mice" J Bacteriol. Sep.; 186(17):5721-9.
Brown et al. (1988) "Site-specific integration in *Sccharopolyspora erythraea* and multisite integration in *Sterptomyces lividans* of antinomycete plasmid pSE101" J. Bacteriology 170: 2287-2295.
Bruhn et al. (2005) "Characterization of anti-self CD8 T-cell responses stimulated by recombinant *Listeria monocytogenes* expressing the melanoma antigen TRP-2" Vaccine Jul. 21; 23(33):4263-72.

Lin et al. (1996) Treatment of establishment tumors with a novel vaccine that enhances Major Histocompatibility Class II presentation of tumor antigen Cancer Res. 56: 21-26.
Brundage et al. (1993) "Expression and phosphorylation of the *Listeria monocytogenes* ActA protein in mammalian cells" Proc. Natl. Acad. Sci. USA 90:11890-11894.
Bubert et al. (1997) "The *Listeria monocytogenes* iap gene as an indicator gene for the study of PrfA-dependent regulation" Mol. Gen. Genet. Sep.; 256(1):54-62.
Burnham (2003) "Bad bugs: good for cancer therapy?" Drug Discovery Today 8(2):54-55.
Camilli et al. (1993) "Daul roles pf plcA in *Listeria monocytogenes* pathogenesis" Mol. Microbiol. 8:143-157.
Carbone (1989) "Induction of ovalbumin-specific cytotoxic T cells by in vivo peptide immunization" J Exp Med 169:603-612.
Carbone (1990) "Class I-restricted processing and presentation of exogenous cell-associated antigen in vivo" J Exp Med 171:377-387.
Chamberlain et al. (2000) "Innovations and strategies for the development of anticancer vaccines" Expert Opinion on Pharmacotherapy 1(4):603-614.
Courvalin et al. (1995) "Gene transfer from bacteria to mammalian cells" C R Acad Sci III, Dec; 318(12):1207-12.
Cunto-Amesty et al. (2003) "Strategies in cancer vaccines development" Int J Parasitol, 33(5-6):597-613.
Dakappagari et al. (2000) "Prevention of mammary tumors with a chimeric HER-2 B-cell epitope peptide vaccine" Cancer Res. Jul. 15; 60(14):3782-9.
Darji et al. (2003) "Induction of immune responses by attenuated isogenic mutant strains of *Listeria monocytogenes*" Vaccine 1; 21 Suppl 2:S102-9.
Darji et al. (1995) "Hyperexpression of listeriolysin in the nonpathogenic species *Listeria innocua* and high yield purification" J Biotechnol. Dec. 15; 43(3): 205-12.
Darji et al. (1995) "Listeriolysin generates a route for the presentation of exogenous antigens by major histocompatibility complex class I" Eur J Immunol. Oct; 25(10):2967-71.
Darji et al. (1997) "TAP-dependent major histocompatibility complex class I presentation of soluble proteins using listeriolysin" Eur J Immunol. Jun; 27(6): 1353-9.
Dermime et al. (2004) "Vaccine and antibody-directed T cell tumour immunotherapy", Biochim. Biophys. Acta. 1704(1):11-35.
Deshpande et al. (1997) "Isolation of a contact-dependent haemolysin from *Mycobacterium tuberculosis*" J. Med. Microbiol. Mar; 46(3):233-8.
Dietrich et al. (1998) "Delivery of antigen-encoding plasmid DNA into the cytosol of macrophages by attenuated suicide *Listeria monocytogenes*" Nature Biotechnology 15:181-185.
Dietrich et al. (2001) "From evil to good: a cytolysin in vaccine development" Trends Microbiol. Jan; 9(1):23-8.
Dramsi et al. (1995) "Entry of *Listeria monocytogenes* into hepatocytes requires expression of inIB, a surface protein of the internalin multigene family" Mol Microbiol 16(2):251-61.
Dunn et al. (1991) "Selective radiation resistance of immunologically induced T cells as the basis for irradiation-induced T-cell-mediated regression of immunogenic tumor" J Leukoc Biol. 49(4):388-396.
Ebert et al. (1990) "Selective immunosuppressive action of a factor produced by colon cancer cells" Cancer Res. 50(19):6158-6161.
Ezzel (1995) "Cancer Vaccines: An Idea Whose Time Has Come?" J NIH Res., 7:46-49.
Frankel et al. (1995) "Induction of cell-mediated immune responses to human immunodeficiency virus type 1 Gag protein by using *Listeria monocytogenes* as a live vaccine vector" J. Immunol. 155:4775-4782.
Friedman et al. (2000) "Induction of human immunodeficiency virus (HIV)-specific CD8 T-cell responses by *Listeria monocytogenes* and a hyperattenuated *Listeria* strain engineered to express HIV antigens" J. Virology 74 9987-9993.
Fuji (1987) "Significance of suppressor macrophages for immunosurveillance of tumor-bearing mice" J Natl Cancer Inst 78(3):509-517.

Furukawa (1993) "Nude mouse metastatic models of human stomach cancer constructed using orthotopic implantation of histologically intact tissue" Cancer Res. 53(5):1204-1208.

Galen et al. (2001) "Can a 'flawless' live vector vaccine strain be engineered?" Trends Microbiol. 9(8):372-6.

Gentschev et al. (1996) "Development of antigen-delivery systems, based on the *Escherichia coli* hemolysin secreatiohn pathway" Gene 179:133-140.

Gilmore et al. (1989) "A *Bacilius cereus* cytolytic determinant, cereolysin AB, which comprieses the phospholipase C and sphingomyelinase genes: nucleotide sequence and genetic linkage" J Bacteriol. Feb; 171(2): 744-53.

Glomski et al. (2002) "The *Listeria monocytogenes* hemolysin has an acidic pH optimum to compartmentalize activity and prevent damage to infected host cells" J Cell Biol. Mar. 18; 156(6):1029-38.

Goebel et al. (1993) "*Listeria monocytogenes*—a model system for studying the pathomechanisms of an intracellular microorganism" Zbl. Bakt. 278:334-347.

Goossens et al. (1992) "Induction of protective CD8+ T lymphocytes by an attenuated *Listeria monocytogenes* actA mutant" Int Immunol. Dec; 4(12):1413-8.

Gossens et al. (1995) "Attenuated *Listeria monocytogenes* as a live vector for induction of CD8+ T cells in vivo: a study with the nucleoprotein of the lymphocytic choriomeningitis virus" Int Immunol. May; 7(5):797-805.

Gregory et al. (1997) "Internalin B promotes the replication of *Listeria monocytogenes* in mouse hepatocytes" Infect. Immun. 65(12):5137-41.

Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16" J Immunol. 167(11) 6471-6479.

Gunn et al. (2002) "Recombinant Intra-cellular Bacteria as Carries for Tumor Antigens" in Vaccine Delivery Strategies, Chapter 14, Eds. Guido Dietrich and Werner Goebel, Horizon Scientific Press, UK.

Gunn, "Recombinant *Listeria monocytogenes* as a tumor therapeutic" Dissertation Abstracts International, 2001, 62/5B:2244 Abstract Only.

Gunn et al. (2001) "Listeriolysin—a useful cytolysin" Trends Microbiol. 9(4):161-162.

Harty et al. (1996) "Primary and secondary immune responses to *Listeria monocytogenes*" Curr. Opin. Immunol. 8:526-530.

Hassan et al. (2004) "Mesothelin: a new target for immunotherapy" Clin. Cancer Res. 10 (12 Pt 1):3937-42.

Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation" Proc. Natl. Acad. Sci. USA Aug. 19; 94(17):9394-9.

Hess et al. (1995) "*Listeria monocytogenes* p60 supports host cell invasion by and in vivo survival of attenuated *Salmonella typhimurium*" Infect. Immun. May; 63(5):2047-53.

Hess et al. (1996) "*Salmonella typhimurium* aroA-infection in gene-targeted immunodeficient mice: major role of CD4+ TCR-alpha beta cells and IFN-gamma in bacterial clearance independent of intracellular location" J Immunol. May 1; 156(9):3321-6.

Hess et al. (1996) "Superior efficacy of secreted over somatic antigen display in recombinant *Salmonella* vaccine induced protection against listeriosis" Proc. Nat. Acad. Sci. 93:1458-1463.

Hess et al. (1997) "Protection against murine listeriosis by an attenuated recombinant *Salmonella typhimurium* vaccine strain that secretes the naturally somatic antigen superoxide dismutase" Infect. Immun. Apr.; 65(4):1286-92.

Hess et al. (1998) "*Mycobacterium bovis* bacilli Calmette-Guerin strains secreting listeriolysin of *Listeria monocytogenes*" Proc. Natl. Acad. Sci. 95:5299-5304.

Higgins et al. (1998) "Bacterial delivery of DNA evolves" Nat. Biotechnol. Feb; 16(2):138-9.

Hodgson (2000) "Generalized transduction of serotype 1/2 and Serotype 4b strains of *Listeria monocytogenes*" Mol. Microbiol. 35(2):312-23.

Hu et al. (2004) "*Escherichia coli* expressing recombinant antigen and listeriolysin O stimulate class I-restricted CD8+ T cells following uptake by human APC" J. Immunology 172:1595- 1601.

Huang et al. (1994) "Role of bone marrow-derived cells in presenting MHC class I-restricted tumor antigens" Sceince 264 961-965.

Jensen (1997) "Recombinant *Listeria monocytogenes* vaccination eliminates papillomavirus-induced tumors and prevents papiloma formation from viral DNA" J Virol. 71(11):8467-8474.

Jones et al. (1994) "Charcterization of *Listeria monocytogenes* pathogeneis in a strain expressing perfringolysin O in place of listeriolysin O" Infect. Immun. 62:5608-5613.

Kovacsovics-Bankowski et al. (1993) "Efficient major histocompatibility complex class I presentation of exogenous antigen upon phagocytosis by macrophages" Proc. Natl. Acad. Sci. USA 90:4942-4946.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site" J. Virology 75(20):9654-9664.

Lampson et al. (1993) "Exploiting the lacZ reporter gene for quantitative analysis of disseminated tumor growth within the brain: use of the lacZ gene product as a tumor antigen, for evaluation of antigen modulation, and to facilitate image analysis of tumor growth in situ" Cancer Research 53:176-182.

Lara-Tejero et al. (2004) "T cell responses to *Listeria monocytogenes*" Curr. Opin. Microbiol. 7(1):45-50.

Lauer et al. (2002) "Construction, characterization, and use of two *Listeria monocytogenes* site-specific phage integration vectors" J. Bacteriology 184:4177-4186.

Lauer et al. "Characterization of the Attachment Site of Bacteriophage U153 within the *Listeria monocytogenes* comK Gene" ASM Meeting, Abstract 1999.

Leaco et al. (1995) "A species-specific nucleotide sequence of *Mycobacterium tuberculosis* encodes a protein that exhibits hemolytic activity when expressed in *Escherichia coli*" Infect. Immun. Nov.; 63(11):4301-6.

Lee et al. (1991) "Construction of single-copy integration vectors for *Staphylococcus aureus*" Gene 103:101-5.

Lehner et al. (1996) "Processing and delivery of peptides presented by MHC class I molecules" Curr. Opin. Immunol. 8(1):59-67.

Lejeune (1994) "Nitric oxide involvement in tumor-induced immunosuppression" J Immunol. 152(10):5077-5083.

Liau et al. (2002) "Tumor immunity within the central nervous system stimulated by recombinant *Listeria monocytogenes* vaccination" Cancer Res. 62(8):2287-93.

Lin et al. (2002) "Oral vaccination with recombinant *Listeria monocytogenes* expressing human papillomavirus type 16 E7 can cause tumor growth in mice to regress" Int. J. Cancer Dec. 20; 102(6):629-37.

Lingnau et al. (1995) "Expression of the *Literia monocytogenes* EGD inlA and inlB genes, whose products mediate bacterial entry into tissue culture cell lines, by PrfA-dependent and independent mechanisms" Infect. Immun. Oct.; 63(10):3896-903.

Loeffler et al. (2006) "Comparison of different live vaccine strategies in vivo for delivery of protein antigen or antigen-encoding DNA and mRNA by virulence-attenuated *Listeria monocytogenes*" Infect. Immun. Jul; 74(7):3946-57.

Loessner et al. (1995) "Heterogeneous endolysins in *Listeria monocytogenes* bacteriophages: a new class of enzymes and evidence for conserved holin genes within the siphoviral lysis cassettes" Mol. Microbiol. Jun; 16(6):1231-41.

Loessner et al. (2000) "Complete nucleotide sequence, molecular analysis and genome structure of bacteriophage A118 of *Listeria monocytogenes*: implications for phage evolution" Molecular Microbiology 35(2):324-40.

Mandal et al. (2002) "Listeriolysin O-liposome-mediated cytosolic delivery of macromolecule antigen in vivo: enhancement of antigen-specific cytotoxic T lymphocyte frequency, activity, and tumor protection" BBA 1563 7-17.

Manjili et al. (2003) "HSP110-HER2/neu chaperone complex vaccine induces protective immunity against spontaneous mammary tumors in HER-2/neu transgenic mice" J. Immunol. Oct. 15; 171(8):4054-61.

Marquis et al. (1997) "Proteolytic pathways of activation and degradation of a bacterial phospholipase C during intracellular infection by *Listeria monocytogenes*" J. Cell Biol. 137:1381-1392.

Marx et al. (2002) "Broad-host-range cre-lox system for antibiotic marker recycling in gram-negative bacteria" Biotechniques Nov; 33(5):1062-7.

Mclaughlan et al. (1998) "Molecular characterization of an autolytic amidase of *Listeria monocytogenes* EGD" Microbiology May; 144(Pt 5):1359-67.

Mlynarova et al. (2002) "The promiscuity of heterospecific lox sites increases dramatically in the presence of palindromic DNA" Gene Aug. 21; 296(1-2):129-37.

Mollet et al. (1993) "Directed genomic integration, gene replacement, and integrative gene expression in *Streptococcus thermophilus*" J. Bacteriology 175:4315-4324.

Ochsenbein et al. (1999) "A comparison of T cell memory against the same antigen induced by virus versus intracellular bacteria" Proc. Natl. Acad. Sci. USA Aug. 3; 96(16): 9293-8.

Oscarsson et al. (1996) "Induction of haemolytic activity in *Escherichia coli* by the slyA gene product" Mol. Microbiol. Apr; 20(1):191-9.

Palmeros et al. (2000) "A family of removable cassettes designed to obtain antibiotic-resistance-free genomic modifications of *Escherichia coli* and other bacteria" Gene. Apr. 18; 247(1-2):255-64.

Pan (1999) "Regression of established B16F10 melanoma with a recombinant *Listeria monocytogenes* vaccine" Cancer Res. 59(20):5264-5269.

Pan et al. (1995) "A recombinant *Listeria monocytogenes* vaccine expressing a model tumor antigen protects mice against lethal tumor cell challenge and causes regression of established tumours" Nature Med. 1:471-477.

Peng et al. (2004) "The ability of two *Listeria monocytogenes* vaccines targeting human papillomavirus-16 E7 to induce an antitumor response correlates with myeloid dendritic cell function" J. Immunol. 172:6030-6038.

Penichet et al. (2001) "Antibody-cytokine fusion proteins for the therapy of cancer" J. Immunological Methods 248:91-101.

Pfeifer et al. (1993) "Phagocytic processing of bacterial antigens for class I MHC presention to T cells" Nature Jan. 28; 361(6410):359-62.

Pupa et al. (2001) "Prevention of spontaneous neu-expressing mammary taumor development in mice transgenic for rat proto-neu by DNA vaccination" Gene Ther. Jan.; 8(1):75-9.

Quenee et al. (2005) "Combined sacB-based negtive selection and cre-lox antibiotic marker recycling for efficent gene deletion in *Pseudomonas aeruginosa*" Biotechniques Jan.; 38(1):63-7.

Radford et al. (2002) "A recombinant *E. coli* vaccine to promote MHC class I-dependent antigen presentation: application to cancer immunotherapy" Gene Therapy 9:1455-1463.

Radford et al. (2003) "Recombinant *E. coli* efficiently delivers antigen and maturation signals to human dendritic cells: presentation of $MART_1$ to $CD8_+$ T cells" Int. J. Cancer 105:811-819.

Raveneau et al. (1992) "Reduced virulence of a *Listeria monocytogenes* phospholipase-deficient mutant obtained by transposon insertion into the zinc metalloprotease gene" Infect. Immun. 60:916-921.

Reiter et al. (1989) "Transfer RNA genes frequently serve as integration sites for prokaryotic genetic elements" Nucleic Acids Research 17(5) 1907-14.

Renard et al. (2003) "HER-2 DNA and protein vaccine containing potent Th cell epitopes induce distinct protective and therapeutic antitumor responses in HER-2 transgenic mice" J. Immunol. 171(3):1588-95.

Repique (1992) "Immunosuppression derived from human B-lymphoblastoid and melanoma cell lines" Cancer Invest. 10(3):201-208.

Roden et al. (2004) "Vaccination to prevent and treat cervical cancer" Hum. Pathol 35(8):971-82.

Russmann et al. (1998) "Delivery of epitopes by the *Salmonella* type III secretion system for vaccine development" Science Jul. 24; 281(5376):565-8.

Schafer et al. (1992) "Induction of a cellular immune response to a foreign antigen by a recombinant *Listeria monocytogenes* vaccine" J. Immunol. 149(1):53-59.

Scheirlinck et al. (1989) "Integration and expression of alpha-amylase and endoglucanase genes in the *Lactobacillus plantarum* chromosome" Appl. Environ. Microbiol. 55(9):2130-7.

Schmidt et al. (1995) "Molecular Analysis of the Plasmid-Encoded Hemolysin of *Escherichia coli* O157:H7 Strain EDL 933" infection and Immunity, 63(3):1055-1061.

Scortti et al. (2007) "The PrfA virulence regulon" Microbes Infect. Aug; 9(10):1196-207.

Sewell et al. (2004) "Recombinant *Listeria* vaccines containing PEST sequences are potent immune adjuvants for the tumor-associated antigen human papillomavirus-16 E7" Cancer Res. Dec. 15; 64(24):8821-5.

Shen et al. (1998) "Compartmentalization of bacterial antigens: differential effects on priming of CD8 T cells and protective immunity" Cell Feb. 20; 92(4):535-45.

Shetron-Rama et al. (2002) "Intracellular induction of *Listeria monocytogenes* actA expression" Infect. Immun. 70:1087-1096.

Shimizu et al. (1994) "Effects of CD4+ and CD8+ T cells in tumor-bearing mice on antibody production" Cancer Immunol Immunother. 38(4):272-276.

Singh et al. (2005) "Fusion to Listeriolysin O and delivery by *Listeria monocytogenes* enhances the immunogenicity of HER-2/neu and reveals subdominant epitopes in the FVB/N mouse" J. Immunol. Sep. 15; 175(6):3663-73.

Slifka et al. (1996) "Antiviral cytotoxic T-cell memory by vaccination with recombinant *Listeria monocytogenes*" J. Virol. 70(5):2902-10.

Souders et al. (2006) "In vivo bactofection: listeria can function as a DNA-cancer vaccine" DNA Cell Biol. Mar; 25(3):142-51.

Stahl et al. (1984) "Replacement of the *Bacilius subtilis* subtilisin structural gene with an in vitro-derived deletion mutation" J. Bacteriol 158:411-418.

Starks et al. (2004) "*Listeria monocytogenes* as a vaccine vector: virulence attenuation or existing antivector immunity does not diminish therapeutic efficacy" J. Immunology 173:420-427.

Stitz et al. (1990) "Characterization and Immunological properties of influenza A virus nucleoprotein (NP): cell-associated NP isolated from infected cells or viral NP expressed by vaccinia recombinant virus do not confer protection" J Gen Virol. 71(Pt 5):1 169-1179.

Strugnell et al. (1990) "Stable expression of foreign antigens from the cheomosome of *Salmonella typhimurium* vaccine strains" Gene 88:57-63.

Sun et al. (1990) "Isolation of *Listeria monocytogenes* small-plaque mutants defective for intracellular growth and cell-to-cell soread" Infect. Immun. 58 3770-3778.

Tilney et al. (1989) "Actin filaments and growth, movement and spread of the intracellular bacterial parasite, *Listeria monocytogenes*" J Cell Biol. Oct; 109(4 Pt 1):1597-608.

Vasil et al. (1982) "Cloning of a phosphate-regulated hemolysin gene (phospholipase C) from *Pseudomonas aeruginosa*" J. Bacteriol. Oct.; 152(1):431-40.

Vazquez-Boland et al. (1992) "Nucleotide sequence of the lecithinase operon of *Listeria monocytogenes* and possible role of lecithinase in cell-to-cell spread" Infect. lrnmun. 60:219-230.

Verch et al. (2004) "*Listeria monocytogenes*-based antibiotic resistance gene-free antigen delivery system applicable to other vectors and DNA vaccines" Infect. Immun. Nov.; 72(11):6418-25.

Walker et al. (1994) "Tumor growth alters T cell and macrophage production of and responsiveness to granulocyte-macrophage colony-stimulating factor: partial dysregulation through interleukin-10" Cell. Immunol. 154(1):342-357.

Watson et al. (1991) "Splenic macrophages from tumor-bearing mice co-expressing MAC-1 and MAC-2 antigens exert immunoregulatory functions via two distinct mechanisms" J Leukoc Biol 49(2):126-138.

Wei et al. (2005) "*Listeria monocytogenes* phosphatidylinositol-specific phospholipase C has evolved for virulence by greatly reduced activity on GPI anchors" Proc. Natl. Acad. Sci. USA 102:12927-12931.

Weidt et al. (1994) "CD8+ T lymphocyte-mediated antiviral immunity in mice as a result of injection of recombinant viral proteins" J Immunol. Sep. 15; 153(6):2554-61.

Wirth et al. (1986) "Highly efficient protoplast transformation system for *Streptocococus facecalis* and a new *Escherichia coli-S faecalis* suttle vector" J. Bacteriol. 165(3):831-6.

Young et al. (1992) "Tumor-derived cytokines induce bone marrow suppressor cells that mediate immunosuppression through transforming growth factor beta" Cancer Immunol Immunother 35(1):14-18.

Young et al. (1995) "Holins:form and function in bacteriophage lysis" FEMS Microbiol Rev Aug; 17(1-2):191-205.

Zhang et al. (1993) "Functional replacement of the hemolysin a transport signal by a different primary sequence" Proc Natl Acad Sci USA May 1; 90(9):4211-5.

Mengaud, et al (1988) "Expression in *Escherichia Coli* and Sequence Analysis of the Listeriolysin O Determinant of *Listeria monocytogens*." Infection and Immunity, vol. 56, No. 4, 766-772.

Attwood, et al. (2000) "The Babel of Bioinformatics" Science, vol. 290, No. 5491, 471-473.

Bourquin, et al (2000) "Myelin oligodendrocyte glycoprotein-DNA vaccination induces antibody-mediated autoaggression in experimental autoimmune encephalomyelitis." Eur J Immunol 30: 3663-3671.

Darji, et al (1997) "Oral Somatic Transgene Vaccination Using Attenuated *S. Typhimuurium*." vol. 91, 765-775.

Decatur, et al (2000) "A PEST-like sequence in listeriolysin O essential for *Listeria monocytogenes* pathogenicity." Science, vol. 290, No. 5493, pp. 992-995.

Finn, et al (2003) "Cancer vaccines: between the idea and the reality." Nature Reviews Immunology, 3: 630-641.

Guzman, et al (1998) "Attenuated *Listeria monocytogenes* carrier strains can deliver an HIV-1 gp120 T helper epitope to MHC class II-restricted human CD4+ T cells." European Journal of Immunology 28: 1807-1814.

Ikonomidis, et al (1994) "Delivery of a viral antigen to the class I processing and presentation oathway by *Listeria monocytogenes*." Journal of Experimental Medicine, vol. 180, No. 6, pp. 2209-2218.

Kerksiek (1999) "T cell responses to bacterial infection." Curr Opin. Immunol., vol. 1, No. 4, pp. 400-405.

Lasa, et al (1997) "Identification of two regions in the N-terminal domain of ActA involved in the actin comet tail formation by *Listeria monocytogenes*." EMBO 16(7): 1531-40.

Lebrun, et al (1996) "Internalin must be on the bacterial surface to mediate entry of *Listeria monocytogenes* into epithelial cells." Molecular Microbiology 21(3): 579-592.

An et al (1996) "A recombinant minigene vaccine containing a nonameric cytoxic-T-Lymphocyte epitope confers limited protection against *Listeria monocytogenes* infection." Infect. Immun, vol. 64, No. 5, pp. 1685-1693.

Bielecki et al (1990) "*Bacillus subtilis* expressing a haemolysin gene from *Listeria monocytogenes* can grow in mammalian cells" Nature, vol. 354, pp. 175-176.

Gentschev et al (1995) "*Salmonella* Strain Secreting Active Listeriolysin Changes Its Intracellular Localization" Infect. Immun., vol. 63: 4202-4205.

Kaufman, et al. (1999) "Impact of intracellular location of and antigen display by intracellular bacteria: implications for vaccine development", J Immunol. Lett, 65 (1-2):81-84.

Kocks et al. (1992) "*L. monocytogenes*-induced actin assembly requires the actA gene product." Cell, vol. 68, No. 3, pp. 521-531.

Lin, et al (1996) "Treatment of Established Tumors with a Novel Vaccine That Enhances Major Histocompatibility Class II Presentation of Tumor Antigen" Cancer Res. 1996 56:21-56: 21-26.

Moriishi et al., "Sequence analysis of the actA gene of *Listeria monocytogenes* isolated from human." Microbiol. Immunol., vol. 42, No. 2, ages 129-132, 1998.

Paglia, et al (1997) "The defined attenuated *Listeria monocytogenes* delta mp12 mutant is an effective oral vaccine carrier to trigger a long-lasting immune response against a mouse fibrosarcoma." Eur J Immunol 27: 1570-1575.

Pan, et al (1995) "Regression of established tumors in mice mediated by the oral administration of a recombinant *Listeria monocytogenes* vaccine." Cancer Research 55: 4776-4779.

Paul, et al (1989) Fundamental Immunology, 987-988.

Rechsteiner, et al (1996) "PEST sequences and regulation by proteolysis." TIBS 21: 267-271.

Shen, H. et al. (Apr. 25, 1995). "Recombinant *Listeria monocytogenes* as a Live Vaccine Vehicle for the Induction of Protective Anti-Viral Cell-Mediated Immunity," Proc. Natl. Acad Sci. USA 92: 3987-3991.

Realini et al (1994)"Proposed roles in protein-protein association and presentation of peptides by MHC class I receptors." FEBS Letters 348: 109-113.

Ngo, et al. (1994) The Protein Folding Problem and Tertiary Structure Prediction 492-495.

Safley, et al. (1991) "Role of Listeriolysin-o (LLO) in the T Lymphocyte response to infection with *Listeria monocytogenes*" J Immunol. 146(10):3604-3616.

Shen, et al. .(1998) "*Listeria monocytogenes* as a probe to study cell-mediated immunity" Curr. Opin. Immunol. 10(4):450-458.

Skolnick, et al. (2000) "From genes to protein structure and function: novel applications of computational approached in the genomic era" *Trends in Biotech*. 18(1):34-39.

Ward et al., "Construction and characterization of a series of multi-copy promoter-probe plasmid vectors for Streptomyces using the aminoglycoside phsophotransferase gene from Tn5 as indicator", 1986, Mol. Gen. Genet. 203:468-478.

Jensen et al. (1997) "Recombinant *Listeria monocytogenes* as a live vaccine vehicle and a probe for studying cell-mediated immunity" Immunological Review 158:147-157.

Stryer et al., "Levels of structure in protein architecture", (1998) Biochemistry, Third Edition, WH Freeman Company, New York, 31-33.

Naz NK et al, "Novel human prostate specific cDNA: molecular cloning, expression, and immunobiology of the recombinant protein", Biochem Biophys Res Commun. 297:1075-84, 2002.

Sirard et al (1997) "Intracytoplasmic delivery of Lidteriolysin 0 by a vaccinal strain of *Bacillus anthracis* induces CD8-mediated protection against *Listeria monocytogenes*." J Immun., vol. 159, pp. 4435-4443.

Tanabe et al.(1999) "Induction of Protective T Cells against *Listeria monocytogenes* in Mice by Immunization with a Listeriolysin O-Negative Avirulent Strain of Bacteria and Liposome-Encapsulated Listeriolysin O" Infect. Immun. 67(2):568-575.

Verma et al. (1995) "Delivery of class I and class II MHC-restricted T-cell epitopes of listeriolysin of *Listeria monocytogenes* by attenuated *Salmonella*", Vaccine, vol. 13, No. 2, pp. 142-150.

Wu et al.(1996) "Engineering an intracellular pathway for major histocompatibility complex class II presentation of antigens." Cancer Res. 56: 21-26.

Skoble, J. et al. (Aug. 7, 2000). "Three Regions within ActA Promote Arp2/3 Complex-mediated Actin Nucleation and *Listeria monocytogenes* Motility," The Journal of cell Biology 150(3):527-537.

Smith, G.A. et al. (Sep. 1995). "Asymmetric Distribution of the *Listeria monocytogenes* ActA Protein is Required and Sufficient to Direct Actin-Based Motility," Molecular Microbiology 17:945-951.

Welch, M.D. et al. (Jul. 3, 1998). "Interaction of Human Arp2/3 Complex and the *Listeria monocytogenes* ActA Protein in Actin Filament Nucleation," Science 281 :105-108; pa-998020.

Weiskirch, et al (1997) "*Listeria monocytogenes*: a potent vaccine vector for neoplastic and infectious disease." Immunol. Rev, vol. 158, pp. 159-169.

Makela, et al. (1987) Hand Book of Experimental Immunology, vol. 1, chapter 3, pp. 3.1-3.13.

Mikayama, et al. (1993) "Molecular cloning and functional expression of a cDNA encoding gycosylation-inhibiting factor" Proc. Natl. Acad. Sci. USA 90:10056-10060.

Neilsen PE, "Peptide nucleic acids as therapeutic agents", Curr Opin Struct Biol 9:353-57, 1999.

International Search Report of Application No. PCT/US08/03067 issued on Aug. 29, 2008.

Vines A. et al. Identifaction and Characterization of Nucleotide Sequence Difference in Three Virulence-Associated Genes of *Listeria monocytogenes* Strains Representing Clinically Important Serotypes, Current Microbiol. May 1998, vol. 36, No. 5, pp. 309-318.

International Search Report of Application No. PCT/US07/10635 issued on Sep. 11, 2008.

Reilly RT, Gottlieb MB et al, "HER-2/*neu* Is a Tumor Rejection Target in Tolerized HER-2/*neu* Transgenic Mice" Cancer Res. Jul. 1, 2000; 60(13):3569-76.

Wei et al., "Protection against mammary tumor growth by vaccination with full-length, modified human ErbB-2 DNA", Int. J. Cancer, May 31, 1999; 81(5):748-54.

Muller W. J. (1991) Expression of activated oncogenes in the murine mammary gland: transgenic models for human breast cancer, Canc. Metastasis Rev. 10:217-27.

de Boer et al., "A Division Inhibitor and a Topological Specificity Factor Coded for by the Minicell Locus Determine Proper Placement of the Division Septum in *E. coli*" 1989, Cell 56:641-649.

Miller et al., "Xenograft Model of Progressive Human Proliferative Breast Disease" 1995, Faseb J., 9:190-199.

Ogasawara et al., "A strategy for making synthetic peptide vaccines" Proc. Nati. Acad. Sci. USA vol. 89, pp. 8995-8999, Oct. 1992.

Mata, M, Yao, Z, Zubair, A, Syres, K and Y Paterson, Evaluation of a recombinant *Listeria monocytogenes* expressing an HIV protein that protects mice against viral challenge. Vaccine 19:1435-45, 2001.

Ulmanen et al., "Transcription and Translation of Foreign Genes in *Bacillus subtilis* by the Aid of a Secretion Vector", 1985, J. Bacteriol. 162:176-182.

Gilman et al., "Isolation of sigma-2%specific promoters from *Bacillus subtilis* DNA" 1984, Gene 32:11-20.

International Search Report of Application No. PCT/US07/06292 issued on Jun. 17, 2008.

International Search Report of Application No. PCT/US01/09736 issued on Jul. 27, 2001.

Paterson et al. "Recombinant *Listeria monocytogenes* cancer vaccines", Current Opinion in Immunology, 1996, 8:664-669.

Disis et al. (1996) Peptide-Based, but Not Whole Protein, Vaccines Elicit Immunity to HER-2/neu, an Oncogenic Self Protein, The Journal of Immunology, vol. 156, 3151-3158.

Coussens et al. (1985) "Tyrosine Kinase Receptor with Extensive Homology to EGF Receptor Shares Chromosomal Location with neu Oncogene" Science, vol. 230, 1132-1139.

Knutson, K. L. et al., "Immunization with a HER-2/neu helper peptide vaccine generates HER-2/neu CD8 T-cell immunity in cancer patients" The Journal of Clinical Investigation, 107:477-484, 2001.

International Search Report of Application No. PCT/US05/32682 issued on Jun. 1, 2006.

International Search Report of Application No. PCT/US95/14741 issued on Feb. 15, 1996.

Camilli et al., "Dual roles of plcA in *Listeria Monocytogenes* pathogenesis", Mol. Microbiol. 1993, 8, 143157.

Silverman et al. "Expression of cmyc, c-raf-1, and c-Ki-ras in Azaserine-Induced pancreatic carcinomas and growing pancreas in rats", Mol. Carcinog 3(6):379-86, 1990.

Cohen, J. "Cancer Vaccines Get a Shot in the Arm" Science 262:841-843, 1993.

Bowie et al. "Deciphering the Message in Protein Sequences: Tolerance to Amino Acid Substitutions" Science 247:1306-1310, 1990.

Kumar et al. "Amino acid variations at a single residue in an autoimmune peptide profoundly affect its properties: T-cell activation, major histocompatability complex binding, and ability to block experimental allergic encephalomyelitis", PNAS 87:1337-1341, 1990.

Aggarwal et al., "Oral *Salmonella*: Malaria Circumsporozoite Recombinants Induce Specific CD8+ Cytotoxic T Cells", J. Exp. Med. 1990, 172, 1083-1090.

Boon et al., "Tumor Antigens Recognized by T Lymphocytes", Annu. Rev. Immunol. 1994, 12, 337-365.

Cheever et al., "T-Cell Immunity to Oncogenic Proteins Including Mutated RAS and Chimeric BCR-ABL", Ann. N.Y. Acad. Sci. 1993, 690:101-112.

Gansbacher et al., "Interleukin 2 Gene Transfer into Tumor Cells Abrogates Tumorigenicity and Induces Protective Immunity" J. Exp. Med. 1990, 172, 1217-1224.

Golumbek et al., "Treatment of Established Renal Cancer by Tumor Cells Engineered to Secrete Interleukin-4", Science 1991, 254, 713-716.

A. Kruisbeek, "In Vivo Depletion of CD4- and CD8-specific T cells" Current Protocols in Immunology, John Wiley & Sons, Inc., eds., 1994, V. 1, 4.1.1-4.1.2.

Restifo et al., "Identification of Human Cancers Deficient in Antigen Processing", J. Exp. Med. 1993, 177, 265-272.

Stover et al., "New Use of BCG for Recombinant Vaccines", Nature 1991, 351, 456-460.

Townsend et al., "Tumor Rejection after Direct Costimulation of CD8+ T Cells by B7-Transfected Melanoma Cells", Science 1993, 259, 368-370.

Travis J., "A Stimulating New Approach to Cancer Treatment", Science 1993, 259, 310-311.

Young J.F. et al., "Cloning and Expression of Influenza Virus Genes", The Origins of Pandemic Influenza Viruses, W.G. Laver, eds., Elsevier Science Publishing Co., Inc., NY, 1983, p. 129.

Serth et al., "Increased Levels of Human Papillomavirus Type 16 DNA in a Subset of Prostate Cancers" Cancer Res.1999 15; 59(4):823-5.

Paterson et al, Proceedings of the American Association for Cancer Research, Mar. 2000, 41:890, abstract #S25.

Pan et al, "Regression of Established Tumors in Mice Mediated by the Oral Administration of a Recombinant *Listeria monocytogenes* Vaccine" Cancer Research, Nov. 1, 1995, vol. 55:4776-4779.

Zhang et al., "Selection of Tumor Antigens as Targets for Immune Attack Using Immunohistochemistry: Protein Antigens", Clin. Cancer Res. 1998 4:2669-2676.

Disis et al., "Immunity to the HER-2/neu oncogenic protein", Ciba Found. Symp. 1994 187:198-211.

Gillespie, A.M. and Coleman, R.E., "The potential of melanoma antigen expression in cancer therapy", Cancer Treat. Rev. 1999 25(4):219-27.

Finn et al., MUC-1 Epithelial Tumor Mucin-Based Immunity and Cancer Vaccines, Immuno. Rev. 1995 145:61-89.

Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

McCarty et al., "Targeting p53 for Adoptive T-Cell Immunotherapy", Cancer Research 1998 15:58 2601-5.

McKaig et al., "Human Papillomavirus and Head and Neck Cancer: Epidemiology and Molecular Biology" Head Neck 1998 20 (3):250-65.

Pagano, J.S., "Epstein-Barr Virus: The First Human Tumor Virus and its Role in Cancer", Proc. Assoc. Am. Physicians 1999 111(6):573-80.

Punwaney et al., "Human Papillomavirus May be Common within Nasopharyngeal Carcinoma of Caucasian Americans: investigations of Epstein-Barr virus and human papilloma-virus in Eastern and Western Nasopharyngeal Carcinoma using Ligation-Dependent polymerase chain reaction", Head Neck 1999 21(1) :21-9.

Serth et al., "Increased Levels of Human Papillomavirus Type 16 DNA in Subset of Prostate Cancers", Cancer Res. 1999 15:59(4):823-5.

McCartey et al., "Targeting p53 for adoptive T-cell immunotherapy", Cancer Research 1998 15; 58:2601-5.

Berche et al., "Intracellular Growth of *Listeria monocytogenes* as a Prerequisite for in vivo Induction of T Cell-Mediated Immunity", J. Immunol. 1987, 138, 2266-2271.

Brown , T. et al., "An attenuated aroA *Salmonella typhimurium* vaccine elicits humoral and cellular immunity to cloned β-galactosidase in mice", J. of Infectious Diseases 1987, 155(1), 86-92.

Camilli et al., "Intracellular Methicillin Selection of *Listeria monocytogenes* Mutants Unable to replicate in a Macrophage Cell Line", PNAS USA 1989, 86, 5522-5526.

Cossart et al., "Listeriolysin O Is Essential for Virulence of *Listeria monocytogenes*: Direct Evidence Obtained by Gene Complementation", Infection and Immunity 57:3629-3636 (1989).

Flamm et al. "Introduction of pAMβ1 into *Listeria monocytogenes* by Conjugation and Homology Between Native *L. monocytogenes* Plasmids", Infection and Immunity 44:157-161(1984).

Gaillard et al., "Transposon Mutagenesis as a Tool to Study the Role of Hemolysin in the Virulence of *Liestria monocytogenes*", Infection and Immunology 52:50-55 (1986).

Jiang LL, Song HH et al., Characterization of a mutant *Listeria monocytogenes* strain expressing green fluorescent protein, Acta Bio Chim Biophys Sin (Shanghai) 2005, 37(1), 19-24.

Bergmann CI et al., "The neu oncogene encodes an epidermal growth factor receptor-related protein", Nature 319: 226, 1986.

Baloglu et al., "Immune responses of mice to vaccinia virus recombinants expressing either *Listeria monocytogenes* partial listeriolysin or *Brucella abortus* ribosomal L7/L12 protein" Vet Microbiol 2005, 109(1-2):11-7.

Portnoy et al., "Role of Hemolysin for the Intracellular Growth of *Listeria monocytogenes*", J. Exp. Med. 1988, 176, 1459-1471.

Portnoy et al., "γ Interferon Limits Access of *Listeria monocytogenes* to the Macrophage Cytoplasm", J. Exp. Med. 1989, 170, 2141-2146.

Jiang C et al., Mutations that decrease DNA binding of the processivity factor of the herpes simplex virus DNA polymerase reduce viral yield, alter the kinetics of viral DNA replication and decrease the fidelity of DNA replication, J. Virol. Apr. 2007, 81(7):3495-502.

Youngman, "Plasmid Vectors for Recovering and Exploiting Transpositions in *Bacillus* and Other Gram-Positives" 1987, pp. 79-103, in K. Hardy (ed.), Plasmids a Practical Approach, IRL Press, Oxford.

Bouwer H. et al., "Listeriolysin O is a target of the immune response to *Listeria monocytogenes*", J. of Experimental Medicine 1992, 175, 1467-1471.

Camili et al., "Insertional Mutagenesis of *Listeria monocytogenes* with a Novel Tn917 Derivative That Allows Direct Cloning of DNA Flanking Transposon Insertions", J. of Bacteriology 172:3738-3744 (1990).

Vitiello et al., "Development of a Lipopeptide-based therapeutic vaccine to treat chronic HBV infection", J. Clin. Invest., Jan. 1995, 95(1):341-349.

Ramaswamy M et al., Interactions and management issues in HSV and HIV coinfection Expert Rev Anti Infect Ther. Apr. 2007, 5(2):231-43.

Eisenlohr et al., "Flanking Sequences Influence the Presentation of an Endogenously Synthesized Peptide to Cytotoxic T Lymphocytes" The Journal of Experimental Medicine 175:481-487 (1992).

Gaillard et al, "In Vitro model of Penetration and Intracellular Growth of *Listeria monocytgenes* in the Human Enterocyte-Like Cell Line Caco-2", Infect. Immun. 1987, 55,2822-2829.

Lambiase et al., Topical Ereatment with nerve growth factor in the animal model of herpetic keratitis Graefes Arch Clin. Exp. Ophthalmol. May 4, 2007.

Merrifield et al., "Solid Phase Peptide Synthesis. I. The Synthesis of a Tetrapeptide" J. Am. Chem. Soc., 85:2149-2156 (1963).

Narang et al., "Improved phosphotriester method for the synthesis of gene fragments", 1979, Meth. Enzymol. 68:90-99.

Brown et al., "Chemical synthesis and cloning of a tyrosine tRNA gene", 1979, Meth. Enzymol. 68:109-151.

Beaucage et al., "deoxynucleoside phosphoramidites—a new class of key intermediates for deoxypolynucleotide synthesis" 1981, Tetra. Lett., 22:1859-1862.

Krieg AM et al., 1995, "CpG motifs in bacterial DNA trigger direct B-cell activation", Nature 374:546.

Sarmiento M et al., "IgG or IgM monoclonal antibodies reactive with different determinants on the molecular complex bearing lyt 2 antigen block t cell-mediated cytolysis in the absence of complement" J. Immunol. 125(6): 2665-72, 1980.

Caudy AA et al., "Fragile X-related protein and VIG associate withth e RNA interference machinery" Genes & Devel 16: 2491-96, 2002.

Ratner et al., "Complete Nucleotide Sequence of the AIDS virus, HTLV-III", Nature 1985, 313(1), 277-284.

Moore et al., "Introduction of Soluble Protein into the Class I Pathway of Antigen Processing and Presentation", Cell 1988, 54, 777-785.

Derbinski J.A., Schulte B. Kyewski and C. Klein, 2001, "Promiscuous gene expression in medullary thymic epithelial cells mirrors the peripheral self", Nat. Immunol. 2:1032.

Wuenscher et al., "Gene Disruption by Plasmid Integration in *Listeria monocytogenes*: Insertional Inactivation of the Listeriolysin Determinant lisA", Mol. Gen. Genet., 1991, 228, 177-182.

Ikonomidis, G. et al., "Delivery of a Viral Antigen to the Class I Processing and Presentation Pathway by *Listeria monocytogenes*", J. Exp. Med. 1994, 180, 2209-2218.

Connell et al., "Old microbes with new faces: molecular biology and the design of new vaccines", 1992 Current Opinion Immunol., 4:442-48.

Trieu-Cuot et al, "Suttle Vectors Containing a Multiple Cloning Site and lacZ x Gene for Conjugal transfer of DNA From *Eshcerichia Coli* to Gram-positive Bacteria", Gene 1991, 102, 99-104.

Charoenvit et al. "Inability of Malaria Vaccine to Induce Antibodies to a Protective Epitope Within Its Sequence", 1991 Sciences 251:668-671.

Cox "Malaria vaccines—progress and problems", 1991 TIB TECH 9:389-394.

Hoffman et al. "Naturally Acquired Antibodies to Sporozoites Do Not Prevent Malaria: Vaccine Development Implications" 1987 Science 237:639-642.

Hoffman et al. "Preerythrocytic malaria vaccine development", 1993 Mol. Immunological Considerations in Mal. Vaccine Dev. Ed. Good & Saul. pp. 149-167.

Haynes, "Scientific and Social Issues of Human Immunodeficiency Virus Vaccine Development" 1993 Science 260:1279-1286.

Bargmann CI et al., "The neu oncogene encodes an epidermal growth factor related protein", Nature 319: 226, 1986.

DeLibero et al, "antigen-specific lyt-2+ cytolytic t lymphocytes from mice infected with the intracellular bacterium *Listeria monocytogenes*"1986, J. Immunol. 137(8):2688-2694.

Ikonomidis, "Development of *Listeria Monocytogenes* as a vaccine vector for the delivery of a model antigen to the immune system (drug delivery)", 1996 Dissertation Abs. Int'l 57(4B) p. 2462 Abstract only.

Wilson et al. "Expression of a Leishmania chagasi antigen in *Listeria monocytogenes* for use in vaccine development; recombinant Leishmania chagasi antigen gene expression in *Listeria monocytogenes* using vector plasmid phly-Lcr1; potential recombinant vaccine", 1995 Am. J. Trop. Med. Hyg. 53(2) Suppl:132 Abstract only.

King CR et al., "Amplification of a novel v-erbB-related gene in a human mammary carcinoma", Science 229:974, 1985.

Goosens et al. "Attenuated *Listeria monocytogenes* as a live vector for induction of CD8+ T cells in vivo:a study with the nucleoprotein of the lymphocytic choriomeningitis virus" 1995 Intl Immunol. 7(5):797-805.

Tite et al., "Anti-viral immunity induced by recombinant nucleoprotein of Influenza A virus" 1990, Immunology 70:540-546.

Gao et al, "Recombinant *Salmonella typhimurium* Strains That Invade Nonphagocytic Cells Are Resistant to Recognition by Antigen-Specific Cytotoxic T Lymphocytes" 1992, Inf. & Imm., 60(9):3780-3789.

Brett et al, "Comparison of Antigen Presentation of Influenza A Nucleoprotein Expressed in Attenuated AroA—*Salmonella typhimurium* with That of Live Virus" 1993, J. Immunol. 150:2869-2884.

Marks et al., "By-passing Immunization Human Antibodies from V-gene Libraries Displayed on Phage" J. Mol. Biol. 222:581 (1991).

Garay-Malpartida HM, et al., "*CaSPredictor: a new computer-based tool for caspase substrate prediction*" JE Bioinformatics; Jun. 21, 2005; Suppl. 1:169-76.

H.G. Rammensee et al., "Protein-specific cytotoxic T lymphocytes, Recognition of transfectants expressing intracellular, membrane-associated for secreted forms of β-galactosidaes", 1989, Immunogenetics, 30:296.

Hoogenboom and Winter, "By-passing Immunisation Human Antibodies from Synthetic Repertoires of Germline VH Gene Segments Rearranged in Vitro" J. Mol. Biol. 227:381 (1991).

International Search Report of Application No. PCT/US07/18091 issued on Sep. 8, 2008.

Wu et al., "Engineering an intracellular pathway for major histocompatibilty complex class II presentation of antigens", Proc. Natl. Acad. Sci. USA 1995 92:11671-5.

Schnupf et al., "Phosphorylation, ubiquitination and degradation of listeriolysin O in mammalian cells: role of the PEST-like sequence" Cellular Microbiology 8(2): 353-364, 2006.

Amici et al., "DNA vaccination with full-length or truncated Neu induces protective immunity against the development of spontaneous mammary tumors in HER-2/neu transgenic mice", Gene Therapy (2000) 7, 703-706.

Angelov et al., "Therapeutic vaccine for acute and chronic motor neuron disease: implaction for amyotrophic lateral sclerosis" PNAS Apr. 15, 2003, vol. 100, No. 8, 4790-4795.

Chen et al., "DNA Vaccines Encoding Full-Length or Truncated Neu Induce Protective Immunity against Neu-expressing Mammary Tumors" Cancer Research 58, 1965-1971, May 1, 1998.

Concetti et al., "Autoantibody to p185erbB2/neu oncorprotein by vaccination with xenogenic DNA", Cancer Immunol. Immunother., Dec. 1996; 43(5):307-15.

Di Carlo et al., "Inhibition of mammary carcinogenesis by systemic interleukin 12 or p185neu DNA vaccination in Her-2/neu transgenic BALB/c mice" Clin. Cancer Res. Mar. 2001; 7(3 Suppl):830s-837s.

Disis et al., "Generation of T-Cell Immunity to the HER-2/neu Protein After Active Immunization with HER-2/neu Peptide-Based Vaccines" J Clin Oncol 20:2624-2632, 2002.

Dumitrescu et al., "Understanding breast cancer risk—where do we stand in 2005?" J. Cell. Mol. Med. vol. 9, No. 1, 2005, pp. 208-221.

Esserman et al., "Vaccination with the extracellular domain of p185neu prevents mammary tumor development in neu transgenic mice", Cancer Immunol. Immunother. Feb. 1999; 47(6):337-42.

Foy et al., "Vaccination with Her-2/neu DNA or protein subunits protects against growth of a Her-2/neu-expressing murine tumor" Vaccine, Mar. 21, 2001; 19(17-19):2598-606.

Lacey et al., "Phase IIa Safety and Immunogenicity of a Therapeutic Vaccine, TA-GW, in Persons with Genital Warts", The Journal of Infectious Diseases 1999; 179:612-618.

Piechocki et al., "Complementary Antitumor Immunity Induced by Plasmid DNA Encoding secreted and Cytoplasmic Human ErbB-2" The Journal of Immunology, 2001, 167:3367-3374.

Pilon et al., "Vaccination with Cytoplasmic ErbB-2 DNA Protects Mice from Mammary Tumor Growth without Anti-ErbB-2 Antibody", The Journal of Immunology, 2001, 167:3201-3206.

Rovero et al., "DNA Vaccination Against Rat Her-2/Neu p185 More Effectively Inhibits carcinogenesis Than Transplantable Carcinomas in Transgenic BALB/c Mice", The Journal of Immunology, 2000, 165:5133-5142.

Schlom et al., "Cancer Vaccines: Moving Beyond Current Paradigms" Clin. Cancer Res. 2007; 13(13); Jul. 1, 2007.

Maciag et al., "A *Listeria monocytogenes* based vaccine against HMW-MAA can impair the growth of HMW-MAA-expressing and non-expressing tumors in mice", Proceedings of the Annual Meeting of the American Association for Cancer Research, vol. 48, 2007, p. 449, Immunotherapy & Cancer Vaccines 2; Poster Presentations; Abstract #1881.

Powell et al., "Epitope spreading: protection from pathogens, but propagation of autoimmunity?", Clin. Exp. Dermatol., 2001, 26(5): 427-433, p. 431.

Disis et al., "Humoral epitope-spreading following immunization with a HER-2/neu peptide based vaccine in cancer patients", J. Clin. Immunol., 2004, 24(5): 571-578.

\* cited by examiner

VACCINIA VIRUS CONSTRUCTS EXPRESSING DIFFERENT
FORMS OF HPV16 E7 PROTEIN

US 8,268,326 B2

COMPOSITIONS COMPRISING HMW-MAA AND FRAGMENTS THEREOF, AND METHODS OF USE THEREOF

CROSS REFERENCE TO RELATED APPLICATIONS

This application claims priority from U.S. Provisional Application Ser. No. 60/960,538 filed Oct. 3, 2007, and is a continuation-in-part of U.S. application Ser. No. 11/889,715 filed Aug. 15, 2007, which claims priority from U.S. Provisional Application Ser. No. 60/837,608 filed Aug. 15, 2006, which is incorporated in its entirety herein by reference.

GOVERNMENT INTEREST STATEMENT

This invention was made in whole or in part with government support under Grant Number RO1CA109253 (Y.P.) and T32CA09140 (M.S.), awarded by the National Institutes of Health. The government may have certain rights in the invention.

FIELD OF INVENTION

This invention provides a recombinant polypeptide comprising a fragment of a High Molecular Weight Melanoma-Associated Antigen (HMW-MAA), recombinant Listeria strains comprising same, and methods of inducing an immune response and treating and impeding the growth of tumors, especially breast tumors, comprising administering same.

BACKGROUND OF THE INVENTION

In women, breast cancer is the second most common type of cancer and the second leading cause of cancer-related deaths. One in eight women in the United States will develop breast cancer during her lifetime. According to the American Cancer Society (ACS), approximately 200,000 new cases of breast cancer are diagnosed each year in the United States, and the disease causes about 41,000 deaths annually. The incidence of breast cancer rises after age 40. The highest incidence (approximately 80% of invasive cases) occurs in women over age 50. According to the American Cancer Society, about 0.22 percent of men cancer deaths are from breast cancer.

HMW-MAA, also known as the melanoma chondroitin sulfate proteoglycan (MCSP), is a transmembrane protein of 2322 residues. HMW-MAA is expressed on over 90% of surgically removed benign nevi and melanoma lesions, and is also expressed in basal cell carcinoma, tumors of neural crest origin (e.g. astrocytomas, gliomas, neuroblastomas and sarcomas), childhood leukemias, and lobular breast carcinoma lesions. In vitro experimental data shows that HMW-MAA is involved in the adhesion, spreading and migration of melanoma cells and may have a role in cell invasion and metastasis.

Treatments and cures for many tumors e.g. both HMW-MAA-expressing and non-HMW-MAA-expressing tumors, as well as methods for prevention especially in high risk populations, are urgently needed in the art.

SUMMARY OF THE INVENTION

In one embodiment, the present invention provides a recombinant Listeria strain comprising a recombinant polypeptide, wherein the recombinant polypeptide comprises a peptide encoded by SEQ ID NO: 23.

In another embodiment, the present invention provides a method of inducing an anti-HER-2/neu immune response in a subject, a method of delaying progression of a tumor in a subject, a method of treating or preventing breast cancer in a subject, whereby said breast cancer is associated with expression of HER-2/neu antigen in said subject comprising administering to said subject a composition comprising a recombinant Listeria strain comprising a recombinant polypeptide, wherein the recombinant polypeptide comprises a peptide encoded by SEQ ID NO: 23.

In another embodiment, the present invention provides a recombinant polypeptide comprising a peptide encoded by SEQ ID NO: 23 linked to a non-HMW-MAA oligopeptide selected from a listeriolysin (LLO) oligopeptide or a homologue thereof, an ActA oligopeptide or a homologue thereof, and a PEST-like oligopeptide or a homologue thereof.

DETAILED DESCRIPTION OF THE INVENTION

Figure 1:
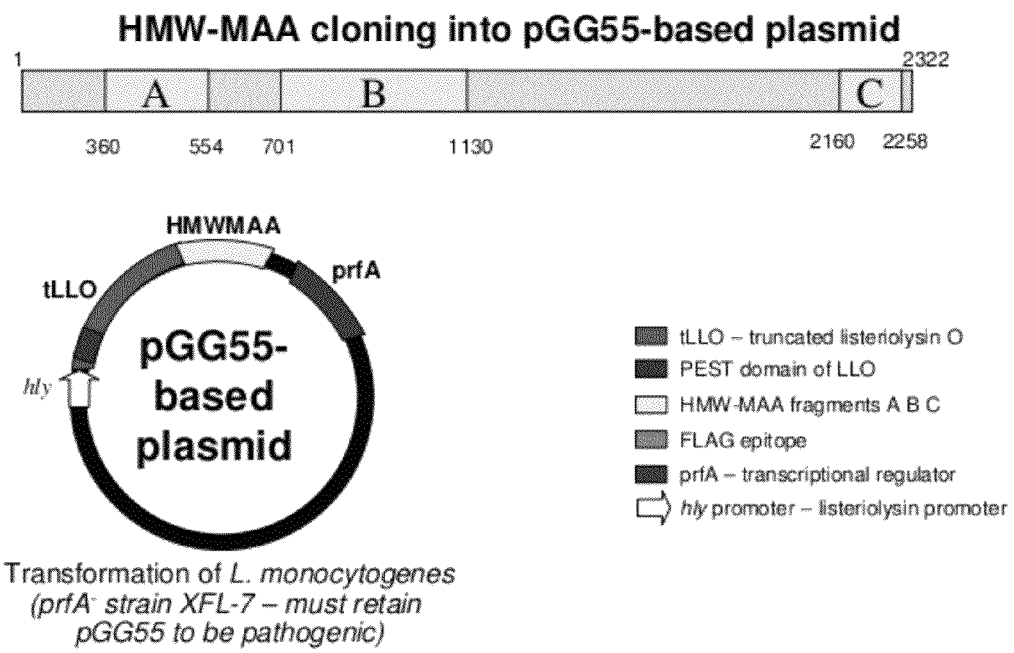
FIG. 1: HMW-MAA cloning into pGG55-based plasmid. Lm-LLO-HMW-MAA was generated by transforming the prfA$^-$ strain XFL-7 with the plasmid pGG-55. pGG-55 has the hly promoter driving expression of a non-hemolytic fusion of LLO-E7 and the prfA gene to select for retention of the plasmid. XFL-7 must retain the plasmid in order to be viable.

This invention provides recombinant polypeptides comprising a fragment of a High Molecular Weight Melanoma-Associated Antigen (HMW-MAA), recombinant *Listeria* strains comprising same, and methods of inducing an immune response and treating and impeding the growth of tumors, comprising administering same.

In one embodiment, the present invention provides a recombinant *Listeria* strain comprising a recombinant polypeptide, the recombinant polypeptide comprising a fragment of a HMW-MAA protein ("HMW-MAA fragment"). In one embodiment, the fragment of a HMW-MAA protein is encoded by the sequence set forth in SEQ ID NO: 23. In one embodiment said recombinant polypeptide further comprises a second polypeptide, which in one embodiment, is a non-HMW-MAA polypeptide and which, in another embodiment, enhances the immunogenicity of In another embodiment, a recombinant *Listeria* strain of the present invention expresses a recombinant polypeptide of the present invention. In another embodiment, a recombinant *Listeria* strain of the present invention comprises an isolated nucleic acid that encodes a recombinant polypeptide of the present invention. Each possibility represents a separate embodiment of the present invention.

In one embodiment, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In one embodiment, the present invention provides a *Listeria*, which in one embodiment, is a *Listeria* vaccine strain comprising an isolated nucleic acid or vector of the present invention. In one embodiment, a "*Listeria* vaccine strain" is used herein to refer to a recombinant *Listeria* organism that expresses a HMW-MAA or a portion thereof.

In one embodiment, two polynucleotides of the present invention are operably linked. For example, in one embodiment, polynucleotides encoding LLO and HMW-MAA-C are operably linked. In one embodiment, "operably linked" indicates that a single-stranded or double-stranded nucleic acid moiety comprises the two polynucleotides arranged within the nucleic acid moiety in such a manner that they are expressed together. By way of example, a promoter operably linked to the coding region of a gene is able to promote transcription of the coding region.

In one embodiment, a polynucleotide of the present invention comprises a promoter/regulatory sequence, which in one embodiment, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

In one embodiment, the term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

In one embodiment, a "constitutive" promoter is a nucleotide sequence which, when operably linked with a polynucleotide which encodes or specifies a gene product, causes the gene product to be produced in a living human cell under most or all physiological conditions of the cell.

In one embodiment, an "inducible" promoter is a nucleotide sequence which, when operably linked with a polynucleotide which encodes or specifies a gene product, causes the gene product to be produced in a living cell substantially only when an inducer which corresponds to the promoter is present in the cell.

In one embodiment, a "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

In another embodiment, the present invention provides a recombinant polypeptide comprising a fragment of a HMW-MAA protein operatively linked to a non-HMW-MAA oligopeptide selected from a listeriolysin (LLO) oligopeptide, an ActA oligopeptide, or a PEST-like oligopeptide or a fragment thereof. In one embodiment, the fragment has the same or a similar properties or function as the full length peptide or protein, as may be demonstrated using assays and tools known in the art. Properties and functions of full length peptides and proteins of the present invention are described in detail hereinbelow.

In other related aspects, the invention includes an isolated nucleic acid encoding a truncated ActA, LLO, or PEST protein and an isolated nucleic acid encoding a HMW-MAA protein or fragment operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid of the present invention. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In one embodiment, an isolated nucleic acid of the present invention is expressed under the control of a promoter, which in one embodiment, is an hly promoter, a prfA promoter, an ActA promoter, or a p60 promoter. In another embodiment, the promoter is CMV or CAG promoter. Other promoters that may be used are known in the art.

The invention also includes cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides a recombinant polypeptide comprising a fragment of a HMW-MAA protein, wherein the fragment consists of about amino acids (AA) 360-554 of the HMW-MAA protein from which the fragment is derived. In another embodiment, the fragment consists of about AA 701-1130. In another embodiment, the fragment has a sequence selected from SEQ ID No: 21-23. In another embodiment, the fragment consists of about AA 2160-2258. In another embodiment, the fragment has the SEQ ID No: 23. Each possibility represents a separate embodiment of the present invention.

In another embodiment, the present invention provides a recombinant polypeptide comprising a fragment of a HMW-MAA protein with an amino acid sequence encoded by a DNA sequence as set forth in SEQ ID No: 21.

In another embodiment, the present invention provides a recombinant polypeptide comprising a fragment of a HMW-MAA protein with an amino acid sequence encoded by a DNA sequence as set forth in SEQ ID No: 22.

In another embodiment, the present invention provides a recombinant polypeptide comprising a fragment of a HMW-MAA protein with an amino acid sequence encoded by a DNA sequence as set forth in SEQ ID No: 23.

In another embodiment, a recombinant polypeptide of the present invention further comprises a non-HMW-MAA peptide. In another embodiment, the non-HMW-MAA peptide enhances the immunogenicity of the fragment. Each possibility represents a separate embodiment of the present invention.

The non-HMW-MAA peptide is, in another embodiment, a listeriolysin (LLO) oligopeptide. In another embodiment, the non-HMW-MAA peptide is an ActA oligopeptide. In another embodiment, the non-HMW-MAA peptide is a PEST-like oligopeptide. As provided herein, fusion to LLO, ActA, PEST-like sequences and fragments thereof enhances the cell-mediated immunogenicity of antigens. In one embodiment, fusion to LLO, ActA, PEST-like sequences and fragments thereof enhances the cell-mediated immunogenicity of antigens in a variety of expression systems. In one embodiment, the expression system is viral, while in another embodiment, the expression system is bacterial. In another embodiment, the non-HMW-MAA peptide is any other immunogenic non-HMW-MAA peptide known in the art. Each possibility represents a separate embodiment of the present invention.

An LLO oligopeptide of methods and compositions of the present invention is, in another embodiment, a non-hemolytic LLO oligopeptide. In another embodiment, the oligopeptide is an LLO fragment. In another embodiment, the oligopeptide is a complete LLO protein. In another embodiment, the oligopeptide is any LLO protein or fragment thereof known in the art. Each possibility represents a separate embodiment of the present invention.

In one embodiment, the LLO protein is the major virulence factor of Lm responsible for the lysis of the phagolysosome. In one embodiment, LLO is highly immunogenic, in another embodiment, LLO induces maturation of antigen-specific T cells into Th1 cells, and in another embodiment, LLO induces interferon-gamma secretion by T cells.

In one embodiment, the LLO fragment comprises a mutation in the cholesterol binding domain or a deletion within the cholesterol binding domain, or a deletion of the cholesterol binding domain, which in one embodiment, renders the LLO non-hemolytic. In another embodiment, the LLO fragment is rendered non-hemolytic by chemical treatment. In another embodiment, the chemical treatment comprises glutaraldehyde. In another embodiment, the chemical treatment comprises a similarly acting compound. In another embodiment, the chemical treatment comprises any other suitable compound known in the art. Each possibility represents a separate embodiment of the present invention.

In another embodiment, the LLO protein utilized to construct vaccines of the present invention has the following sequence:
MKKIMLVFITLILVSLPIAQQTEAKDASAFNKENSIS SMAPPASPPASPKTPIEKKHADEIDKYIQ GLDYNKN-NVLVYHGDAVTNVP-PRKGYKDGNEYIVVEKKKKSINQN-NADIQVVNAISSLTYPG ALVKANSELVENQPDVLPVKRDSLTL-SIDLPGMTNQDNKIVVKNATKSNVNNAVNTLVERWN EKYAQAYPNVSAKIDYDDEMAYSES QLIAKFG-TAFKAVNNSLNVNFGAISEGKMQEEVISFKQ IYYN-VNVNEPTRPSRFFGKAVTKEQLQALGVNAENPPAYIS SVAYGRQVYLKLSTNSHSTKVK AAFDAAVSGKSVS-GDVELTNIIKNS SFKAVIYGGSAKDEVQIIDGNLGDL-RDILKKGATFNRETP GVPIAYTTNFLKDNELA-VIKNNSEYIETTSKAYTDGKINIDHS GGYVAQFNISWDEVNYDPEGN EIVQHKNWSENNK-SKLAHFTS SIYLPGNARNINVYAKECTGLAWEW-WRTVIDDRNLPLVKNR NISIWGTTLYPKYSNKVDN-PIE (GenBank Accession No. P13128; SEQ ID NO: 1; the nucleic acid sequence is set forth in GenBank Accession No. X15127). In one embodiment, the first 25 AA of the proprotein corresponding to this sequence are the signal sequence and are cleaved from LLO when it is secreted by the bacterium. Thus, according to this embodiment, the full length active LLO protein is 504 residues long. In another embodiment, the above sequence is used as the source of the LLO fragment incorporated in a vaccine of the present invention. In another embodiment, an LLO AA sequence of methods and compositions of the present invention is a homologue of SEQ ID No: 1. In another embodiment, the LLO AA sequence is a variant of SEQ ID No: 1. In another embodiment, the LLO AA sequence is a fragment of SEQ ID No: 1. In another embodiment, the LLO AA sequence is an isoform of SEQ ID No: 1. Each possibility represents a separate embodiment of the present invention.

In one embodiment, an isoform is a peptide or protein that has the same function and a similar or identical sequence to another peptide or protein, but is the product of a different gene. In one embodiment, a variant is a peptide or protein that differs from another peptide or protein in a minor way, which in one embodiment, refers to a mutation in a region that does not affect the function of the peptide or protein, and in another embodiment, a conservative mutation that does not affect the function of the peptide or protein.

In another embodiment, an LLO protein fragment is utilized in compositions and methods of the present invention. In another embodiment, the LLO fragment is an N-terminal fragment. In another embodiment, the N-terminal LLO fragment has the sequence:
MKKIMLVFITLILVSLPIAQQTEAKDASAFNKENSIS SVAPPASPPASPKTPIEKKHADEIDKYIQ GLDYNKN-NVLVYHGDAVTNVP-PRKGYKDGNEYIVVEKKKKSINQN-NADIQVVNAISSLTYP GALVKANSELVENQPDVLPVKRDSLTL-SIDLPGMTNQDNKIVVKNATKSNVNNAVNTLVER WNEKYAQAYSNVSAKIDYDDEMAY-SESQLIAKFGTAFKAVNNSLNVNFGAI-SEGKMQEEVIS FKQIYYNVNVNEPTRPSRFFGKAVT-KEQLQALGVNAENPPAYISSVAYGRQVYLKLSTNSHST KVKAAFDAAVSGKSVS GDVELTNIIKNSS-FKAVIYGGSAKDEVQIIDGNLGDLRDILKKGATFN RETPGVPIAYTTNFLKDNELA-VIKNNSEYIETTSKAYTDGKINIDHSG-GYVAQFNISWDEVNYD (SEQ ID NO: 2). In another embodiment, an LLO AA sequence of methods and compositions of the present invention comprises the sequence set forth in SEQ ID No: 2. In another embodiment, the LLO AA sequence is a homologue of SEQ ID No: 2. In another embodiment, the LLO AA sequence is a variant of SEQ ID No: 2. In another embodiment, the LLO AA sequence is a fragment of SEQ ID No: 2. In another embodiment, the LLO AA sequence is an isoform of SEQ ID No: 2. Each possibility represents a separate embodiment of the present invention.

In another embodiment, the LLO fragment has the sequence:
MKKIMLVFITLILVSLPIAQQTEAKDASAFNKENSIS SVAPPASPPASPKTPIEKKHADEIDKYIQ GLDYNKN-NVLVYHGDAVTNVP-PRKGYKDGNEYIVVEKKKKSINQN-NADIQVVNAISSLTYP GALVKANSELVENQPDVLPVKRDSLTL-SIDLPGMTNQDNKIVVKNATKSNVNNAVNTLVER WNEKYAQAYSNVSAKIDYDDEMAY-SESQLIAKFGTAFKAVNNSLNVNFGAISEGKMQEEVI SFKQIYYNVNVNEPTRPSRFFGKAVT-KEQLQALGVNAENPPAYISSVAYGRQVYLKLSTNSH STKVKAAFDAAVSGKSVS GDVELTNIIKNSS- FKAVIYGGSAKDEVQIiDGNLGDLRDILKKGA TFN-RETPGVPIAYTTNFLKDNELA-VIKNNSEYIETTSKAYTD (SEQ ID NO: 3). In another embodiment, an LLO AA sequence of methods and compositions of the present invention comprises the sequence set forth in SEQ ID No: 3. In another embodiment, the LLO AA sequence is a homologue of SEQ ID No: 3. In another embodiment, the LLO AA sequence is a variant of SEQ ID No: 3. In another embodiment, the LLO AA sequence is a fragment of SEQ ID No: 3. In another embodiment, the LLO AA sequence is an isoform of SEQ ID No: 3. Each possibility represents a separate embodiment of the present invention.

In another embodiment, the LLO fragment of methods and compositions of the present invention comprises a PEST-like domain. In another embodiment, an LLO fragment that comprises a PEST sequence is utilized as part of a composition or in the methods of the present invention.

In another embodiment, the LLO fragment does not contain the activation domain at the carboxy terminus. In another embodiment, the LLO fragment does not include cysteine 484. In another embodiment, the LLO fragment is a non-hemolytic fragment. In another embodiment, the LLO fragment is rendered non-hemolytic by deletion or mutation of the activation domain. In another embodiment, the LLO fragment is rendered non-hemolytic by deletion or mutation of cysteine 484. In another embodiment, an LLO sequence is rendered non-hemolytic by deletion or mutation at another location.

In another embodiment, the LLO fragment consists of about the first 441 AA of the LLO protein. In another embodiment, the LLO fragment comprises about the first 400-441 AA of the 529 AA full length LLO protein. In another embodiment, the LLO fragment corresponds to AA 1-441 of an LLO protein disclosed herein. In another embodiment, the LLO fragment consists of about the first 420 AA of LLO. In another embodiment, the LLO fragment corresponds to AA 1-420 of an LLO protein disclosed herein. In another embodiment, the LLO fragment consists of about AA 20-442 of LLO. In another embodiment, the LLO fragment corresponds to AA 20-442 of an LLO protein disclosed herein. In another embodiment, any ΔLLO without the activation domain comprising cysteine 484, and in particular without cysteine 484, are suitable for methods and compositions of the present invention.

In another embodiment, the LLO fragment corresponds to the first 400 AA of an LLO protein. In another embodiment, the LLO fragment corresponds to the first 300 AA of an LLO protein. In another embodiment, the LLO fragment corresponds to the first 200 AA of an LLO protein. In another embodiment, the LLO fragment corresponds to the first 100 AA of an LLO protein. In another embodiment, the LLO fragment corresponds to the first 50 AA of an LLO protein, which in one embodiment, comprises one or more PEST-like sequences.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

Each LLO protein and LLO fragment represents a separate embodiment of the present invention.

In another embodiment, homologues of LLO from other species, including known lysins, such as streptolysin O, perfringolysin O, pneumolysin, etc, or fragments thereof may be used as the non-HMW-MAA.

In another embodiment of methods and compositions of the present invention, a fragment of an ActA protein is fused to the HMW-MAA fragment. In another embodiment, the fragment of an ActA protein has the sequence:
MRAMMVVFITANCITINPDIIFAATDSEDS SLNTDEWEEEKTEEQPSEVNTGPRYETAR EVSSRDIKELEKSNKVRNTNKADLIAMLKEKAEKGP-NINNNNSEQTENAAINEEASGADRPAI QVERRHPGLPSDSAAEIKKRRKAIASSD-SELESLTYPDKPTKVNKKKVAKESVADASESDLDS SMQSADES SPQPLKANQQPFFPKVFKKIKDAGK-WVRDKIDENPEVKKAIVDKSAGLIDQLLTK KKSEEVNASDFPPPPTDEELRLALPETP-MLLGFNAPATSEPSSFEFPPPPTDEELRLALPETPMLL GFNAPATSEPSSFEFPPPPTEDELEI-IRETASSLDSSFTRGDLASLR-NAINRHSQNFSDFPPIPTEEE LNGRGGRP (SEQ ID No: 4). In another embodiment, an ActA AA sequence of methods and compositions of the present invention comprises the sequence set forth in SEQ ID No: 4. In another embodiment, the ActA AA sequence is a homologue of SEQ ID No: 4. In another embodiment, the ActA AA sequence is a variant of SEQ ID No: 4. In another embodiment, the ActA AA sequence is a fragment of SEQ ID No: 4. In another embodiment, the ActA AA sequence is an isoform of SEQ ID No: 4. Each possibility represents a separate embodiment of the present invention.

In another embodiment, the ActA fragment is encoded by a recombinant nucleotide comprising the sequence:
ATGCGTGCGATGATGGTGGTTTTCAT-TACTGCCAATTGCATTACGATTAACCCCGACATAA TATTTGCAGCGACAGATAGCGAAGAT-TCTAGTCTAAACACAGATGAATGGGAAGAAGAAA AAACAGAAGAGCAACCAAGCGAGG-TAAATACGGGACCAAGATACGAAACTGCACGTGAA GTAAGTTCACGTGATATTAAAGAACTA-GAAAAATCGAATAAAGTGAGAAATACGAACAAA GCAGACCTAATAGCAATGTTGAAA-GAAAAAGCAGAAAAAGGTCCAAATAT-CAATAATAAC AACAGTGAACAAACTGAGAATGCG-GCTATAAATGAAGAGGCTTCAGGAGCCGACCGACCA GCTATACAAGTGGAGCGTCGTCATCCAG-GATTGCCATCGGATAGCGCAGCGGAAATTAAAA AAAGAAGGAAAGCCATAGCATCATCG-GATAGTGAGCTTGAAAGCCTTACTTATCCGGATAA ACCAACAAAAGTAAATAAGAAAAAAGTG-GCGAAAGAGTCAGTTGCGGATGCTTCTGAAAG TGACTTAGATTCTAGCATGCAGTCAGCA-GATGAGTCTTCACCACAACCTTTAAAAGCAAAC CAACAACCATTTTTCCCTAAAGTATT-TAAAAAAATAAAAGATGCGGGGAAATGGGTACGTG ATAAAATCGACGAAAATCCTGAAGTAAA-GAAAGCGATTGTTGATAAAAGTGCAGGGTTAA TTGACCAATTATTAACCAAAAA-GAAAAGTGAAGAGGTAAATGCTTCG-GACTTCCCGCCACC ACCTACGGATGAAGAGTTAA-GACTTGCTTTGCCAGAGACACCAATGCTTCTTGGT-TTTAAT GCTCCTGCTACATCAGAACCGAGCTCAT-TCGAATTTCCACCACCACCTACGGATGAAGAGT TAAGACTTGCTTTGCCAGAGACGCCAAT-GCTTCTTGGTTTTAATGCTCCTGCTACATCGGAA CCGAGCTCGTTCGAATTTCCACCGCCTC-CAACAGAAGATGAACTAGAAATCATCCGGGAA ACAGCATCCTCGCTAGATTCTAGTTTTA-CAAGAGGGATTTAGCTAGTTTGAGAAATGCTA TTAATCGCCATAGTCAAAATTTCTCT-GATTTCCCACCAATCCCAACAGAAGAAGAGTTGAA CGGGAGAGGCGGTAGACCA (SEQ ID NO: 5). In another embodiment, the recombinant nucleotide has the sequence set forth in SEQ ID NO: 5. In another embodiment, an ActA-encoding nucleotide of methods and compositions of the present invention comprises the sequence set forth in SEQ ID No: 5. In another embodiment, the ActA-encoding nucleotide is a homologue of SEQ ID No: 5. In another embodiment, the ActA-encoding nucleotide is a variant of SEQ ID No: 5. In another embodiment, the ActA-encoding nucleotide is a fragment of SEQ ID No: 5. In another embodiment, the ActA-encoding nucleotide is an isoform of SEQ ID No: 5. Each possibility represents a separate embodiment of the present invention.

In another embodiment of methods and compositions of the present invention, a fragment of an ActA protein is fused to the HMW-MAA fragment. In another embodiment, the fragment of an ActA protein has the sequence as set forth in Genbank Accession No. AAF04762. In another embodiment, an ActA AA sequence of methods and compositions of the present invention comprises the sequence set forth in Genbank Accession No. AAF04762. In another embodiment, the ActA AA sequence is a homologue of Genbank Accession No. AAF04762. In another embodiment, the ActA AA sequence is a variant of Genbank Accession No. AAF04762.

In another embodiment, the ActA AA sequence is a fragment of Genbank Accession No. AAF04762. In another embodiment, the ActA AA sequence is an isoform of Genbank Accession No. AAF04762. Each possibility represents a separate embodiment of the present invention.

In another embodiment, the ActA fragment is encoded by a recombinant nucleotide comprising the sequence as set forth in Genbank Accession No. AF103807. In another embodiment, the recombinant nucleotide has the sequence set forth in Genbank Accession No. AF103807. In another embodiment, an ActA-encoding nucleotide of methods and compositions of the present invention comprises the sequence set forth in Genbank Accession No. AF103807. In another embodiment, the ActA-encoding nucleotide is a homologue of Genbank Accession No. AF103807. In another embodiment, the ActA-encoding nucleotide is a variant of Genbank Accession No. AF103807. In another embodiment, the ActA-encoding nucleotide is a fragment of Genbank Accession No. AF103807. In another embodiment, the ActA-encoding nucleotide is an isoform of Genbank Accession No. AF103807. Each possibility represents a separate embodiment of the present invention.

In another embodiment, the ActA fragment is any other ActA fragment known in the art. In another embodiment, a recombinant nucleotide of the present invention comprises any other sequence that encodes a fragment of an ActA protein. In another embodiment, the recombinant nucleotide comprises any other sequence that encodes an entire ActA protein. Each possibility represents a separate embodiment of the present invention.

In another embodiment of methods and compositions of the present invention, a PEST-like AA sequence is fused to the HMW-MAA fragment. In another embodiment, the PEST-like AA sequence is KENSISSMAPPASPPASPKT-PIEKKHADEIDK (SEQ ID NO: 6). In another embodiment, the PEST-like sequence is KENSISSMAPPASPPASPK (SEQ ID No: 7). In another embodiment, fusion of an antigen to any LLO sequence that includes one of the PEST-like AA sequences enumerated herein can enhance cell mediated immunity against HMW-MAA.

In another embodiment, the PEST-like AA sequence is a PEST-like sequence from a Listeria ActA protein. In another embodiment, the PEST-like sequence is KTEEQPSEVNT-GPR (SEQ ID NO: 8), KASVTDTSEGDLDSSM-QSADESTPQPLK (SEQ ID NO: 9), KNEEVNASDFPP-PPTDEELR (SEQ ID NO: 10), or RGGIPTSEEFSSLNSGDFTDDENSETTEEEIDR (SEQ ID NO: 11). In another embodiment, the PEST-like sequence is a variant of the PEST-like sequence described hereinabove, which in one embodiment, is KESVVDASE SDLDSSMQSADESTPQPLK (SEQ ID NO: 46), K SEEVNASDFPPPPTDEELR (SEQ ID NO: 47), or RGG RPTSEEFSSLNSGDFTDDENSETTEEEIDR (SEQ ID NO: 48), as would be understood by a skilled artisan. In another embodiment, the PEST-like sequence is from *Listeria seeligeri* cytolysin, encoded by the lso gene. In another embodiment, the PEST-like sequence is RSEVTISPAET-PESPPATP (SEQ ID NO: 12).

In another embodiment, the PEST-like sequence is from Streptolysin O protein of *Streptococcus* sp. In another embodiment, the PEST-like sequence is from *Streptococcus pyogenes* Streptolysin O, e.g. KQNTASTETTTTNEQPK (SEQ ID NO: 13) at AA 35-51. In another embodiment, the PEST-like sequence is from *Streptococcus equisimilis* Streptolysin O. e.g. KQNTANTETTTTNEQPK (SEQ ID NO: 14) at AA 38-54. In another embodiment, the PEST-like sequence has a sequence selected from SEQ ID NO: 8-14. In another embodiment, the PEST-like sequence has a sequence selected from SEQ ID NO: 6-14. In another embodiment, the PEST-like sequence is another PEST-like AA sequence derived from a prokaryotic organism.

Identification of PEST-like sequences is well known in the art, and is described, for example in Rogers S et al (Amino acid sequences common to rapidly degraded proteins: the PEST hypothesis. Science 1986; 234(4774):364-8) and Rechsteiner M et al (PEST sequences and regulation by proteolysis. Trends Biochem Sci 1996; 21(7):267-71). "PEST-like sequence" refers, in another embodiment, to a region rich in proline (P), glutamic acid (E), serine (S), and threonine (T) residues. In another embodiment, the PEST-like sequence is flanked by one or more clusters containing several positively charged amino acids. In another embodiment, the PEST-like sequence mediates rapid intracellular degradation of proteins containing it. In another embodiment, the PEST-like sequence fits an algorithm disclosed in Rogers et al. In another embodiment, the PEST-like sequence fits an algorithm disclosed in Rechsteiner et al. In another embodiment, the PEST-like sequence contains one or more internal phosphorylation sites, and phosphorylation at these sites precedes protein degradation.

In one embodiment, PEST-like sequences of prokaryotic organisms are identified in accordance with methods such as described by, for example Rechsteiner and Rogers (1996, Trends Biochem. Sci. 21:267-271) for LM and in Rogers S et al (Science 1986; 234(4774):364-8). Alternatively, PEST-like AA sequences from other prokaryotic organisms can also be identified based on this method. Other prokaryotic organisms wherein PEST-like AA sequences would be expected to include, but are not limited to, other *Listeria* species. In one embodiment, the PEST-like sequence fits an algorithm disclosed in Rogers et al. In another embodiment, the PEST-like sequence fits an algorithm disclosed in Rechsteiner et al. In another embodiment, the PEST-like sequence is identified using the PEST-find program.

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, R F. J. Mol. Biol. 157, 105 (1982). For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine.

$$\text{Hydropathy index}=10*\text{Kyte-Doolittle hydropathy index}+45$$

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

$$\text{PEST score}=0.55*\text{DEPST}-0.5*\text{hydrophobicity index}.$$

In another embodiment, "PEST sequence", "PEST-like sequence" or "PEST-like sequence peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the PEST-like sequence is any other PEST-like sequence known in the art. Each PEST-like sequence and type thereof represents a separate embodiment of the present invention.

"Fusion to a PEST-like sequence" refers, in another embodiment, to fusion to a protein fragment comprising a PEST-like sequence. In another embodiment, the term includes cases wherein the protein fragment comprises surrounding sequence other than the PEST-like sequence. In another embodiment, the protein fragment consists of the PEST-like sequence. Thus, in another embodiment, "fusion" refers to two peptides or protein fragments either linked together at their respective ends or embedded one within the other. Each possibility represents a separate embodiment of the present invention.

In another embodiment, the HMW-MAA fragment of methods and compositions of the present invention is fused to the non-HMW-MAA AA sequence. In another embodiment, the HMW-MAA fragment is embedded within the non-HMW-MAA AA sequence. In another embodiment, an HMW-MAA-derived peptide is incorporated into an LLO fragment, ActA protein or fragment, or PEST-like sequence. Each possibility represents a separate embodiment of the present invention.

In another embodiment, fusion proteins of the present invention are prepared by a process comprising subcloning of appropriate sequences, followed by expression of the resulting nucleotide. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid. In another embodiment, a similar strategy is used to produce a protein wherein an HMW-MAA fragment is embedded within a heterologous peptide.

In one embodiment, LLO sequences fused to a HMW-MAA fragment such as A, B, or C or Listeria expressing a HMW-MAA fragment increased the immune response to said peptide (Example 5), conferred antitumor immunity (Examples 4 and 5), and generated peptide-specific IFN-gamma-secreting CD8+ cells (Example 5). In one embodiment, ActA, LLO and/or PEST-like sequences fused to a peptide such as HPV E7 increased the immune response to said peptide, conferred antitumor immunity, and generated peptide-specific IFN-gamma-secreting CD8+ cells (Examples 7 and 8), even when the fusion peptide was expressed in a non-Listeria vector (Example 9).

In another embodiment, a recombinant polypeptide of the present invention is made by a process comprising the step of chemically conjugating a first polypeptide comprising an HMW-MAA fragment to a second polypeptide comprising a non-HMW-MAA peptide. In another embodiment, an HMW-MAA fragment is conjugated to a second polypeptide comprising the non-HMW-MAA peptide. In another embodiment, a peptide comprising an HMW-MAA fragment is conjugated to a non-HMW-MAA peptide. In another embodiment, an HMW-MAA fragment is conjugated to a non-HMW-MAA peptide. Each possibility represents a separate embodiment of the present invention.

In one embodiment, HMW-MAA used in the compositions and methods of the present invention, are involved in the adhesion, spreading and migration of melanoma cells and may have a role in cell invasion and metastasis. In one embodiment, HMW-MAA has a restricted expression in normal tissues, although it is expressed at high levels on both activated pericytes and pericytes in tumor angiogenic vasculature, which are associated with neovascularization in vivo.

The HMW-MAA protein from which HMW-MAA fragments of the present invention are derived is, in another embodiment, a human HMW-MAA protein. In another embodiment, the HMW-MAA protein is a mouse protein. In another embodiment, the HMW-MAA protein is a rat protein. In another embodiment, the HMW-MAA protein is a primate protein. In another embodiment, the HMW-MAA protein is from any other species known in the art. In another embodiment, the HMW-MAA protein is melanoma chondroitin sulfate proteoglycan (MCSP). In another embodiment, an AN2 protein is used in methods and compositions of the present invention. In one embodiment, AN2 is a murine homolog of HMW-MAA, and in one embodiment has 80% homology to HMW-MAA as well as a similar expression pattern and function. In another embodiment, an NG2 protein is used in methods and compositions of the present invention.

In another embodiment, the HMW-MAA protein of methods and compositions of the present invention has the sequence:
MQSGRGPPLPAPGLALALTLTMLARLA-SAASFFGENHLEVPVATALTDIDLQLQFSTSQ PEALLLLAAGPADHLLLQLYS GRLQVRLVLGQEELR-LQTPAETLLSDSIPHTVVLTVVEGWATL SVDGFLNAS-SAVPGAPLEVPYGLFVGGTGTLGLPYL-RGTSRPLRGCLHAATLNGRSLLRPLTPD VHEGCAEEFSASDDVALGFSGPHSLAAF-PAWGTQDEGTLEFTLTTQSRQAPLAFQAGGRRGDF IYVDIFEGHLRAVVEKGQGTVLLHNSVP-VADGQPHEVSVHINAHRLEISVDQYPTHTSNRGVLS YLEPRGSLLLGGLDAEASRHLQEHR-LGLTPEATNASLLGCMEDLSVNGQRRGL-REALLTRNMA AGCRLEEEEYEDDAYGHYEAFSTLA-PEAWPAMELPEPCVPEPGLPPVFANFTQLLTISPLVVAE GGTAWLEWRHVQPTLDLMEAELRKSQV-LFSVTRGARHGELELDIPGAQARKMFTLLDVVNR KARFIHDGSEDTSDQLVLEVSVTARVP-MPSCLRRGQTYLLPIQVNPVNDPPHIIFPHGSLMVILE HTQKPLGPEVFQAYDPDSACEGLTFQVLGTS SGLPVERRDQPGEPATEFSCRELEAGSLVYVH RGG-PAQDLTFRVSDGLQASPPATLKVVAIR-PAIQIHRSTGLRLAQGSAMPILPANLSVETNAVG QDVSVLFRVTGALQFGELQKQGAGGVEG-AEWWATQAFHQRDVEQGRVRYLSTDPQHHAYD TVENLALEVQVGQEILSNLSFPV-TIQRATVWMLRLEPLHTQNTQQETLT-TAHLEATLEEAGPSPP TFHYEVVQAPRKGN-LQLQGTRLSDGQGFTQDDIQAGRVTYGATARASEA-VEDTFRFRVTAPPY FSPLYTFPIHIGGDPDAPVLTNV-LLVVPEGGEGVLSADHLFVKSLNSASY-LYEVMERPRHGRLA WRGTQDKTTMVTSFTNEDLL-RGRLVYQHDDSETTEDDIPFVATRQGES SGD-MAWEEVRGVFR VAIQPVNDHAPVQTISRIFHVARG-GRRLLTTDDVAFSDADS GFADAQLVLTRKDLLFG-SIVAVD EPTRPIYRFTQEDLRKRRVLFVHS-GADRGWIQLQVSDGQHQATALLEVQASEPYLRVAN-GSSL VVPQGGQGTIDTAVLHLDTNLDIRS-GDEVHYHVTAGPRWGQLVRAGQ-PATAFSQQDLLDGAV LYSHNGSLSPRDTMAFS-VEAGPVHTDATLQVTIALEGPLAPLKLVRHKKIYVF-QGEAAAEIRRDQ LEAAQEAVPPADIVFSVKSPP-SAGYLVMVSRGALADEPPSLDPVQSF-SQEAVDTGRVLYLHSRP EAWSDAFSLDVAS GLGAPLEGVLVELEVLPAAIPLEAQNFS-VPEGGSLTLAPPLLRVSGPYFPTL LGLSLQVLEPPQH-GALQKEDGPQARTLSAFSWRMVEEQ-LIRYVHDGSETLTDSFVLMANASEM DRQSHPVAFTVTVLPVNDQPPILTTNT-GLQMWEGATAPIPAEALRSTDGDSGSEDLVYTIEQPS NGRVVLRGAPGTEVRSFTQAQLDGGLV-LFSHRGTLDGGFRFRLSDGEHTSPGHFFRVTAQKQV LLSLKGSQTLTVCPGSVQPLSSQTL-RASSSAGTDPQLLLYRVVRGPQLGRLF-HAQQDSTGEALV NFTQAEVYAGNILYEHEMPPEPF-WEAHDTLELQLS SPPARDVAATLAVAVSFEAACPQRPSHL WKNKGL-WVPEGQRARITVAALDASNLLAS-VPSPQRSEHDVLFQVTQFPSRGQLLVSEEPLHAG QPHFLQSQLAAGQLVYAHGGGGTQQDGF-HFRAHLQGPAGASVAGPQTSEAFAITVRDVNERP PQPQASVPLRLTRGSRAPISRAQLSVVD-PDSAPGEIEYEVQRAPHNGFLSLVGGGLGPVTRFTQA DVDSGRLAFVANGSSVAGIFQLSMSD-GASPPLPMSLAVDILPSAIEVQLRA-PLEVPQALGRSSLS QQQLRVVSDREEPEAAYRLIQG-PQYGHLLVGGRPTSAFS QFQIDQGEVVFAFTNFSSSHDHFRV LALARGVNA-SAVVNVTVRALLHVWAGGPWPQGATL-RLDPTVLDAGELANRTGSVPRFRLLE GPRHGRV-VRVPRARTEPGGSQLVEQFTQQDLEDGRLGLEVGR-PEGRAPGPAGDSLTLELWAQ GVPPAVASLDFA-TEPYNAARPYSVALLSVPEAARTEAGKPES STPT-GEPGPMASSPEPAVAKG GFLSFLEANMFSVIIPMCLV-LLLLALILPLLFYLRKRNKTGKHDVQVLTAKPRNGL-AGDTETFR KVEPGQAIPLTAVPGQGPPPGGQPD-PELLQFCRTPNPALKNGQYWV (SEQ ID No: 15). In another embodiment, an HMW-MAA AA sequence of methods and compositions of the present invention comprises the sequence set forth in SEQ ID No: 15. In another embodiment, the HMW-MAA AA sequence is a homologue of SEQ ID No: 15. In another embodiment, the HMW-MAA AA sequence is a variant of SEQ ID No: 15. In another embodiment, the HMW-MAA AA sequence is a fragment of SEQ ID No: 15. In another embodiment, the HMW-MAA AA sequence is an isoform of SEQ ID No: 15. Each possibility represents a separate embodiment of the present invention.

In another embodiment, the HMW-MAA protein of methods and compositions of the present invention is encoded by the sequence:
atgcagtccggccgcggcccccccacttc-cagcccccggcctggccttggctttgac-cctgactatgttggccagacttgcatccgcggcttccttcttcg gtgagaaccac-ctggaggtgcctgtggccacggctctgaccgacatagacctgcagctgcagttct-ccacgtcccagcccgaagccctccttctcctg gcagcaggcccagctgaccac-ctcctgctgcagctctactctggacgc-ctgcaggtcagacttgttctgggccaggaggagctgaggctgcagactc cagca-gagacgctgctgagtgactccatcccccacactgtggtgctgactgtcgtagagg-gctgggccacgttgtcagtcgatgggtttctgaacgcct cctcagcagtcccaggagcccccctagaggtc-
ccctatgggctctttgt-
tgggggcactgggacccttggcctgccctacctgaggggaaccagccg
acccctgaggggttgcctccatgcagc-
caccctcaatggccgcagcctcctccg-
gcctctgaccccgatgtgcatgagggctgtgctgaagagttttc tgccagtgat-
gatgtggcctgggcttctctgggccccactctctggctgccttcctgcctgggg-
cactcaggacgaaggaaccctagagtttacactc accacacagagccggcag-
gcaccttggccttccaggcaggggc-
cggcgtggggacttcatctatgtggacatatttgagggccacctgcgggcc gtg-
gtggagaagggccagggtaccgtattgctccacaacagtgtgcctgtggccgat-
gggcagcccatgaggtcagtgtccacatcaatgctcaccg gctggaaatctc-
cgtggaccagtacccctacgcatacttc-
gaaccgaggagtcctcagctacctg-
gagccacggggcagtctccttctcgggggctgg
atgcagaggcctctcgtcacctccag-
gaacaccgcctgggcctgacaccagag-
gccaccaatgcctccctgctgggctgcatggaagacctcagtgtc aatggcca-
gaggcggggctgcgggaagctttgctgacgcgcaacatggcagccggctgc-
aggctggaggaggaggagtatgaggacgatgccta tggacattat-
gaagctttctccaccctggccctgag-
gcttggccagccatggagctgcctgagc-
catgcgtgcctgagccagggctgcctcctgtcttt
gccaatttcacccagctgctgactat-
cagcccactggtggtggc-
cgagggggcacagcctggcttgagtggaggcatgtgcagcccacgctggacct
gatggaggctgagctgcgcaaatcccag-
gtgctgttcagcgtgac-
ccgagggggcacgccatggcgagctcgagctggacatcccgggagcccagg
cacgaaaaatgttcacctcctg-
gacgtggtgaaccgcaaggcccgct-
tcatccacgatggctctgaggacacctccgaccagctggtgctggaggtg tcggt-
gacggctcgggtgcccatgccctcatgccttcggaggggccaaacataccctct-
gcccatccaggtcaaacctgtcaatgacccaccccacatc atcttcccacatg-
gcagcctcatggtgatcctggaaca-
cacgcagaagccgctggggcctgag-
gttttccaggcctatgacccggactctgcctgtgag
ggcctcaccttccaggtccttggcac-
ctcctctggcctccccgtggagcgc-
cgagaccagcctggggagccggcgaccgagttctcctgccgggagtt ggag-
gccggcagcctagtctatgtccaccgcggtggtcctgcacaggacttgacgttcc-
gggtcagcgatggactgcaggccagccccccggccac gctgaaggtggtggc-
catccggccggccatacagatccaccg-
cagcacagggttgcgactggcccaaggctctgccatgcccatcttgcccgccaac
ctgtcggtggagaccaatgc-
cgtggggcaggatgtgagcgtgctgttc-
cgcgtcactggggccctgcagtttgggagctgcagaagcaggggcag
gtggggtggagggtgctgagtggtgggc-
cacacaggcgttccaccagcgggatgtg-
gagcaggccgcgtgaggtacctgagcactgacccacagc accacgcttacga-
caccgtggagaacctggccctggaggtgcaggtgggccaggagatcctgagca-
atctgtccttcccagtgaccatccagagagc cactgtgtggatgctgcggctg-
gagccactgcacactcagaacacccag-
caggagaccctcaccacagcccacctggaggccaccctggaggaggc aggc-
ccaagcccccaaccttccattatgaggtggttcaggctcccaggaaaggcaacc-
ttcaactacagggcacaaggctgtcagatggccagggc ttcacccaggatga-
catacaggctggccgggtgac-
ctatggggccacagcacgtgcctcagag-
gcagtcgaggacaccttccgtttccgtgtcacagc
tccaccatatttctccccactctatac-
cttccccatccacattggtggtgaccca-
gatgcgcctgtcctcaccaatgtcctcctcgtggtgcctgagggtgg tgagggt-
gtcctctctgctgaccacctcttttgtcaagagtctcaacagtgccagctacctctatg
aggtcatggagcggccccgccatgggaggttggct tggcgtgggacacagga-
caagaccactatggtgacatccttcac-
caatgaagacctgttgcgtgccggctggtctaccagcatgatgactccgagac
cacacgaagatgatatccatttgttgc-
tacccgccagggcgagagcagtggtga-
catggcctgggaggaggtacggggtgtcttccgagtggccatcc agcccgt-
gaatgaccacgccccctgtgcagaccatcagccggatcttccatgtggcccgggt-
gggcggcggctgctgactacagacgacgtggcctt cagcgatgct-
gactcgggctttgctgacgcccagctg-
gtgcttacccgcaaggacctcctctttg-
gcagtatcgtggccgtagatgagcccacgcggc
catctaccgcttcacccaggaggacct-
caggaagaggcgagtactgttcgtg-
cactcaggggctgaccgtggctggatccagctgcaggtgtccgacg ggcaa-
caccaggccactgcgctgctggaggtgcaggcctcggaaccctacctccgtgtg-
gccaacggctccagccttgtggtccctcaagggggcc agggcaccatcga-
cacggccgtgctccacctggacaccaac-
ctcgacatccgcagtggggatgaggtc-
cactaccacgtcacagctggccctcgctg
gggacagctagtccgggctggtcagc-
cagccacagccttctcccagcaggacct-
gctggatggggccgttctctatagccacaatggcagcctcagcc cccgcgacac-
catggccttccgtggaagcagggccagtgcacacggatgccaccctacaagt-
gaccattgcctagagggcccactggccccact gaagctggtccggcacaagaa-
gatctacgtcttcagggagaggcagct-
gagatcagaagggaccagctggaggcagcccaggaggcagtgccac ctgca-
gacatcgtattctcagtgaagagcccaccgagtgccggctacctggtgatggtgtc-
gcgtgcgccttggcagatgagccaccccagcctggac cctgtcagagcttctc-
ccaggaggcagtggacacaggcagggtc-
ctgtacctgcactcccgccctgaggcctggagcgatgccttctcgctggatgt
ggcctcaggcctgggtgctcccctc-
gagggcgtccttgtggagctggaggt-
gctgcccgctgccatcccactagaggcgcaaaacttcagcgtccctg agggtg-
gcagcctcaccctggccctccactgctccgtgtctccgggccctacttccccactc-
tcctgggcctcagcctgcaggtgctggagccacccc agcatggagccctgca-
gaaggaggacggaacctcaagccaggac-
cctcagcgccttctcctggagaatggtgaagagcagctgatccgctacgtgc
atgacgggagcgagacactgacaga-
cagttttgtcctgatggctaatgcctc-
cgagatggatcgccagagccatcctgtggccttcactgtcactgtcct gcctgt-
caatgaccaaccccccatcctcactacaaacacaggcctgcagatgtgggaggg-
ggccactgcgcccatccctgcggaggctctgaggagc acggacggc-
gactctgggtctgaggatctggtcta-
caccatcgagcagcccag-
caacgggcgggtagtgctgcgggggcgccgggcactgaggt
gcgcagcttcacgcaggcccagctg-
gacggcgggctcgtgctgtgttctcacaca-
gaggaaccctggatggaggcttccgcttccgcctctctgacggc gagcacacttc-
ccccggacacttcttccgagtgacggcccagaagcaagtgctcctctcgctgaag-
ggcagccagacactgactgtctgcccaggggtc cgtccagccactcagcagtca-
gaccctcagggccagctccagcgcag-
gcactgaccccagctcctgctctaccgtgtggtgcggggccccagcta ggccg-
gctgttccacgcccagcaggacagcacaggggaggccctggtgaacttcactca-
ggcagaggtctacgctgggaatattctgtatgagcatg agatgcccccccgagc-
cttttgggaggcccatgatcccta-
gagctcagctgtcctgccgcctgc-
ccggggacgtggccgccaccttgctgtggct
gtgtcttttgaggctgcctgtc-
cccagcgccccagccacctctggaagaa-
caaaggtctctgggtccccgagggcagcgggccaggatcaccgtgg
ctgctctggatgcctccaatctcttggc-
cagcgttccatcaccccagcgctcagag-
catgatgtgctcttccaggtcacacagttcccagccggggcca gctgttggtgtc-
cgaggagcccctccatgctgggcagcccacttcctgcagtcccagctggctgc-
agggcagtagtgtatgcccacggcggtgggg gcacccagcaggatggcttc-
cactttcgtgcccacctccaggggccag-
cagggggcctccgtggctggaccccaaacctcagaggcctttgccatcac ggt-
gagggatgtaaatgagcggcccccctcagccacaggcctctgtcccactccggctc acccgaggctctcgtgccccatctcccgggcccagctg agtgtggtggaccca-
gactcagctcctggggagattgagtac-
gaggtccagcgggcaccccacaacggct-
tcctcagcctggtgggtggtggcctgg
ggcccgtgacccgcttcacgcaagc-
cgatgtggattcagggcggctggcct-
tcgtggccaacgggagcagcgtggcaggcatcttccagctgagcat gtct-
gatggggccagcccaccccctgcccatgtcctggctgtggacatcctaccatccg-
ccatcgaggtgcagctgcgggcaccccctggaggtgcccc
aagctttggggcgctcctcactgagc-
cagcagcagctccgggtggtttca-
gatcgggaggagccagaggcagcataccgcctcatccagggacccca
gtatgggcatctcctggtgggcgggcg-
gcccacctcggccttcagccaattcca-
gatagaccagggcgaggtggtctttgccttcaccaacttctcctcc tctcatgac-
cacttcagagtcctggcactggctaggggtgtcaatgcatcagccgtagtgaacgt-
cactgtgagggctctgctgcatgtgtgggcaggtg ggccatggcccagggtgc-
caccctgcgcctggaccccaccgtccta-
gatgctggcgagctggccaaccgcacaggcagtgtgccgcgcttccgcc tcctg-
gagggaccccggcatggccgcgtggtccgcgtgccccgagccaggacggagc-
ccgggggcagccagctggtggagcagttcactcagca ggaccttgaggacgg-
gaggctggggctggaggtgggcaggcca-
gagggagggccccccggccccgcaggtgacagtctcactctggagctgtgg
gcacagggcgtcccgcctgctgtggc-
ctccctggactttgccactgagcctta-
caatgctgcccggccctacagcgtggccctgctcagtgtcccgag gccgccg-
gacggaagcagggaagccagagagcagcaccccacaggcgagccaggccca-
tggcatccagcctgagccgctgtggccaag ggaggcttcctgagcttccttgag-
gccaacatgttcagcgtcatcatc-
cccatgtgcctggtacttctgctcctggcgctcatcctgcccctgctcttctacct
ccgaaaacgcaacaagacgggcaagcat-
gacgtccaggtcctgactgccaagc-
cccgcaacggcctggctggtgacaccgagacctttcgcaaggt ggagccaggc-
caggccatcccgctcacagctgtgcctggccaggggcccctccaggaggcca-
gcctgacccagagctgctgcagttctgccgga cacccaaccctgccttaagaatg-
gccagtactgggtgtgaggcctggc-
ctgggcccagatgctgatcgggccagggacaggc (SEQ ID No: 16). In another embodiment, the recombinant nucleotide has the sequence set forth in SEQ ID NO: 16. In another embodiment, an HMW-MAA-encoding nucleotide of methods and compositions of the present invention comprises the sequence set forth in SEQ ID No: 16. In another embodiment, the HMW-MAA-encoding nucleotide is a homologue of SEQ ID No: 16. In another embodiment, the HMW-MAA-encoding nucleotide is a variant of SEQ ID No: 16. In another embodiment, the HMW-MAA-encoding nucleotide is a fragment of SEQ ID No: 16. In another embodiment, the HMW-MAA-encoding nucleotide is an isoform of SEQ ID No: 16. Each possibility represents a separate embodiment of the present invention.

In another embodiment, the HMW-MAA protein of methods and compositions of the present invention has an AA sequence set forth in a GenBank entry having an Accession Numbers selected from NM_001897 and X96753. In another embodiment, the HMW-MAA protein is encoded by a nucleotide sequence set forth in one of the above GenBank entries. In another embodiment, the HMW-MAA protein comprises a sequence set forth in one of the above GenBank entries. In another embodiment, the HMW-MAA protein is a homologue of a sequence set forth in one of the above GenBank entries. In another embodiment, the HMW-MAA protein is a variant of a sequence set forth in one of the above GenBank entries. In another embodiment, the HMW-MAA protein is a fragment of a sequence set forth in one of the above GenBank entries. In another embodiment, the HMW-MAA protein is an isoform of a sequence set forth in one of the above GenBank entries. Each possibility represents a separate embodiment of the present invention.

The HMW-MAA fragment utilized in the present invention comprises, in another embodiment, AA 360-554. In another embodiment, the fragment consists essentially of AA 360-554. In another embodiment, the fragment consists of AA 360-554. In another embodiment, the fragment comprises AA 701-1130. In another embodiment, the fragment consists essentially of AA 701-1130. In another embodiment, the fragment consists of AA 701-1130. In another embodiment, the fragment comprises AA 2160-2258. In another embodiment, the fragment consists essentially of 2160-2258. In another embodiment, the fragment consists of 2160-2258. Each possibility represents a separate embodiment of the present invention.

In some embodiments, a polypeptide of the present invention will comprise a fragment of a HMW-MAA protein, in any form or embodiment as described herein. In some embodiments, any of the polypeptides of the present invention will consist of a fragment of a HMW-MAA protein, in any form or embodiment as described herein. In some embodiments, of the compositions of this invention will consist essentially of a fragment of a HMW-MAA protein, in any form or embodiment as described herein. In some embodiments, the term "comprise" refers to the inclusion of the indicated active agent, such as the fragment of a HMW-MAA protein, or the fragment of a HMW-MAA protein and a non-HMW-MAA polypeptide, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In another embodiment, the HMW-MAA fragment is approximately 98 AA in length. In another embodiment, the length is approximately 194 AA. In another embodiment, the length is approximately 430 AA.

In another embodiment, the length is approximately 98-194 AA. In another embodiment, the length is approximately 194-430 AA. In another embodiment, the length is approximately 98-430 AA.

In another embodiment, the length of the HMW-MAA fragment of the present invention is at least 8 amino acids (AA). In another embodiment, the length is more than 8 AA. In another embodiment, the length is at least 9 AA. In another embodiment, the length is more than 9 AA. In another embodiment, the length is at least 10 AA. In another embodiment, the length is more than 10 AA. In another embodiment, the length is at least 11 AA. In another embodiment, the length is more than 11 AA. In another embodiment, the length is at least 12 AA. In another embodiment, the length is more than 12 AA. In another embodiment, the length is at least about 14 AA. In another embodiment, the length is more than 14 AA. In another embodiment, the length is at least about 16 AA. In another embodiment, the length is more than 16 AA. In another embodiment, the length is at least about 18 AA. In another embodiment, the length is more than 18 AA. In another embodiment, the length is at least about 20 AA. In another embodiment, the length is more than 20 AA. In another embodiment, the length is at least about 25 AA. In another embodiment, the length is more than 25 AA. In another embodiment, the length is at least about 30 AA. In another embodiment, the length is more than 30 AA. In another embodiment, the length is at least about 40 AA. In another embodiment, the length is more than 40 AA. In another embodiment, the length is at least about 50 AA. In another embodiment, the length is more than 50 AA. In another embodiment, the length is at least about 70 AA. In another embodiment, the length is more than 70 AA. In another embodiment, the length is at least about 100 AA. In another embodiment, the length is more than 100 AA. In another embodiment, the length is at least about 150 AA. In another embodiment, the length is more than 150 AA. In another embodiment, the length is at least about 200 AA. In another embodiment, the length is more than 200 AA. Each possibility represents a separate embodiment of the present invention.

In another embodiment, the length is about 8-50 AA. In another embodiment, the length is about 8-70 AA. In another embodiment, the length is about 8-100 AA. In another embodiment, the length is about 8-150 AA. In another embodiment, the length is about 8-200 AA. In another embodiment, the length is about 8-250 AA. In another embodiment, the length is about 8-300 AA. In another embodiment, the length is about 8-400 AA. In another embodiment, the length is about 8-500 AA. In another embodiment, the length is about 9-50 AA. In another embodiment, the length is about 9-70 AA. In another embodiment, the length is about 9-100 AA. In another embodiment, the length is about 9-150 AA. In another embodiment, the length is about 9-200 AA. In another embodiment, the length is about 9-250 AA. In another embodiment, the length is about 9-300 AA. In another embodiment, the length is about 10-50 AA. In another embodiment, the length is about 10-70 AA. In another embodiment, the length is about 10-100 AA. In another embodiment, the length is about 10-150 AA. In another embodiment, the length is about 10-200 AA. In another embodiment, the length is about 10-250 AA. In another embodiment, the length is about 10-300 AA. In another embodiment, the length is about 10-400 AA. In another embodiment, the length is about 10-500 AA. In another embodiment, the length is about 11-50 AA. In another embodiment, the length is about 11-70 AA. In another embodiment, the length is about 11-100 AA. In another embodiment, the length is about 11-150 AA. In another embodiment, the length is about 11-200 AA. In another embodiment, the length is about 11-250 AA. In another embodiment, the length is about 11-300 AA. In another embodiment, the length is about 11-400 AA. In another embodiment, the length is about 11-500 AA. In another embodiment, the length is about 12-50 AA. In another embodiment, the length is about 12-70 AA. In another embodiment, the length is about 12-100 AA. In another embodiment, the length is about 12-150 AA. In another embodiment, the length is about 12-200 AA. In another embodiment, the length is about 12-250 AA. In another embodiment, the length is about 12-300 AA. In another embodiment, the length is about 12-400 AA. In another embodiment, the length is about 12-500 AA. In another embodiment, the length is about 15-50 AA. In another embodiment, the length is about 15-70 AA. In another embodiment, the length is about 15-100 AA. In another embodiment, the length is about 15-150 AA. In another embodiment, the length is about 15-200 AA. In another embodiment, the length is about 15-250 AA. In another embodiment, the length is about 15-300 AA. In another embodiment, the length is about 15-400 AA. In another embodiment, the length is about 15-500 AA. In another embodiment, the length is about 8-400 AA. In another embodiment, the length is about 8-500 AA. In another embodiment, the length is about 20-50 AA. In another embodiment, the length is about 20-70 AA. In another embodiment, the length is about 20-100 AA. In another embodiment, the length is about 20-150 AA. In another embodiment, the length is about 20-200 AA. In another embodiment, the length is about 20-250 AA. In another embodiment, the length is about 20-300 AA. In another embodiment, the length is about 20-400 AA. In another embodiment, the length is about 20-500 AA. In another embodiment, the length is about 30-50 AA. In another embodiment, the length is about 30-70 AA. In another embodiment, the length is about 30-100 AA. In another embodiment, the length is about 30-150 AA. In another embodiment, the length is about 30-200 AA. In another embodiment, the length is about 30-250 AA. In another embodiment, the length is about 30-300 AA. In another embodiment, the length is about 30-400 AA. In another embodiment, the length is about 30-500 AA. In another embodiment, the length is about 40-50 AA. In another embodiment, the length is about 40-70 AA. In another embodiment, the length is about 40-100 AA. In another embodiment, the length is about 40-150 AA. In another embodiment, the length is about 40-200 AA. In another embodiment, the length is about 40-250 AA. In another embodiment, the length is about 40-300 AA. In another embodiment, the length is about 40-400 AA. In another embodiment, the length is about 40-500 AA. In another embodiment, the length is about 50-70 AA. In another embodiment, the length is about 50-100 AA. In another embodiment, the length is about 50-150 AA. In another embodiment, the length is about 50-200 AA. In another embodiment, the length is about 50-250 AA. In another embodiment, the length is about 50-300 AA. In another embodiment, the length is about 50-400 AA. In another embodiment, the length is about 50-500 AA. In another embodiment, the length is about 70-100 AA. In another embodiment, the length is about 70-150 AA. In another embodiment, the length is about 70-200 AA. In another embodiment, the length is about 70-250 AA. In another embodiment, the length is about 70-300 AA. In another embodiment, the length is about 70-400 AA. In another embodiment, the length is about 70-500 AA. In another embodiment, the length is about 100-150 AA. In another embodiment, the length is about 100-200 AA. In another embodiment, the length is about 100-250 AA. In another embodiment, the length is about 100-300 AA. In another embodiment, the length is about 100-400 AA. In another embodiment, the length is about 100-500 AA. Each possibility represents a separate embodiment of the present invention.

Each HMW-MAA protein and each fragment thereof represents a separate embodiment of the present invention.

In another embodiment, a recombinant polypeptide of the methods and compositions of the present invention comprises a signal sequence. In another embodiment, the signal sequence is from the organism used to construct the vaccine vector. In another embodiment, the signal sequence is a LLO signal sequence. In another embodiment, the signal sequence is an ActA signal sequence. In another embodiment, the signal sequence is a Listerial signal sequence. In another embodiment, the signal sequence is any other signal sequence known in the art. Each possibility represents a separate embodiment of the present invention.

The terms "peptide" and "recombinant peptide" refer, in another embodiment, to a peptide or polypeptide of any length. In another embodiment, a peptide or recombinant peptide of the present invention has one of the lengths enumerated above for an HMW-MAA fragment. Each possibility represents a separate embodiment of the present invention. In one embodiment, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S═O, O═C—NH, $CH_2$—O, $CH_2$—$CH_2$, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), *-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH═CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

Peptides or proteins of this invention may be prepared by various techniques known in the art, including phage display libraries (Hoogenboom and Winter, J. Mol. Biol. 227:381 (1991); Marks et al., J. Mol. Biol. 222:581 (1991)).

In one embodiment, the present invention provides a vector comprising an oligonucleotide encoding a polypeptide of the present invention. In one embodiment, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

In another embodiment, the present invention provides a vaccine comprising a recombinant *Listeria* strain of the present invention. In one embodiment, the vaccine additionally comprises an adjuvant. In one embodiment, the vaccine additionally comprises a cytokine, chemokine, or combination thereof. In one embodiment, a vaccine is a composition which elicits an immune response to an antigen or polypeptide in the composition as a result of exposure to the composition. In another embodiment, the vaccine or composition additionally comprises APCs, which in one embodiment are autologous, while in another embodiment, they are allogeneic to the subject.

In another embodiment, the present invention provides a vaccine comprising a recombinant polypeptide of the present invention and an adjuvant. In another embodiment, the present invention provides a vaccine comprising a recombinant oligonucleotide of the present invention.

In another embodiment, the present invention provides an immunogenic composition comprising a recombinant polypeptide of the present invention. In another embodiment, the immunogenic composition of methods and compositions of the present invention comprises a recombinant vaccine vector encoding a recombinant peptide of the present invention. In another embodiment, the immunogenic composition comprises a plasmid encoding a recombinant peptide of the present invention. In another embodiment, the immunogenic composition comprises an adjuvant. In one embodiment, a vector of the present invention may be administered as part of a vaccine composition. Each possibility represents a separate embodiment of the present invention.

The immunogenic composition utilized in methods and compositions of the present invention comprises, in another embodiment, a recombinant vaccine vector. In another embodiment, the recombinant vaccine vector comprises a recombinant peptide of the present invention. In another embodiment, the recombinant vaccine vector comprises an isolated nucleic acid of the present invention. In another embodiment, the recombinant vaccine vector comprises an isolated nucleic acid encoding a recombinant peptide of the present invention. Each possibility represents a separate embodiment of the present invention.

In another embodiment, the present invention provides a recombinant vaccine vector encoding a recombinant polypeptide of the present invention. In another embodiment, the present invention provides a recombinant vaccine vector comprising a recombinant polypeptide of the present invention. In another embodiment, the expression vector is a plasmid. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). Each possibility represents a separate embodiment of the present invention.

In another embodiment, the vector is an intracellular pathogen. In another embodiment, the vector is derived from a cytosolic pathogen. In another embodiment, the vector is derived from an intracellular pathogen.

In another embodiment, an intracellular pathogen induces a predominantly cell-mediated immune response. In another embodiment, the vector is a *Salmonella* strain. In another embodiment, the vector is a BCG strain. In another embodiment, the vector is a bacterial vector. In another embodiment, dendritic cells transduced with a vector of the present invention may be administered to the subject to upregulate the subject's immune response, which in one embodiment is accomplished by upregulating CTL activity.

In another embodiment, the recombinant vaccine vector induces a predominantly Th1-type immune response.

An immunogenic composition of methods and compositions of the present invention comprises, in another embodiment, an adjuvant that favors a predominantly Th1-type immune response. In another embodiment, the adjuvant favors a predominantly Th1-mediated immune response. In another embodiment, the adjuvant favors a Th1-type immune response. In another embodiment, the adjuvant favors a Th1-mediated immune response. In another embodiment, the adjuvant favors a cell-mediated immune response over an antibody-mediated response. In another embodiment, the adjuvant is any other type of adjuvant known in the art. In another embodiment, the immunogenic composition induces the formation of a T cell immune response against the target protein. Each possibility represents a separate embodiment of the present invention.

In another embodiment, the adjuvant is MPL. In another embodiment, the adjuvant is QS21. In another embodiment, the adjuvant is a TLR agonist. In another embodiment, the adjuvant is a TLR4 agonist. In another embodiment, the adjuvant is a TLR9 agonist. In another embodiment, the adjuvant is RESIQUIMOD®. In another embodiment, the adjuvant is imiquimod. In another embodiment, the adjuvant is a CpG oligonucleotide. In another embodiment, the adjuvant is a cytokine or a nucleic acid encoding same. In another embodiment, the adjuvant is a chemokine or a nucleic acid encoding same. In another embodiment, the adjuvant is IL-12 or a nucleic acid encoding same. In another embodiment, the adjuvant is IL-6 or a nucleic acid encoding same. In another embodiment, the adjuvant is a lipopolysaccharide. In another embodiment, the adjuvant is as described in Fundamental Immunology, 5th ed. (August 2003): William E. Paul (Editor); Lippincott Williams & Wilkins Publishers; Chapter 43: Vaccines, GJV Nossal, which is hereby incorporated by reference. In another embodiment, the adjuvant is any other adjuvant known in the art. Each possibility represents a separate embodiment of the present invention.

In one embodiment, a "predominantly Th1-type immune response" refers to an immune response in which IFN-gamma is secreted. In another embodiment, it refers to an immune response in which tumor necrosis factors is secreted. In another embodiment, it refers to an immune response in which IL-2 is secreted. Each possibility represents a separate embodiment of the present invention.

In another embodiment, the vector is selected from *Salmonella* sp., *Shigella* sp., BCG, *L. monocytogenes* (which embodiment is exemplified in Example 2), *E. coli*, and *S. gordonii*. In another embodiment, the fusion proteins are delivered by recombinant bacterial vectors modified to escape phagolysosomal fusion and live in the cytoplasm of the cell. In another embodiment, the vector is a viral vector. In other embodiments, the vector is selected from Vaccinia (which embodiment is exemplified in Example 8), Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, the vector is a naked DNA vector. In another embodiment, the vector is any other vector known in the art. Each possibility represents a separate embodiment of the present invention.

In another embodiment, the present invention provides an isolated nucleic acid encoding a recombinant polypeptide of the present invention. In one embodiment, the isolated nucleic acid comprises a sequence sharing at least 85% homology with a nucleic acid encoding a recombinant polypeptide of the present invention. In another embodiment, the isolated nucleic acid comprises a sequence sharing at least 90% homology with a nucleic acid encoding a recombinant polypeptide of the present invention. In another embodiment, the isolated nucleic acid comprises a sequence sharing at least 95% homology with a nucleic acid encoding a recombinant polypeptide of the present invention. In another embodiment, the isolated nucleic acid comprises a sequence sharing at least 97% homology with a nucleic acid encoding a recombinant polypeptide of the present invention. In another embodiment, the isolated nucleic acid comprises a sequence sharing at least 99% homology with a nucleic acid encoding a recombinant polypeptide of the present invention.

In another embodiment, the present invention provides a vaccine comprising a recombinant nucleotide molecule of the present invention and an adjuvant. In another embodiment, the present invention provides a recombinant vaccine vector comprising a recombinant nucleotide molecule of the present invention. In another embodiment, the present invention provides a recombinant vaccine vector encoding a recombinant polypeptide of the present invention. In another embodiment, the present invention provides a recombinant vaccine vector comprising a recombinant polypeptide of the present invention. In another embodiment, the expression vector is a plasmid. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). Each possibility represents a separate embodiment of the present invention.

Methods for preparing peptide vaccines are well known in the art and are described, for example, in EP1408048, United States Patent Application Number 20070154953, and OGASAWARA et al (Proc. Natl. Acad. Sci. USA Vol. 89, pp. 8995-8999, October 1992). In one embodiment, peptide evolution techniques are used to create an antigen with higher immunogenicity. Techniques for peptide evolution are well known in the art and are described, for example in U.S. Pat. No. 6,773,900.

In one embodiment, a vaccine is a composition which elicits an immune response to an antigen or polypeptide in the composition as a result of exposure to the composition.

In another embodiment, the present invention provides a recombinant *Listeria* strain comprising a recombinant nucleotide molecule of the present invention. In another embodiment, the present invention provides a recombinant *Listeria* strain comprising a recombinant polynucleotide of the present invention.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. In one embodiment, the *Listeria* strain is a *Listeria* strain comprising LLO, while in another embodiment, the *Listeria* strain is a *Listeria* strain comprising ActA, while in another embodiment, the *Listeria* strain is a *Listeria* strain comprising PEST-like sequences.

In another embodiment, the *Listeria* strain is attenuated by deletion of a gene. In another embodiment, the *Listeria* strain is attenuated by deletion of more than 1 gene. In another embodiment, the *Listeria* strain is attenuated by deletion or inactivation of a gene. In another embodiment, the *Listeria* strain is attenuated by deletion or inactivation of more than 1 gene.

In another embodiment, the gene that is mutated is hly. In another embodiment, the gene that is mutated is actA. In another embodiment, the gene that is mutated is plc A. In another embodiment, the gene that is mutated is plcB. In another embodiment, the gene that is mutated is mpl. In another embodiment, the gene that is mutated is inl A. In another embodiment, the gene that is mutated is inlB. In another embodiment, the gene that is mutated is bsh.

In another embodiment, the *Listeria* strain is an auxotrophic mutant. In another embodiment, the *Listeria* strain is deficient in a gene encoding a vitamin synthesis gene. In another embodiment, the *Listeria* strain is deficient in a gene encoding pantothenic acid synthase.

In another embodiment, the *Listeria* strain is deficient in an AA metabolism enzyme. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid. CysK. In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the *Listeria* strain is deficient in one or more of the genes described hereinabove.

In another embodiment, the *Listeria* strain is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylaminoimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, the *Listeria* strain is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family.

In another embodiment, the gene is a subunit of one of the above proteins.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the passaging attenuates the strain, or in another embodiment, makes the strain less virulent. Methods for passaging a recombinant *Listeria* strain through an animal host are known in the art, and are described, for example, in U.S. patent application Ser. No. 10/541,614. Each possibility represents a separate embodiment of the present invention.

Each *Listeria* strain and type thereof represents a separate embodiment of the present invention.

In another embodiment, the recombinant *Listeria* of methods and compositions of the present invention is stably transformed with a construct encoding an antigen or an LLO-antigen fusion. In one embodiment, the construct contains a polylinker to facilitate further subcloning. Several techniques for producing recombinant *Listeria* are known; each technique represents a separate embodiment of the present invention.

In another embodiment, the construct or heterologous gene is integrated into the Listerial chromosome using homologous recombination. Techniques for homologous recombination are well known in the art, and are described, for example, in Frankel, F R, Hegde, S, Lieberman, J, and Y Paterson. Induction of a cell-mediated immune response to HIV gag using *Listeria monocytogenes* as a live vaccine vector. J. Immunol. 155: 4766-4774, 1995; Mata, M, Yao, Z, Zubair, A, Syres, K and Y Paterson, Evaluation of a recombinant *Listeria monocytogenes* expressing an HIV protein that protects mice against viral challenge. Vaccine 19:1435-45, 2001; Boyer, J D, Robinson, T M, Maciag, P C, Peng, X, Johnson, R S, Pavlakis, G, Lewis, M G, Shen, A, Siliciano, R, Brown, C R, Weiner, D, and Y Paterson. DNA prime *Listeria* boost induces a cellular immune response to SIV antigens in the Rhesus Macaque model that is capable of limited suppression of SIV239 viral replication. Virology. 333: 88-101, 2005. In another embodiment, homologous recombination is performed as described in U.S. Pat. No. 6,855,320. In another embodiment, a temperature sensitive plasmid is used to select the recombinants. Each technique represents a separate embodiment of the present invention.

In another embodiment, the construct or heterologous gene is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed. In another embodiment, the position in the genome where the foreign gene has been inserted by transposon mutagenesis is unknown.

In another embodiment, the construct or heterologous gene is integrated into the Listerial chromosome using phage integration sites (Lauer P, Chow M Y et al, Construction, characterization, and use of two LM site-specific phage integration vectors. J Bacteriol 2002; 184(15): 4177-86). In another embodiment, an integrase gene and attachment site of a bacteriophage (e.g. U153 or PSA listeriophage) is used to insert the heterologous gene into the corresponding attachment site, which can be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In another embodiment, the construct is carried by the *Listeria* strain on a plasmid. LM vectors that express antigen fusion proteins have been constructed via this technique. Lm-GG/E7 was made by complementing a prfA-deletion mutant with a plasmid containing a copy of the prfA gene and a copy of the E7 gene fused to a form of the LLO (hly) gene truncated to eliminate the hemolytic activity of the enzyme, as described herein. Functional LLO was maintained by the organism via the endogenous chromosomal copy of hly. In another embodiment, the plasmid contains an antibiotic resistance gene. In another embodiment, the plasmid contains a gene encoding a virulence factor that is lacking in the genome of the transformed *Listeria* strain. In another embodiment, the virulence factor is prfA. In another embodiment, the virulence factor is LLO. In another embodiment, the virulence factor is ActA. In another embodiment, the virulence factor is any of the genes enumerated above as targets for attenuation. In another embodiment, the virulence factor is any other virulence factor known in the art. Each possibility represents a separate embodiment of the present invention.

In another embodiment, a recombinant peptide of the present invention is fused to a Listerial protein, such as PI-PLC, or a construct encoding same. In another embodiment, a signal sequence of a secreted Listerial protein such as hemolysin, ActA, or phospholipases is fused to the antigen-encoding gene. In another embodiment, a signal sequence of the recombinant vaccine vector is used. In another embodiment, a signal sequence functional in the recombinant vaccine vector is used. Each possibility represents a separate embodiment of the present invention.

In another embodiment, the construct is contained in the *Listeria* strain in an episomal fashion. In another embodiment, the foreign antigen is expressed from a vector harbored by the recombinant *Listeria* strain.

Each method of expression in *Listeria* represents a separate embodiment of the present invention.

In another embodiment, the present invention provides a method of inducing an anti-HMW-MAA immune response in a subject, comprising administering to the subject a composition comprising a recombinant *Listeria* strain of the present invention, thereby inducing an anti-HMW-MAA immune response in a subject.

In another embodiment, a subject is administered his/her own allogeneic cells, which in one embodiment, elicit an immune response to an antigen. In another embodiment, the compositions and methods of the present invention result in the expression of stimulatory cytokines, which in one embodiment, are Th1 cytokines, which in one embodiment, is IFN-gamma. In one embodiment, the expression of stimulatory cytokines contributes to the anti-tumor effect of the compositions and methods. In another embodiment, the compositions and methods of the present invention result in the expression of gamma delta T cells.

In another embodiment, the present invention provides compositions and methods for inducing non-specific anti-tumor responses. In one embodiment, immunization with a melanoma antigen, such as HMW-MAA peptide, protects against a type of melanoma that does not express the antigen (Example 4).

In another embodiment, the present invention provides a method of inducing an immune response against an HMW-MAA-expressing tumor in a subject, comprising administering to the subject a composition comprising a recombinant *Listeria* strain of the present invention, thereby inducing an immune response against an HMW-MAA-expressing tumor.

As provided herein, vaccines of the present invention induce antigen-specific immune response, as shown by multiple lines of evidence—e.g. inhibition of tumor growth, tetramer staining, measurement of numbers of tumor-infiltrating CD8+ T cells, FACS, and chromium release assay.

In another embodiment, the present invention provides a method of inducing an immune response against a pericyte in a subject, comprising administering to the subject a composition comprising a recombinant *Listeria* strain of the present invention, thereby inducing an immune response against a pericyte.

In another embodiment, HER-2/neu is an EGF receptor family member that is over-expressed in many human cancers (breast (40%), melanoma (30%), pancreatic (20%), ovarian (30%) & gastric cancer (19%)). In another embodiment, the present invention demonstrates that *L. monocytogenes* strains expressing HMW-MAA fragments induce an immune response directed to HER-2/neu antigen. In another embodiment, the present invention demonstrates that *L. monocytogenes* strains expressing HMW-MAA fragments induce a cytotoxic T cell response directed to HER-2/neu antigen. In another embodiment, the present invention demonstrates that *L. monocytogenes* strains expressing HMW-MAA fragments induce an immune response directed to HER-2/neu antigen thus controlling tumor growth. In another embodiment, the present invention demonstrates that *L. monocytogenes* strains expressing HMW-MAA fragments induce an immune response directed to HER-2/neu antigen thus breaking tolerance to an endogenous tumor antigen.

In another embodiment, the present invention provides a method of delaying progression of a tumor in a subject, comprising administering to the subject a composition comprising a recombinant polypeptide of the present invention, thereby delaying progression of a tumor in a subject. In another embodiment, the subject mounts an immune response against a pericyte of the tumor. In another embodiment, the pericyte is in a vasculature of the solid tumor. In one embodiment, said tumor is a solid tumor. Each possibility represents a separate embodiment of the present invention.

Figure 13:
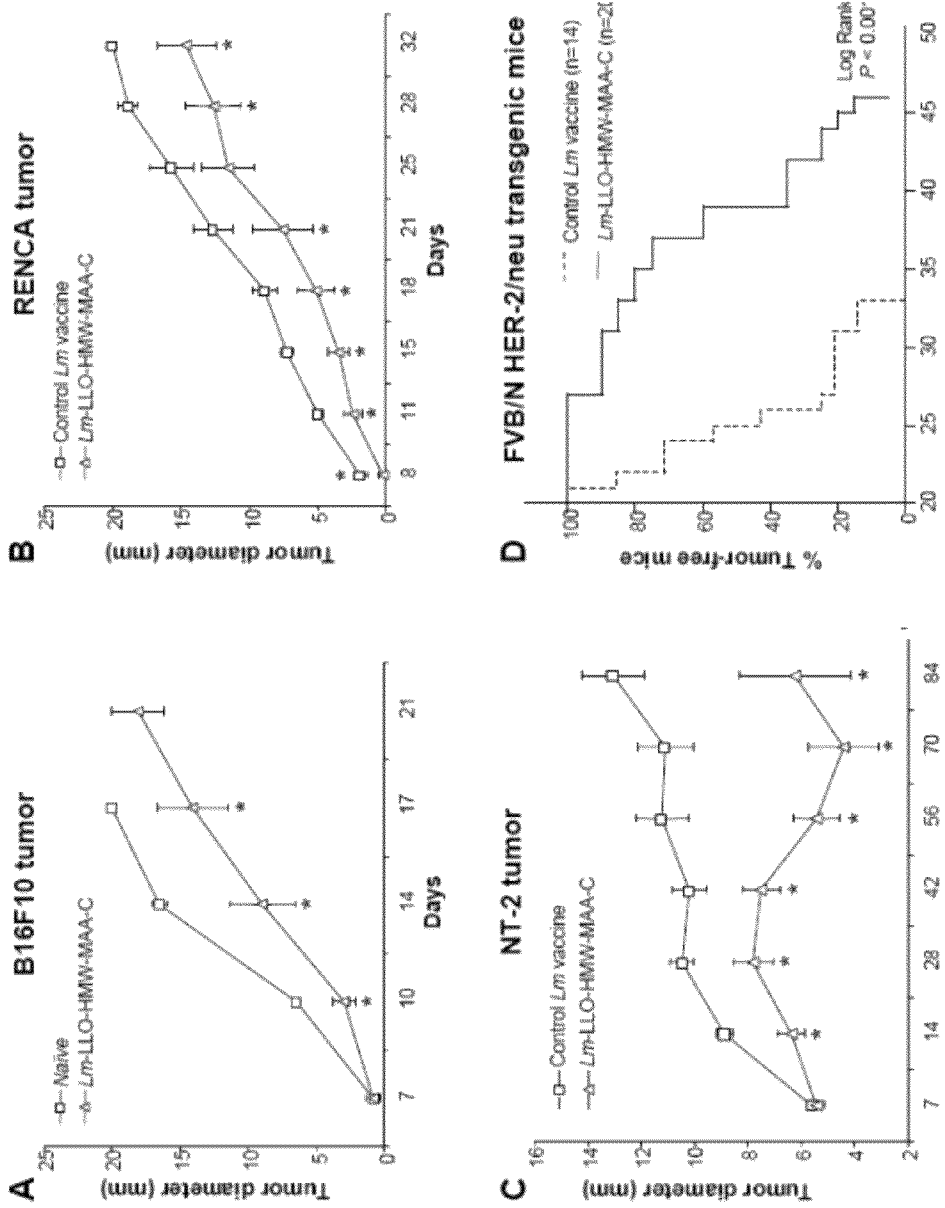
FIG. 13. Vaccination of mice with Lm-HMW-MAA-C impairs the growth of HMW-MAA/AN2-negative tumors. A, C57B1/6 mice were inoculated s.c. with B16F10 cells and either immunized i.p. on days 3, and 17 with Lm-HMW-MAA-C (n=8) or left untreated (n=7). B, BALB/c mice were inoculated s.c. with RENCA cells and immunized i.p. on days 3, 10 and 17 with either Lm-HMW-MAA-C (n=8) or an equivalent dose of a control Lm vaccine. C, FVB/N mice were inoculated s.c. with NT-2 tumor cells and immunized i.p. on days 7, 14 and 21 with either Lm-HMW-MAA-C (n=5) or an equivalent dose of a control Lm vaccine (n=8). Tumor sizes were measured for each individual tumor and the values expressed as the mean diameter in millimeters±SEM. *, P≦0.05, Mann-Whitney test. D, 8-week old FVB/N HER-2/neu transgenic mice were immunized i.p. followed by two additional doses at one week intervals with either Lm-HMW-MAA-C (n=20) or an equivalent dose of a control Lm vaccine (n=14).

The data presented herein demonstrating the effectiveness of the Lm-HMW-MAA-C vaccine in delaying the onset of mammary tumors in FVB/N HER-2/neu transgenic mice (FIG. 13D).

In another embodiment, the present invention provides a method of impeding a vascularization of a solid tumor in a subject, comprising administering to the subject a composition comprising a recombinant polypeptide of the present invention, thereby impeding a vascularization of a solid tumor in a subject. In another embodiment, the present invention provides a method of impeding a vascularization of a breast tumor in a subject, comprising administering to the subject a composition comprising a recombinant polypeptide of the present invention, thereby impeding a vascularization of a breast tumor in a subject. In another embodiment, the subject mounts an immune response against a pericyte of the solid tumor. In another embodiment, the pericyte is in a vasculature of the solid tumor. Each possibility represents a separate embodiment of the present invention.

In another embodiment, the present invention provides a method of delaying progression of a HER-2/neu-expressing tumor in a subject, comprising administering to the subject a composition comprising a recombinant polypeptide of the present invention, thereby delaying progression of a HER-2/neu-expressing tumor in a subject. In another embodiment, the subject mounts an immune response against the HER-2/neu expressing tumor. Each possibility represents a separate embodiment of the present invention In another embodiment, the methods of the present invention provide that a recombinant *Listeria* strain of the invention comprising a HMW-MAA fragment induces anti-HER-2/neu immune response. In another embodiment, the methods of the present invention provide that a recombinant *Listeria* strain of the invention comprising a HMW-MAA fragment C (encoded by SEQ ID NO: 23) induces an anti-HER-2/neu immune response.

In another embodiment, the methods of the present invention provide that a recombinant polypeptide comprising HMW-MAA fragment induces anti-HER-2/neu immune response. In another embodiment, the methods of the present invention provide that a recombinant polypeptide comprising a HMW-MAA fragment C (encoded by SEQ ID NO: 23) induces an anti-HER-2/neu immune response.

In another embodiment, the present invention provides that the immune response induced by a recombinant polypeptide comprising a HMW-MAA fragment or a recombinant *Listeria* strain comprising a recombinant polypeptide comprising a HMW-MAA fragment is effective at controlling tumor growth, wherein the tumor expresses HER-2/neu antigen. In another embodiment, the present invention provides that the immune response induced by a recombinant polypeptide comprising a HMW-MAA fragment or a recombinant *Listeria* strain comprising a recombinant polypeptide comprising a HMW-MAA fragment is effective at controlling breast tumor growth. In another embodiment, the present invention provides that the immune response induced by a recombinant polypeptide comprising a HMW-MAA fragment or a recombinant *Listeria* strain comprising a recombinant polypeptide comprising a HMW-MAA fragment is effective at controlling breast cancer. In another embodiment, the present invention provides that the immune response induced by a recombinant polypeptide comprising a HMW-MAA fragment or a recombinant *Listeria* strain comprising a recombinant polypeptide comprising a HMW-MAA fragment is effective at controlling a solid tumor growth wherein the solid tumor expresses HER-2/neu antigen.

In another embodiment, the present invention provides a method that comprises a dual action: (1) destroying the vasculature of a tumor; and (2) inducing an anti-HER-2/neu immune response. In another embodiment, the present invention has an additive effect in view of drugs that control either one of the actions. In another embodiment, the present invention has a synergistic effect compared to drugs that control either one of the actions. In another embodiment, the present invention provides compositions and methods that are extremely effective in controlling the growth of tumors expressing HER-2/neu antigen due to the dual action as described hereinabove. In another embodiment, the present invention provides compositions and methods for administering a recombinant *Listeria* vaccine strain expressing an LLO protein fused to a fragment of HMW-MAA to a mammal resulting in impairment of tumor growth, in another embodiment, regression of existing tumors (FIG. 13C), in another embodiment, abrogation of tolerance to existing tumors, and, in another embodiment, the death of tumor tissue, which in one embodiment is a HER-2/neu-expressing tumor. In another embodiment, the present invention provides compositions and methods for delaying the onset of mammary tumors in populations pre-disposed to developing mammary tumors (FIG. 13D), due to genetic or environmental factors.

In another embodiment, the present invention provides a method of impeding the growth of a solid tumor expressing HER-2/neu antigen in a subject, comprising administering to the subject a composition comprising a recombinant *Listeria* strain of the present invention, thereby impeding a growth and/or delaying progression of a solid tumor expressing HER-2/neu antigen in a subject. In another embodiment, the subject mounts an immune response against a pericyte of the solid tumor. In another embodiment, the subject mounts an immune response against HER-2/neu antigen of the solid tumor. In another embodiment, the pericyte is in a vasculature of the solid tumor. Each possibility represents a separate embodiment of the present invention.

In another embodiment, the present invention provides a method of treating a solid tumor expressing HER-2/neu in a subject, comprising administering to the subject a composition comprising a recombinant *Listeria* strain of the present invention, thereby treating a solid tumor in a subject. In another embodiment, the subject mounts an immune response against a pericyte of the solid tumor. In another embodiment, the pericyte is in a vasculature of the solid tumor. Each possibility represents a separate embodiment of the present invention.

In another embodiment, the present invention provides a method of lysing one or more tumor cells expressing HER-2/neu in a subject, comprising administering to the subject a composition comprising a recombinant *Listeria* strain of the present invention, thereby lysing one or more tumor cells in a subject. In one embodiment, tumor lysis is due to cytotoxic T lymphocytes, tumor infiltrating lymphocytes, or a combination thereof, which in one embodiment are tumor-specific.

In another embodiment, the present invention provides a method of inducing an anti-tumor immune response in a subject comprising the step of administering to a subject a composition of the invention. In another embodiment, the composition of the present invention induces the release of antigens associated with cancer. In another embodiment, the composition of the present invention induces the release of antigens associated with a tumor. In another embodiment, the composition of the present invention induces the release of antigens associated with a breast tumor. In another embodiment, killing the vasculature of the tumor caused the release of antigens associated with a tumor which in turn induced a tumor antigen-specific immune response. In another embodiment, killing the vasculature of the tumor caused the release of antigens associated with a tumor which in turn induced a multitude of tumor antigen-specific immune responses. In another embodiment, killing the vasculature of the tumor caused the release of HER-2/neu antigen which in turn induced a HER-2/neu antigen specific immune response.

In another embodiment, the present invention provides that compositions comprising a HMW-MAA fragment induce an immune response against other cancerous antigens. In another embodiment, the present invention provides that compositions comprising a HMW-MAA fragment induce an immune response against other cancerous antigens associated with tumors. In another embodiment, the present invention provides that compositions comprising a HMW-MAA fragment induce an immune response against other cancerous antigens associated with solid tumors. In another embodiment, the present invention provides that compositions comprising a HMW-MAA fragment induce an immune response against other breast cancer antigens. In another embodiment, the present invention provides that compositions comprising a HMW-MAA fragment induce an immune response against other cancerous antigens associated with a breast tumor.

In another embodiment, the immune response to HMW-MAA kills the vasculature of the tumor thus causing the death of the tumor and the release of antigens it contains which then are available to induce a tumor antigen-specific immune response. In another embodiment, the immune response to HMW-MAA enhances the elimination of tumors by killing the vasculature of the tumor, thus causing the death of the tumor and the release of antigens it contains which then are available to induce a tumor antigen-specific immune response. In another embodiment, the immune response to HMW-MAA induces a secondary immune response to antigens released from the tumor. In another embodiment, the immune response to HMW-MAA induces the death of the tumor and subsequently the release of tumor specific antigens which in turn induce a tumor antigen-specific immune. In another embodiment, the present invention provides a method for "epitope spreading" of a tumor.

In one embodiment, methods of the present invention are used to treat, impede, suppress, inhibit, or prevent any of the above-described diseases, disorders, symptoms, or side effects associated with allergy or asthma. In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" or "impeding" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a particular disease or disorder, while in one embodiment, "secondary" refers to a symptom that is derived from or consequent to a primary cause. In one embodiment, the compounds for use in the present invention treat primary or secondary symptoms or secondary complications related to cancer, which in one embodiment, is breast cancer. In another embodiment, "symptoms" may be any manifestation of a disease or pathological condition.

As provided herein, *Listeria* strains expressing HMW-MAA inhibited growth of tumors that did not express HMW-MAA. These findings show that anti-HMW-MAA immune responses inhibit and reverse vascularization of, and thus inhibit growth of, solid tumors. Anti-HMW-MAA vaccines of the present invention were able to exert these effects in spite of the incomplete identity (80%) between HMW-MAA and its mouse homolog, namely mouse chondroitin sulfate proteoglycan ("AN2"). According to this embodiment, anti-HMW-MAA vaccines of the present invention are efficacious for vaccination against any solid tumor expressing HER-2/neu antigen, regardless of its expression of HMW-MAA. In another embodiment, anti-HMW-MAA vaccines of the present invention spread the immune response from HMW-MAA to HER-2/neu antigen. Each possibility represents a separate embodiment of the present invention.

In another embodiment, the present invention provides a method of impeding a vascularization of a solid tumor followed by an anti HER-2/neu immune response in a subject, comprising administering to the subject a composition comprising a recombinant *Listeria* strain of the present invention, thereby impeding a vascularization of a solid tumor followed by an anti HER-2/neu immune response in a subject. In another embodiment, the subject mounts an immune response against a pericyte of the solid tumor. In another embodiment, the subject mounts an immune response against HER-2/neu antigen. In another embodiment, the pericyte is in a vasculature of the solid tumor. Each possibility represents a separate embodiment of the present invention.

The solid tumor that is the target of methods and compositions of the present invention is, in another embodiment, a melanoma. In another embodiment, the tumor is a sarcoma. In another embodiment, the tumor is a carcinoma. In another embodiment, the tumor is a mesothelioma (e.g. malignant mesothelioma). In another embodiment, the tumor is a glioma. In another embodiment, the tumor is a germ cell tumor. In another embodiment, the tumor is a choriocarcinoma.

In another embodiment, the tumor is pancreatic cancer. In another embodiment, the tumor is ovarian cancer. In another embodiment, the tumor is gastric cancer. In another embodiment, the tumor is a carcinomatous lesion of the pancreas. In another embodiment, the tumor is pulmonary adenocarcinoma. In another embodiment, the tumor is colorectal adenocarcinoma. In another embodiment, the tumor is pulmonary squamous adenocarcinoma. In another embodiment, the tumor is gastric adenocarcinoma. In another embodiment, the tumor is an ovarian surface epithelial neoplasm (e.g. a benign, proliferative or malignant variety thereof). In another embodiment, the tumor is an oral squamous cell carcinoma. In another embodiment, the tumor is non small-cell lung carcinoma. In another embodiment, the tumor is an endometrial carcinoma. In another embodiment, the tumor is a bladder cancer. In another embodiment, the tumor is a head and neck cancer. In another embodiment, the tumor is a prostate carcinoma.

In another embodiment, the tumor is anon-small cell lung cancer (NSCLC). In another embodiment, the tumor is a Wilms' tumor. In another embodiment, the tumor is a desmoplastic small round cell tumor. In another embodiment, the tumor is a colon cancer. In another embodiment, the tumor is a lung cancer. In another embodiment, the tumor is an ovarian cancer. In another embodiment, the tumor is a uterine cancer. In another embodiment, the tumor is a thyroid cancer. In another embodiment, the tumor is a hepatocellular carcinoma. In another embodiment, the tumor is a thyroid cancer. In another embodiment, the tumor is a liver cancer. In another embodiment, the tumor is a renal cancer. In another embodiment, the tumor is a kaposis. In another embodiment, the tumor is a sarcoma. In another embodiment, the tumor is another carcinoma or sarcoma. Each possibility represents a separate embodiment of the present invention.

In another embodiment, the tumor is a breast tumor. In one embodiment, the compositions and methods of the present invention are used to treat adenocarcinoma, which in one embodiment, develops in glandular tissue. In one embodiment, the compositions and methods of the present invention are used to treat ductal carcinoma in situ (DCIS), which in one embodiment, develops in the milk ducts and, in another embodiment, is an early form of breast cancer.

In another embodiment, the compositions and methods of the present invention are used to treat invasive ductal carcinoma (IDC), which in one embodiment, is the most common type of breast cancer, develops from DCIS, spreads through the duct walls, and invades the breast tissue. In another embodiment, the compositions and methods of the present invention are used to treat invasive lobular carcinoma, which in one embodiment, originates in the milk glands and accounts for 10-15% of invasive breast cancers. Additional types of breast cancer that may be treated using compositions and methods of the present invention include: Inflammatory (where, in one embodiment, breast tissue is warm and appears red; tends to spread quickly), Medullary carcinoma (which, in one embodiment, originates in central breast tissue), Mucinous carcinoma (where, in one embodiment, is invasive; usually occurs in postmenopausal women), Paget's disease of the nipple (which, in one embodiment, originates in the milk ducts and spreads to the skin of the nipples or areola), Phyllodes tumor (which, in one embodiment, is characterized by a tumor with a leaf-like appearance that extends into the ducts; rarely metastasizes), and Tubular carcinoma (which, in one embodiment, is a small tumor that is often undetectable by palpation). Compositions and methods of the present invention may also be used to treat sarcomas (in one embodiment, cancer of the connective tissue) and lymphomas (in one embodiment, cancer of the lymph tissue) that develop in breast tissue.

In another embodiment, the compositions and methods of the present invention are used to treat breast-related conditions in men, which in one embodiment, is Gynecomastia, Lobular breast cancer (LBC), and Infiltrating (or invasive) ductal carcinoma (IDC), which in one embodiment, is the most common form of male breast cancer and accounts for 80 to 90 percent of all men breast cancer diagnoses. In one embodiment, IDC originates in the duct and breaks into, or invades, the surrounding fatty tissue. In one embodiment, IDC may be contained only within the breast, or, in another embodiment, it can metasticize (spread) to other parts of the body.

In one embodiment, this invention provides compositions and methods for preventing cancer in populations that are predisposed to the cancer or in populations that are at high risk for the cancer, which in one embodiment, may be a population of women with brca1 or brca2 mutations, which population in one embodiment is susceptible to breast cancer.

Each of the above types of cancer represents a separate embodiment of the present invention.

In another embodiment, the present invention provides a method of inducing an immune response against an HMW-MAA-expressing tumor in a subject, comprising administering to the subject a composition comprising a recombinant *Listeria* strain of the present invention, thereby inducing an immune response against an HMW-MAA-expressing tumor. As provided herein, *Listeria* strains expressing HMW-MAA elicited anti-HMW-MAA immune responses and inhibited growth of HMW-MAA-expressing of tumors. In another embodiment, the present invention provides a method of inducing an immune response against an HMW-MAA and HER-2/neu expressing tumor in a subject, comprising administering to the subject a composition comprising a recombinant *Listeria* strain of the present invention, thereby inducing an immune response against an HMW-MAA and HER-2/neu expressing tumor. As provided herein, *Listeria* strains expressing HMW-MAA elicit anti-HMW-MAA and anti-HER-2/neu immune responses and inhibit growth of HMW-MAA-expressing of tumors.

In another embodiment, the present invention provides a method of inducing an anti-HER-2/neu immune response in a subject, said method comprising administering to said subject a composition comprising a recombinant *Listeria* strain expressing HMW-MAA fragment, which in one embodiment is encoded by SEQ ID NO: 23 and a non-HMW-MAA peptide, which in one embodiment, enhances the immunogenicity of the HMW-MAA fragment and in another embodiment is LLO, ActA, PEST sequence or an effective portion thereof, thereby inducing an anti-HER-2/neu immune response in a subject. In another embodiment, the present invention provides a method of inducing an anti-HER-2/neu immune response in a subject, said method comprising administering to said subject a composition comprising a recombinant polypeptide or vector of the present invention.

The HMW-MAA and/or HER-2/neu expressing tumor that is the target of methods and compositions of the present invention is, in another embodiment, a basal cell carcinoma. In another embodiment, the HMW-MAA-expressing tumor is a tumor of neural crest origin. In another embodiment, the HMW-MAA-expressing tumor is an astrocytoma. In another embodiment, the HMW-MAA and/or HER-2/neu expressing tumor is a glioma. In another embodiment, the HMW-MAA and/or HER-2/neu expressing tumor is a neuroblastoma. In another embodiment, the HMW-MAA and/or HER-2/neu expressing tumor is a sarcoma. In another embodiment, the HMW-MAA and/or HER-2/neu expressing tumor is childhood leukemia. In another embodiment, the HMW-MAA and/or HER-2/neu expressing tumor is a lobular breast carcinoma lesion. In another embodiment, the HMW-MAA and/or HER-2/neu expressing tumor is a melanoma. In another embodiment, the HMW-MAA and/or HER-2/neu expressing tumor is any other HMW-MAA and/or HER-2/neu expressing tumor. Each possibility represents a separate embodiment of the present invention.

In another embodiment, the present invention provides a method of inducing an immune response against a pericyte and/or HER-2/neu antigen in a subject, comprising administering to the subject a composition comprising a recombinant *Listeria* strain of the present invention, thereby inducing an immune response against a pericyte and/or HER-2/neu antigen. As provided herein, *Listeria* strains expressing HMW-MAA inhibited growth of solid tumors expressing HER-2/neu antigen, even those that did not express HMW-MAA. These findings demonstrate inhibition of vascularization via induction of immune responses against tumor-vascular associated pericytes.

In another embodiment, the present invention provides a method of impeding a growth and/or delaying progression of a HMW-MAA and/or HER-2/neu-expressing tumor in a subject, comprising administering to the subject a composition comprising a recombinant *Listeria* strain of the present invention, thereby impeding a growth and/or delaying progression of a HMW-MAA and/or HER-2/neu-expressing tumor in a subject. In another embodiment, the subject mounts an immune response against the HMW-MAA and/or HER-2/neu-expressing tumor. Each possibility represents a separate embodiment of the present invention.

In another embodiment, the present invention provides a method of treating a HMW-MAA and/or HER-2/neu-expressing tumor in a subject, comprising administering to the subject a composition comprising a recombinant *Listeria* strain of the present invention, thereby treating a HMW-MAA and/or HER-2/neu-expressing tumor in a subject. In another embodiment, the subject mounts an immune response against the HMW-MAA and/or HER-2/neu-expressing tumor. Each possibility represents a separate embodiment of the present invention.

In another embodiment, the present invention provides a method of treating a breast cancer in a subject, whereby said breast cancer is associated with expression of HER-2/neu antigen in said subject, said method comprising administering to said subject a composition comprising a recombinant *Listeria* or recombinant polypeptide, or recombinant vector of the present invention, whereby said subject mounts an immune response against said HER-2/neu-expressing tumor, thereby treating a breast cancer in a subject.

In another embodiment, the present invention provides a method of inhibiting a breast cancer in a subject, whereby said breast cancer is associated with expression of HER-2/neu antigen in said subject, said method comprising administering to said subject a composition comprising a recombinant *Listeria* or recombinant polypeptide, or recombinant vector of the present invention, whereby said subject mounts an immune response against said HER-2/neu-expressing tumor, thereby inhibiting a breast cancer in a subject.

In another embodiment, the present invention provides a method of suppressing a breast cancer in a subject, whereby said breast cancer is associated with expression of HER-2/neu antigen in said subject, said method comprising administering to said subject a composition comprising a recombinant *Listeria* or recombinant polypeptide, or recombinant vector of the present invention, whereby said subject mounts an immune response against said HER-2/neu-expressing tumor, thereby suppressing a breast cancer in a subject.

In another embodiment, the present invention provides a method of delaying the onset, reducing the incidence, increasing the latency to relapse, decreasing the latency to remission, decreasing the severity, improving the symptoms of a breast cancer in a subject, whereby said breast cancer is associated with expression of HER-2/neu antigen in said subject, said method comprising administering to said subject a composition comprising a recombinant *Listeria* or recombinant polypeptide, or recombinant vector of the present invention, whereby said subject mounts an immune response against said HER-2/neu-expressing tumor, thereby delaying the onset, reducing the incidence, increasing the latency to relapse, decreasing the latency to remission, decreasing the severity, improving the symptoms of a breast cancer in a subject.

In another embodiment, the present invention provides a method of inducing an anti-tumor immune response in a subject comprising the step of administering to said subject a composition comprising a recombinant *Listeria* or recombinant polypeptide, or recombinant vector of the present invention, whereby said composition kills the vasculature of said tumor and induces the release of a tumor antigen, thereby inducing an anti-tumor immune response. In one embodiment, said tumor is a breast tumor, which in one embodiment, is associated with breast cancer.

The recombinant *Listeria* strain of the present invention utilized in methods of the present invention comprises, in another embodiment, a recombinant polypeptide of the present invention. In another embodiment, the recombinant *Listeria* strain comprises a recombinant nucleotide molecule of the present invention. In another embodiment, the recombinant *Listeria* strain is any recombinant *Listeria* strain described or enumerated above. Each possibility represents a separate embodiment of the present invention.

In another embodiment, the present invention provides a method of inducing an anti-HMW-MAA and/or anti-HER-2/neu immune response in a subject, comprising administering to the subject a composition comprising a recombinant polypeptide of the present invention, thereby inducing an anti-HMW-MAA and/or anti-HER-2/neu immune response in a subject.

In another embodiment, the present invention provides a method of inducing an immune response against an HMW- MAA and/or HER-2/neu-expressing tumor in a subject, comprising administering to the subject a composition comprising a recombinant polypeptide of the present invention, thereby inducing an immune response against an HMW-MAA and/or HER-2/neu-expressing tumor.

In another embodiment, the present invention provides a method of inducing an immune response against a pericyte and/or HER-2/neu antigen in a subject, comprising administering to the subject a composition comprising a recombinant polypeptide of the present invention, thereby inducing an immune response against a pericyte and/or HER-2/neu antigen.

In another embodiment, the present invention provides a method of impeding a growth and/or delaying progression of a solid tumor expressing HER-2/neu in a subject, comprising administering to the subject a composition comprising a recombinant polypeptide of the present invention, thereby impeding a growth and/or delaying progression of a solid tumor expressing HER-2/neu in a subject. In another embodiment, the subject mounts an immune response against a pericyte and/or HER-2/neu of the solid tumor. In another embodiment, the pericyte is in a vasculature of the solid tumor. Each possibility represents a separate embodiment of the present invention.

In another embodiment, the present invention provides a method of treating a solid tumor in a subject, comprising administering to the subject a composition comprising a recombinant polypeptide of the present invention, thereby treating a solid tumor in a subject. In another embodiment, the subject mounts an immune response against a pericyte and/or HER-2/neu of the solid tumor. In another embodiment, the pericyte is in a vasculature of the solid tumor. Each possibility represents a separate embodiment of the present invention.

In another embodiment, the present invention provides a method of impeding a vascularization of a solid tumor in a subject, comprising administering to the subject a composition comprising a recombinant polypeptide of the present invention, thereby impeding a vascularization of a solid tumor in a subject. In another embodiment, the subject mounts an immune response against a pericyte of the solid tumor. In another embodiment, the pericyte is in a vasculature of the solid tumor. Each possibility represents a separate embodiment of the present invention.

In another embodiment, the present invention provides a method of impeding a growth and/or delaying progression of a HMW-MAA and/or HER-2/neu-expressing tumor in a subject, comprising administering to the subject a composition comprising a recombinant polypeptide of the present invention, thereby impeding a growth and/or delaying progression of a HMW-MAA and/or HER-2/neu-expressing tumor in a subject. In another embodiment, the subject mounts an immune response against the HMW-MAA and/or HER-2/neu-expressing tumor. Each possibility represents a separate embodiment of the present invention.

In another embodiment, the present invention provides a method of treating a HMW-MAA and/or HER-2/neu-expressing tumor in a subject, comprising administering to the subject a composition comprising a recombinant polypeptide of the present invention, thereby treating a HMW-MAA and/or HER-2/neu-expressing tumor in a subject. In another embodiment, the subject mounts an immune response against the HMW-MAA and/or HER-2/neu-expressing tumor. Each possibility represents a separate embodiment of the present invention.

In other embodiments, the recombinant polypeptide of any of the methods described above have any of the characteristics of a recombinant polypeptide of compositions of the present invention. Each characteristic represents a separate embodiment of the present invention.

In another embodiment of methods of the present invention, a vaccine comprising a recombinant *Listeria* strain of the present invention is administered. In another embodiment, an immunogenic composition comprising a recombinant *Listeria* strain of the present invention is administered. In another embodiment, a vaccine comprising a recombinant polypeptide of the present invention is administered. In another embodiment, an immunogenic composition comprising a recombinant polypeptide of the present invention is administered. Each possibility represents a separate embodiment of the present invention.

In another embodiment, the target pericyte of methods and compositions of the present invention is an activated pericyte. In another embodiment, the target pericyte is any other type of pericyte known in the art. Each possibility represents a separate embodiment of the present invention.

In another embodiment, a method or immunogenic composition of methods and compositions of the present invention induces a cell-mediated immune response. In another embodiment, the immunogenic composition induces a predominantly cell-mediated immune response. In another embodiment, the immunogenic composition induces a predominantly Th1-type immune response. Each possibility represents a separate embodiment of the present invention.

In another embodiment, the immune response elicited by methods of the present invention is a cell-mediated immune response. In another embodiment, the immune response is a T-cell-mediated immune response. Each possibility represents a separate embodiment of the present invention.

The T cell-mediated immune response induced by methods and compositions of the present invention comprises, in another embodiment, a CTL. In another embodiment, the T cell involved in the T cell-mediated immune response is a CTL. Each possibility represents a separate embodiment of the present invention.

In another embodiment, the T cell-mediated immune response comprises a T helper cell. In another embodiment, the T cell involved in the T cell-mediated immune response is a T helper cell. Each possibility represents a separate embodiment of the present invention.

In another embodiment of methods of the present invention, the subject is immunized with an immunogenic composition, vector, or recombinant peptide of the present invention. In another embodiment, the subject is contacted with the immunogenic composition, vector, or recombinant peptide. Each possibility represents a separate embodiment of the present invention.

In another embodiment, the present invention provides a method of inhibiting adhesion of a cancer cell to the extracellular matrix, comprising inducing an anti-HMW-MAA and/or anti-HER-2/neu immune response by a method of the present invention, thereby inhibiting adhesion of a cancer cell to the extracellular matrix. In another embodiment, the cancer cell is a melanoma cell. Each possibility represents a separate embodiment of the present invention.

In another embodiment, the present invention provides a method of inhibiting metastasis of a tumor, comprising inducing an anti-HMW-MAA and/or anti-HER-2/neu immune response by a method of the present invention, thereby inhibiting metastasis of a tumor. In another embodiment, the tumor is a melanoma tumor. In another embodiment, the tumor is a breast tumor. In another embodiment, the tumor is a NT-2 tumor. Each possibility represents a separate embodiment of the present invention.

In another embodiment, the present invention provides a method of inhibiting migration of a cancer cell, comprising inducing an anti-HMW-MAA and/or anti-HER-2/neu immune response by a method of the present invention, thereby inhibiting migration of a cancer cell. In another embodiment, the cancer cell is a melanoma cell. Each possibility represents a separate embodiment of the present invention.

In another embodiment, the present invention provides a method of inhibiting proliferation of cells in a tumor, comprising inducing an anti-HMW-MAA and/or anti-HER-2/neu immune response by a method of the present invention, thereby inhibiting proliferation of cells in a tumor. In another embodiment, the tumor is a melanoma tumor. Each possibility represents a separate embodiment of the present invention.

In another embodiment, the present invention provides a method of reducing invasiveness of a tumor, comprising inducing an anti-HMW-MAA and/or anti-HER-2/neu immune response by a method of the present invention, thereby reducing invasiveness of a tumor. In another embodiment, the tumor is a melanoma tumor. In another embodiment, anti-HMW-MAA and/or anti-HER-2/neu immune responses inhibit formation of HMW-MAA-MT3-MMP (membrane type metalloproteinases) complexes. In another embodiment, inhibition of formation of these complexes inhibits degradation of type I collagen by melanoma cells. Each possibility represents a separate embodiment of the present invention.

In another embodiment, the present invention provides a method of inhibiting conversion of plasminogen into plasmin in the vicinity of a tumor, comprising inducing an anti-HMW-MAA and/or anti-HER-2/neu immune response by a method of the present invention, thereby inhibiting conversion of plasminogen into plasmin in the vicinity of a tumor. In another embodiment, the tumor is a melanoma tumor. In another embodiment, the tumor is a breast tumor. In another embodiment, inhibiting plasmin release inhibits, in turn, degradation of the extracellular matrix (ECM). Each possibility represents a separate embodiment of the present invention.

In another embodiment, the present invention provides a method of inhibiting sequestration of angiostatin in the vicinity of a tumor, comprising inducing an anti-HMW-MAA immune response by a method of the present invention, thereby inhibiting sequestration of angiostatin in the vicinity of a tumor. In another embodiment, the tumor is a melanoma tumor. Each possibility represents a separate embodiment of the present invention.

In another embodiment, a peptide of the present invention is homologous to a peptide enumerated herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" or "homologous" refers to a sequence sharing greater than 70% identity with a second sequence. In another embodiment, "homology" refers to a sequence sharing greater than 72% identity with a second sequence. In another embodiment, "homology" refers to a sequence sharing greater than 75% identity with a second sequence. In another embodiment, "homology" refers to a sequence sharing greater than 78% identity with a second sequence. In another embodiment, "homology" refers to a sequence sharing greater than 80% identity with a second sequence. In another embodiment, "homology" refers to a sequence sharing greater than 82% identity with a second sequence. In another embodiment, "homology" refers to a sequence sharing greater than 83% identity with a second sequence. In another embodiment, "homology" refers to a sequence sharing greater than 85% identity with a second sequence. In another embodiment, "homology" refers to a sequence sharing greater than 87% identity with a second sequence. In another embodiment, "homology" refers to a sequence sharing greater than 88% identity with a second sequence. In another embodiment, "homology" refers to a sequence sharing greater than 90% identity with a second sequence. In another embodiment, "homology" refers to a sequence sharing greater than 92% identity with a second sequence. In another embodiment, "homology" refers to a sequence sharing greater than 93% identity with a second sequence. In another embodiment, "homology" refers to a sequence sharing greater than 95% identity with a second sequence. In another embodiment, "homology" refers to a sequence sharing greater than 96% identity with a second sequence. In another embodiment, "homology" refers to a sequence sharing greater than 97% identity with a second sequence. In another embodiment, "homology" refers to a sequence sharing greater than 98% identity with a second sequence. In another embodiment, "homology" refers to a sequence sharing greater than 99% identity with a second sequence. In another embodiment, "homology" refers to identity to one of SEQ ID No: 1-14 of 100% identity with a second sequence. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

Figure 16:
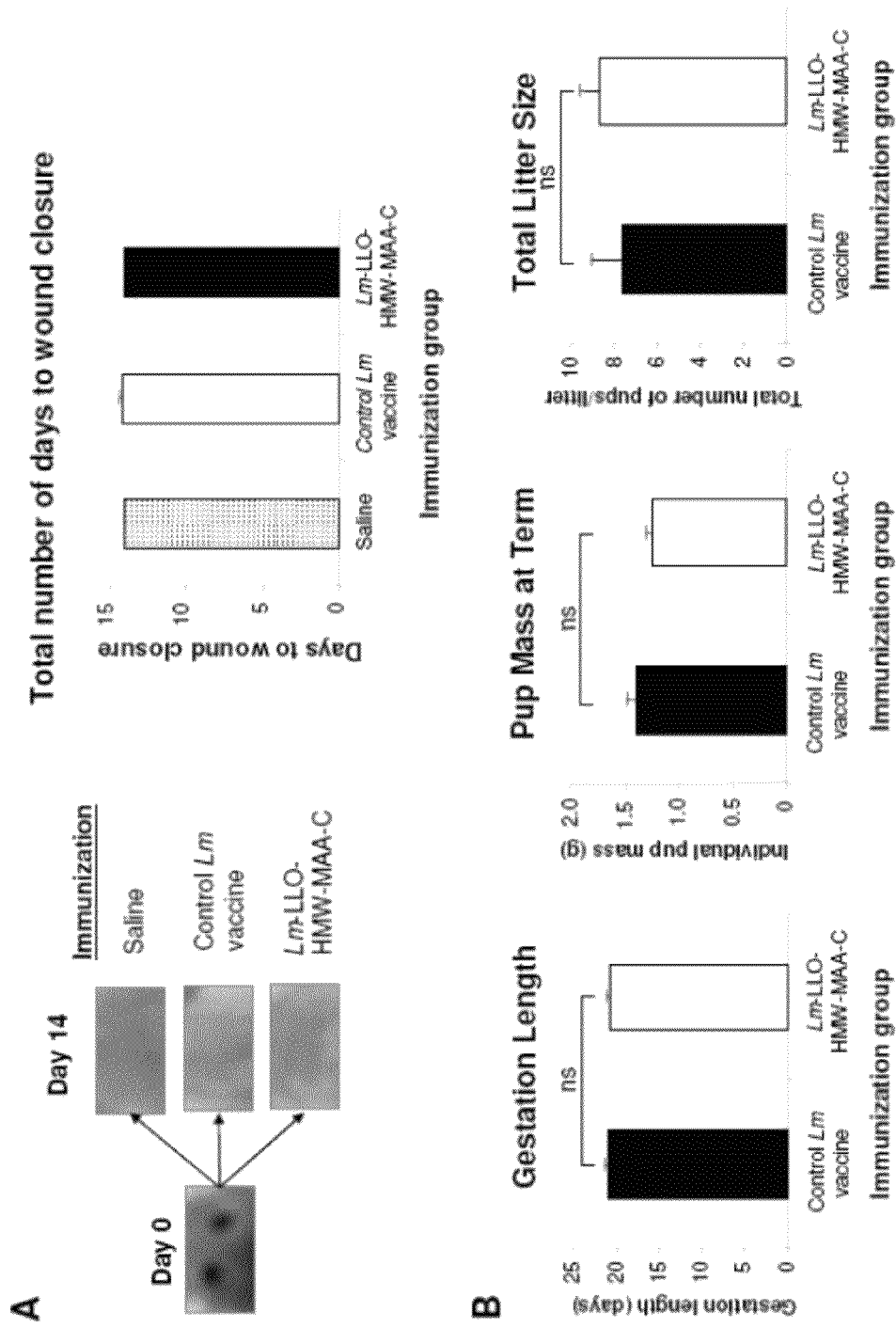
FIG. 16. Lm-LLO-HMWMAA-C vaccine does not reduce wound healing ability of immunized mice nor affect pregnancy or fertility. A, FVB/N female 8 week old, age-matched mice were immunized three times, one week apart with a control Lm vaccine or Lm-LLO-HMWMAA-C or saline alone. On the fourth week mice were shaved and 3 mm punctures through the skin were done on the upper back of anesthetized mice. A total of 5 mice were tested per group and a representative mouse from each group is shown on day 0 and 14 days later. B, FVB/N female mice were immunized three times, one week apart with either a control Lm vaccine (n=4) or Lm-LLO-HMWMAA-C (n=3) and then mated with syngeneic males. Vaginal plug denoted time of coitus and the gestation length, individual pup mass, and the total number of pups per litter were measured. Graphs show mean±SEM. ns, P>0.05, t test.

In one embodiment, the data presented herein demonstrate the safety of the Lm-HMW-MAA vaccine (FIG. 16). In another embodiment, the data presented herein demonstrate the lack of toxicity of the Lm-HMW-MAA vaccine described herein (FIG. 16). In another embodiment, the data presented herein demonstrate the lack of teratogenicity of the Lm-HMW-MAA vaccine described herein (FIG. 16).

In one embodiment, a composition of the present invention leads to an infiltration of CD8+ T cells around blood vessels and in the stroma of tumors from immunized mice. In one embodiment, the presence of tumor infiltrating lymphocytes correlates with clinical responses in cancer immunotherapy. As described hereinbelow, despite their effect on vasculature, compositions of the present invention do not lead to toxicity such as wound healing, pregnancy or fertility problems associated with blood vessel damage in mice immunized with Lm-HMW-MAA-C.

In another embodiment, compositions of the present invention may be used in combination with other therapies for treating tumors. In another embodiment, compositions of the present invention may be used in combination with metronomic therapies to reduce tumor angiogenesis. In one embodiment, compositions of the present invention may be used in combination with an inhibitor of PDGFR signaling, which in one embodiment, reduces pericyte counts, or in another embodiment, with a VEGFR inhibitor. In one embodiment, targeting pericytes in the tumor stroma might cause a certain degree of vasculitis that could promote the infiltration of the tumor by specific T cells to tumor-associated antigens and improve the efficacy of cancer immunotherapies. In another embodiment, compositions of the present invention may be used in combination with active antibody-mediated therapies, which in one embodiment, target HMW-MAA.

In one embodiment, a "vaccine" is a composition that induces an immune response in a host. In one embodiment, the immune response is to a particular antigen or to a particular epitope on the antigen. In one embodiment, the vaccine may be a peptide vaccine, in another embodiment, a DNA vaccine. In another embodiment, the vaccine may be contained within and, in another embodiment, delivered by, a cell, which in one embodiment is a bacterial cell, which in one embodiment, is a *Listeria*. In one embodiment, a vaccine may prevent a subject from contracting or developing a disease or condition, wherein in another embodiment, a vaccine may be therapeutic to a subject having a disease or condition. Therapeutic and prophylactic effects of the compositions of the present invention are described hereinabove. In one embodiment, a vaccine of the present invention comprises a composition of the present invention and an adjuvant, cytokine, chemokine, or combination thereof.

Pharmaceutical Compositions and Methods of Administration

"Pharmaceutical composition" refers, in another embodiment, to a therapeutically effective amount of the active ingredient, i.e. the recombinant peptide or vector comprising or encoding same, together with a pharmaceutically acceptable carrier or diluent. A "therapeutically effective amount" refers, in another embodiment, to that amount which provides a therapeutic effect for a given condition and administration regimen.

The pharmaceutical compositions containing the active ingredient can be, in another embodiment, administered to a subject by any method known to a person skilled in the art, such as parenterally, transmucosally, transdermally, intramuscularly, intravenously, intra-dermally, subcutaneously, intra-peritonealy, intra-ventricularly, intra-cranially, intra-vaginally, or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the recombinant peptide or vector is prepared and applied as a solution, suspension, or emulsion in a physiologically acceptable diluent with or without a pharmaceutical carrier.

In another embodiment, the active ingredient is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In another embodiment, the pharmaceutical compositions provided herein are controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Experimental Details Section

Mice. Female C57BL/6, BALB/c and FVB/N mice were purchased from Charles River Laboratories. A breeder pair of HLA-A2/K$^b$ was generously provided by Dr. L. Sherman (The Scripps Research Institute, La Jolla, Calif.). These mice were maintained and bred in the animal core facility at the University of Pennsylvania. The FVB/N HER-2/neu transgenic mice (Muller, Cancer Metastasis Rev 1991; 10:217-27) were housed and bred at the Veterans' Administration Hospital affiliated with the University of Pennsylvania. Mice were six to eight weeks-old at the start of the experiments, which were done in accordance with regulations by the Institutional Animal Care and Use Committee of the University of Pennsylvania.

Antibodies. The anti-HMW-MAA mAb VT80.12 has been previously described (Chen Z J, Ferrone S. Comparison of the binding parameters to melanoma cells of antihuman high molecular weight-melanoma associated antigen (HMW-MAA) monoclonal antibodies (mAb) and syngeneic anti-anti-idiotypic (anti-anti-id) mAb. Ann NY Acad Sci 1993; 690:398-401). Goat anti-mouse IgG-PE, anti-CD8b.2-FITC, anti-IFN-γ-PE, anti-mouse CD31-FITC, anti-mouse CD8α-PE, rat IgG2a and rat IgG2b isotype controls were purchased from BD Biosciences. Anti-α-Smooth Muscle (αSMA)-Cy3 and anti-FLAG M2 monoclonal antibodies were purchased from Sigma. Secondary anti-rabbit Alexa Fluor 488 was purchased from Invitrogen and anti-rat NG2 from Chemicon. The anti-CD4 mAb GK1.5, anti-CD8 mAb 2.43 and anti-CD25 mAb PC61 were purified using protein G sepharose columns (Amersham Biosciences).

Flow cytometry. Cells were harvested, washed in FACS buffer (PBS-2% FBS) and Fc receptors blocked with 2.4G2 hybridoma supernatant. After washing, cells were resuspended in 50 μl of FACS buffer containing the appropriate antibodies and incubated at 4° C. in the dark for 30 minutes. Cells were washed twice and when necessary incubated with a secondary antibody. Otherwise, cells were fixed in 2% formaldehyde and analyzed using a FACS Calibur cytometer and CellQuest Pro software (BD Biosciences).

Cell lines. Cell culture media and supplements were purchased from Gibco (Invitrogen). B16F10 cells were maintained in DMEM and RENCA and J774 cells in RPMI 1640. Media was supplemented with 10% FBS, 10 mM HEPES buffer, 2 mM L-glutamine, 0.1 mM non-essential amino acids, 1 mM sodium pyruvate and 50 μg/ml of gentamicin. The NT-2 cell line was maintained in RPMI 1640 supplemented with 20% FBS, 10 mM HEPES buffer, 2 mM L-glutamine, 0.1 mM non-essential amino acids, 1 mM sodium pyruvate, 20 μg/ml of insulin, 100 U/ml of penicillin and 100 μg/ml of streptomycin. All cell cultures were kept at 37° C. and 5% $CO_2$. B16F10 cells were transfected with a pcDNA3.1$^+$ plasmid containing the full-length HMW-MAA cDNA sequence (Peng L, Ko E, Luo W, Wang X, Shrikant P A, Ferrone S. CD4-dependent potentiation of a high molecular weight-melanoma-associated antigen-specific CTL response elicited in HLA-A2/Kb transgenic mice. J Immunol 2006; 176:2307-15), using lipofectamine 2000 (Invitrogen), as recommended by the manufacturer. Stable transfected cells were maintained in medium supplemented with 1 mg/ml of G418 and single clones were isolated using limiting dilution. Individual clones were screened for HMW-MAA expression by flow cytometry using the monoclonal antibody VT80.12.

Construction of Lm-LLO-HMW-MAA-C vaccine. A fragment corresponding to HMW-MAA residues 2160 to 2258 was amplified by PCR using the primers 5'-TGCTCGAGGCCACTGAGCCTTACAATGCTGCC-3' (forward primer, XhoI site underlined) and 5'-CCCGGGTTACTACTTATCGTCGTCATCCTTGTAATC-CTGGACGTCATGCTTGCCCG-3' (reverse primer, XmaI site underlined, stop codon in bold and Flag sequence in italics). The PCR product was ligated into pCR2.1-TOPO plasmid (Invitrogen), confirmed by sequencing and subsequently excised by double digestion with XhoI and XmaI (New England Biolabs). The fragment was ligated into a pGG55-based plasmid downstream and fused to a gene encoding for the first 441 residues of the LLO protein, whose expression is driven by the hly promoter. The construction of the pGG55 has been described in details elsewhere (Gunn G R, Zubair A, Peters C, Pan Z K, Wu T C, Paterson Y. Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16. J Immunol 2001; 167:6471-9). The resultant plasmid was electroporated into the PrfA-defective Lm strain XFL-7 (kindly provided by Hao Shen, University of Pennsylvania, Philadelphia, Pa.), which is derived from the Lm strain 10403S. Positive clones were selected on Brain Heart Infusion (BHI, Difco) plates supplemented with 34 μg/ml of chloramphenicol and 250 μg/ml of streptomycin. The resultant strain was named Lm-LLO-HMW-MAA-C, which was subsequently passaged twice in vivo as previously described (Peters C, Paterson Y. Enhancing the immunogenicity of bioengineered *Listeria monocytogenes* by passaging through live animal hosts. Vaccine 2003; 21:1187-94.

Effect of Lm-LLO-HMW-MAA-C on tumor growth. Mice were given s.c. $2 \times 10^5$ of B16F10-HMW-MAA, B16F10 or RENCA tumor cells on the flank in 0.2 ml of PBS. On day 3 after tumor inoculation, mice were immunized i.p. with $2.5 \times 10^7$ CFU of Lm-LLO-HMW-MAA-C. This dose was determined as one-tenth of the minimum dose observed to have adverse effects on mice and it was used in all experiments. In the NT-2 model, mice were given $1 \times 10^6$ tumor cells and immunized 7 days later with Lm-LLO-HMW-MAA-C. The FVB/N HER-2/neu transgenic mice received the first dose of vaccine when 6-8-weeks old. Immunizations were repeated weekly totaling three doses of the vaccine in all experiments. In the control groups, mice received either PBS or an equivalent dose of an irrelevant Lm vaccine (Lm-LLO-E7 or Lm-LLO-NY-ESO-$1_{101-156}$). Tumors were measured every 2-3 days with calipers and the shortest and longest surface diameters were recorded for each individual tumor. Mice were sacrificed when they developed open wounds or tumors reached 20 mm in diameter. Tumor-free surviving mice challenged with B16F10-HMW-MAA were rechallenged in the opposite flank with the same cell line 7-weeks after the first inoculation.

In vivo cell depletions. For CD4 and CD8 in vivo depletions, 500 μg of GK1.5 and 2.43 antibodies, respectively, were given i.p. on days 1, 2, 6 and 9. The control groups received either an anti-p-galactosidase antibody or were left untreated. For CD25 depletion, 500 μg of PC61 was given i.p. on days 0 and 2. These antibodies were tested and confirmed to induce depletion of the target cells by flow cytometry (data not shown).

Transfer of anti-tumor immunity (Winn assay). C57BL/6 mice were injected twice at a one-week interval with Lm-HMW-MAA-C. Control mice were left untreated. One-week after the last immunization, mice were sacrificed and the spleens harvested. CD8.sup.+T cells were enriched from the splenocyte suspension by negative magnetic selection (DYNAL®. Mouse CD8 Cell Negative Isolation Kit, Invitrogen) and comprised 85% of the total cells as assessed by flow-cytometry. CD8$^+$T cells either from naive or Lm-HMW-MAA-C immunized mice were mixed in PBS with B16F10-HMW-MAA at a ratio of 10:1 and 0.2 ml of the cell suspension, containing $2 \times 10^5$ tumor cells and $2 \times 10^6$ CD8$^+$T cells, was inoculated s.c. on the flank of naive mice. Tumors were measured every 2 days with a caliper and the size recorded as the mean tumor diameter.

Synthetic peptide. The HLA-A2-binding synthetic peptide LILPLLFYL (SEQ ID NO: 45), which corresponds to HMW-MAA residues 2238 to 2246, was purchased from EZBiolab.

Murine IFN-γ assays to detect antigen-specific CD8$^+$ T-cells. Spleens from immunized mice were harvested one-week after last immunization. After lysing red blood cells, splenocytes were stimulated with 1 μM of the HMW-MAA$_{2238-2246}$ peptide and IFN-γ production detected by either ELISpot or intracellular cytokine staining. ELISpots were performed according to the manufacturer instructions (Mabtech), and spot forming cells (SFC) counted using a dissecting microscope. Intracellular cytokine staining for IFN-γ was done as previously described (Peters C, Paterson Y. Enhancing the immunogenicity of bioengineered *Listeria monocytogenes* by passaging through live animal hosts. Vaccine 2003; 21:1187-94). Data was collected using a FACS Calibur cytometer and analyzed using CellQuest Pro software. Cells were gated on CD8$^{high}$ and analyzed for intracellular IFN-γ.

Immunofluorescence. On day 84 post tumor inoculation, mice were sacrificed and the NT-2 tumors were surgically excised, cryopreserved in OCT freezing medium and cryo-sectioned for 8-10 micron thick sections. For immunofluorescence, samples were thawed and fixed using 4% formalin. After blocking (2.4G2 conditioned medium/10% FBS/5% normal rat serum and normal mouse serum), sections were stained with primary antibodies in blocking solution in a humidified chamber at 37° C. for 1 hour. Samples were stained with secondary antibody following the same procedure as for primary staining. DAPI (Invitrogen) staining was performed according to manufacturer instructions. Intracellular stains (αSMA) were done in PBS/0.1% tween/1% BSA solution. Slides were cover-slipped using Biomeda mounting solution (Biomeda) with anti-fading agents, set for 24 hours and kept at 4° C. until imaging using Spot Image Software (2006) and BX51 series Olympus fluorescent microscope. Images were merged using Spot Image Software and quantitation was performed after an ROI was gated using Image Pro Software (2006). All images are a merged series of three different channels captured for same exposure time.

Evaluation of possible toxicity associated with inhibition of angiogenesis. Six to eight week old FVB/N female mice were immunized three consecutive times weekly with either a control Lm vaccine or Lm-LLO-HMWMAA-C. On the fourth week, safety studies were conducted. For pregnancy and fertility, 5 mice per group were allowed to mate with individual housed males. Coitus was monitored and confirmed by the presence of a vaginal plug. Time to gestation, pup birth weight and total litter size were measured. The wound healing assay utilized in this study was done according to previously described methods used in antiangiogenesis studies (Niethammer A G, Xiang R, Becker J C, et al. A DNA vaccine against VEGF receptor 2 prevents effective angiogenesis and inhibits tumor growth. Nat Med 2002; 8:1369-75). Briefly, mice were anesthetized, hair removed and skin-cleaned with an aseptic wipe. Two circular 3 mm in diameter wounds were punched from the skin using a sterile skin biopsy tool (Acuderm). Wounds were not treated and no infection was observed. Average time to wound closure was monitored and considered complete when a scar was formed without any visible scab left.

Statistical analysis. Data were analyzed using either the non-parametric Mann-Whitney test or the parametric t test when appropriated. The log-rank test was used for survival data. All statistical analyses were done with the SPSS15.0 software. Statistical significance was based on a value of $P \leq 0.05$.

Example 1

Construction of LLO-HMW-MAA Constructs and *Listeria* Strains Expressing Same LLO-HMW-MAA constructs were created as follows:

pGG-55, the precursor of the LLO-HMW-MAA constructs, was created from pAM401, a shuttle vector able to replicate in both gram-negative and gram-positive bacteria (Wirth R et al, J Bacteriol, 165: 831, 1986). pAM401 contains a gram-positive chloramphenicol resistance gene and gram negative tetracycline resistance determinant. In pGG-55, the hly promoter drives the expression of the first 441 AA of the hly gene product, (lacking the hemolytic C-terminus, having the sequence set forth in SEQ ID No: 3), which is joined by the XhoI site to the E7 gene, yielding a hly-E7 fusion gene that is transcribed and secreted as LLO-E7.

Generation of pGG-55: A fusion of a listeriolysin fragment to E7 ("LLO-E7") and the pluripotential transcription factor prfA were subcloned in pAM401 as follows: The DNA fragment encoding the first 420 AA of LLO and its promoter and upstream regulatory sequences was PCR amplified with LM genomic DNA used as a template and ligated into pUC19. PCR primers used were 5'-GGCCCGGGCCCCCTC-CTTTGAT-3' (SEQ ID No: 17) and 5'-GGTCTAGATCAT-AATTTACTTCATCC-3' (SEQ ID No: 18). E7 was amplified by PCR using the primers 5'-GG CTCGAGCATGGAGATACACC-3' (SEQ ID No: 19; XhoI site is underlined) and 5'-GGGG ACTAGTTTATGGTTTCTGAGAACA-3' (SEQ ID No: 20; SpeI site is underlined) and ligated into pCR2.1 (Invitrogen, San Diego, Calif.). E7 was excised from pCR2.1 by XhoI/SpeI digestion and subsequently ligated as an in-frame translational fusion into pUC19-hly downstream of the hemolysin gene fragment. The fusion was then subcloned into the multilinker of pAM401. The prfA gene was then subcloned into the SalI site of the resulting plasmid, yielding pGG-55 (FIG. 1).

pGG34A, B and C were created from pGG-55 as follows:

HMW-MAA fragments A, B, and C (encoding AA 360-554, 701-1130, and 2160-2258, respectively, FIG. 1) have the following sequences:

HMW-MAA-A:

(SEQ ID No: 21)
Ttcaatggccagaggcgggggctgcgggaagctttgctgacgcgcaacat
ggcagccggctgcaggctggaggaggaggagtatgaggacgatgcctatg
gacattatgaagctttctccaccctggcccctgaggcttggccagccatg
gagctgcctgagccatgcgtgcctgagccagggctggcctcctgtctttgc
caatttcacccagctgctgactatcagcccactggtggtggccgaggggg
gcacagcctggcttgagtggaggcatgtgcagcccacgctggacctgatg
gaggctgagctgcgcaaatcccaggtgctgttcagcgtgacccgagggc
acgccatggcgagctcgagctggacatcccgggagcccaggcacgaaaaa
tgttcaccctcctggacgtggtgaaccgcaaggcccgcttcatccacgat
ggctctgaggacacctccgaccagctggtgctggaggtgtcggtgacggc
tcgggtgccatgccctcatgccttcggaggggccaaacatacctcctgc
ccatccaggtcaaccctgtcaatgacccaccccac.

HMW-MAA-B:

(SEQ ID No: 22)
Gtccgcgtcactggggcctgcagtttggggagctgcagaaacacgggc
aggtggggtggagggtgctgagtggtgggccacacaggcgttccaccagc
gggatgtggagcagggccgcgtgaggtacctgagcactgacccacagcac
cacgcttacgacaccgtggagaacctggccctggaggtgcaggtgggcca
ggagatcctgagcaatctgtccttcccagtgaccatccagagagccactg
tgtggatgctggcgctggagccactgcacactcagaacaccagcaggag
accctcaccacagcccacctggaggccaccctggaggaggcaggcccaag
cccccaaccttccattatgaggtggttcaggctcccaggaaaggcaacc
ttcaactacagggcacaaggctgtcagatggccagggcttcacccaggat
gacatacaggctggccgggtgaccttcaacagtgccagctacctctatga
ggtcatggagcggccccgccatgggaggttggcttggcgtgggacacagg
acaagaccactatggtgacatccagagcagtggtgacatggcctgggagg
aggtacggggtgtcttccgagtggccatccagcccgtgaatgaccacgcc
cctgtgcagaccatcagccggatcttccatgtggcccggggtgggcggcg
gctgctgactacagacgacgtggccttcagcgatgctgactcgggctttg
ctgacgcccagctggtgcttacccgcaaggacctcctctttggcagtatc
gtggccgtagatgagcccacgcggcccatctaccgcttcacccaggagga
cctcaggaagaggcgagtactgttcgtgcactcaggggctgaccgtggct
ggatccagctgcaggtgtccgacgggcaacaccaggccactgcgctgctg
gaggtgcaggcctcggaacctacctccgtgtggcc.

HMW-MAA-C:

(SEQ ID No: 23)
Gccactgagccttacaatgctgcccggccctacagcgtggccctgctcag
tgtccccgaggccgccggacggaagcagggaagccagagagcagcaccc
ccacaggcgagccaggccccatggcatccagccctgagcccgctgtggcc
aagggaggcttcctgagcttccttgaggccaacagacgtccag.

The fragments were amplified using the following primers. The XhoI sites in the forward primers and XmaI sites (A and C) or SpeI site (B) in the reverse primers are underlined:

Fragment A:-forward primer (SEQ ID No: 24)
TCCTCGAGGTCAATGGCCAGAGGCGGGGG.
Reverse:

(SEQ ID No: 25)
CCCGGGTTACTACTTATCGTCGTCATCCTTGTAATCGTGGGGTGGGTCAT
TGAC.

Fragment B: forward:

(SEQ ID No: 26)
GCCTCGAGTTCCGCGTCACTGGGGCCCTG.
Reverse:

(SEQ ID No: 27)
ACTAGTTTACTACTTATCGTCGTCATCCTTGTAATCGGCCACACGGAGGT
AGGGTTC.

Fragment C: Forward:

(SEQ ID No: 28)
TGCTCGAGGCCACTGAGCCTTACAATGCTGCC.
Reverse:

(SEQ ID No: 29)
CCCGGGTTACTACTTATCGTCGTCATCCTTGTAATCCTGGACGTCATGCT
TGCCCG.

Fragments A-C were then subcloned into pGG-55, using the XhoI site at the end of the hly sequence and the XmaI or SpeI site following the gene.

A prfA negative strain of *Listeria*, XFL-7 (provided by Dr. Hao Shen, University of Pennsylvania), was then transformed with pGG34A, B and C, to select for the retention of the plasmids in vivo.

Example 2

LLO-HMW-MAA Constructs are Expressed in *Listeria* Materials and Experimental Methods Bacteria Cultivation and Harvesting Recombinant *Listeria monocytogenes* (LM) expressing the HMW-MAA fragments A, B and C fused to LLO were grown overnight in BHI medium supplemented with streptomycin (250 ug/ml) and chloramphenicol (25 ug/ml). For induction of endogenous LLO, bacteria were cultivated in the presence of 0.2% charcoal. Culture supernatants were cleared by centrifugation at 14000 rpm for 5 minutes, and 1.35 ml supernatant was mixed with 0.15 ml of 100% TCA for protein precipitation. After incubation on ice for 1 hour, the solution was spun for 10 minutes, 14000 rpm. The pellet was resuspended in 45 microliter (mcL) of 1×SDS-PAGE gel loading buffer, 5 mcL of 1 M DTT was added, and the sample was heated at 75° C. for 5 minutes. 5-10 mcL of protein was loaded into each well and run for 50 minutes at 200V using MOPS buffer.

After transfer to PVDF membranes, membranes were incubated with either a rabbit anti-PEST polyclonal antibody (1:3000), which recognizes the PEST sequence in the LLO protein, or with the B3-19 monoclonal antibody, which recognizes the endogenous LLO only, then incubated with HRP-conjugated anti-rabbit antibody. Signals were detected with SUPERSIGNAL® West Pico Chemiluminescent Substrate (Pierce, Rockford, Ill.).

Results

Figure 2A:
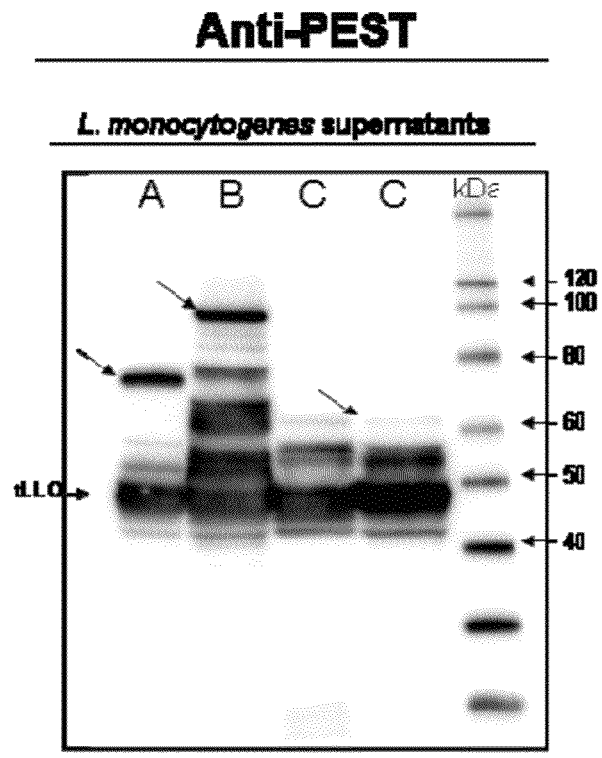
FIG. 2. LLO-HMW-MAA constructs are expressed. Supernatant was harvested from LM strains transformed with the LLO-HMW-MAA A, B and C plasmids. A. Anti-PEST probes revealed that all three strains produced fusion proteins of the expected sizes (48 Kda for LLO, 75 Kda for HMW-MAA-A, 98 Kda for HMW-MAA-B, and 62 Kda for HMW-MAA-C). B. Anti-LLO probes revealed LLO bands for HMW-MAA-A, HMW-MAA-B, HMW-MAA-C, and in 10403S controls.
Figure 2B:
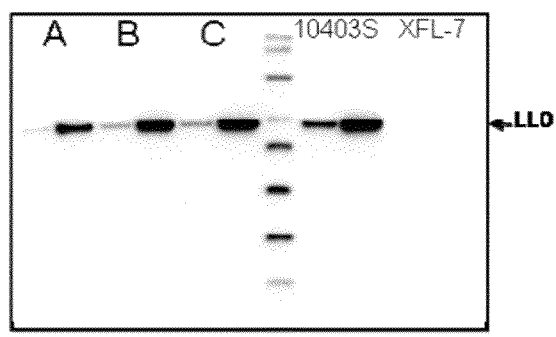

To determine whether the LLO-HMW-MAA constructs could be expressed in *Listeria*, supernatant was harvested from LM strains transformed with the LLO-HMW-MAA A, B and C plasmids, and assayed for presence of the fusion proteins. All three strains produced fusion proteins of the expected sizes when probed with anti-PEST antibody (48 Kda for LLO, 75 Kda for HMW-MAA-A, 98 Kda for HMW-MAA-B, and 62 Kda for HMW-MAA-C; FIG. 2A). Anti-LLO antibody revealed 58 Kda band for LLO in all three strains and controls (FIG. 2B).

Thus, LLO-HMW-MAA constructs are expressed in *Listeria*.

Example 3

*Listeria* Strains Expressing LLO-HMW-MAA Constructs Infect and Grow Inside Cells Materials and Experimental Methods Cell Infection Assay Murine macrophage-like J774 cells were infected at a MOI (multiplicity of infection) of 1. After a 1-hour incubation, gentamicin was added to kill extracellular *Listeria*, intracellular *Listeria* was recovered every 2 hours by lysing the J774 cells with water and plating serial dilutions of the lysate on BHI plates supplemented with streptomycin (250 micrograms (mcg)/ml) and chloramphenicol (25 mcg/ml). Recovered colonies were counted and used to determine the number of *Listeria* inside J774 cells.

Results

Figure 3A:
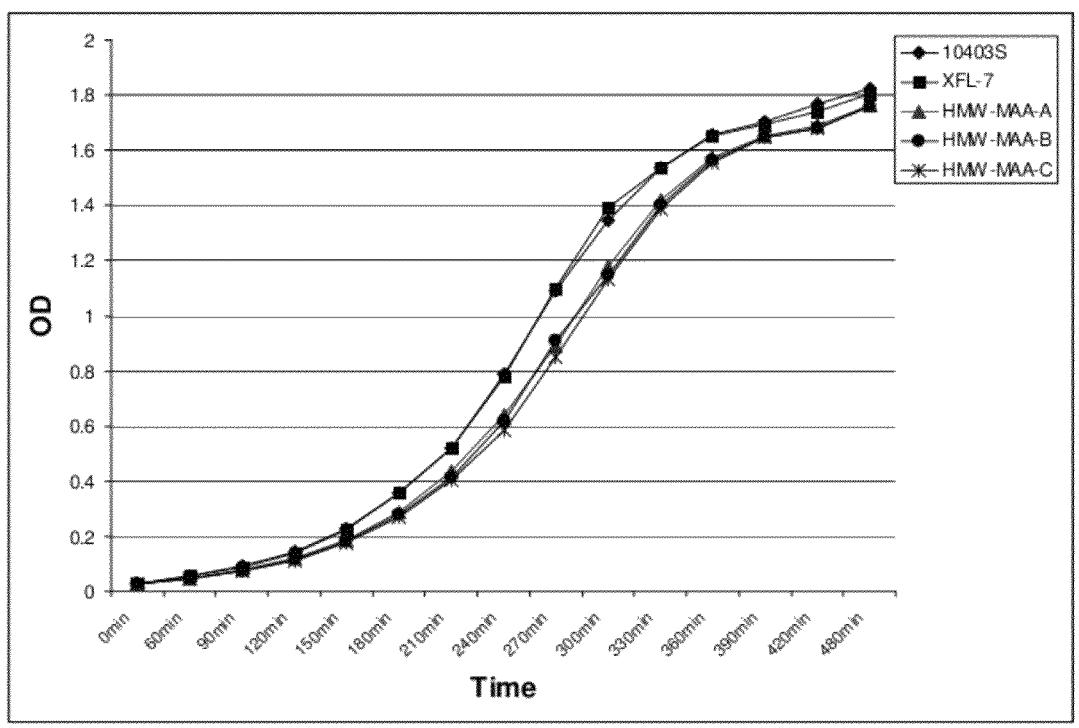
FIG. 3. Listeria strains expressing LLO-HMW-MAA constructs exhibit growth in media (A), virulence, and intracellular growth (B) similar to wild type Lm.
Figure 3B:
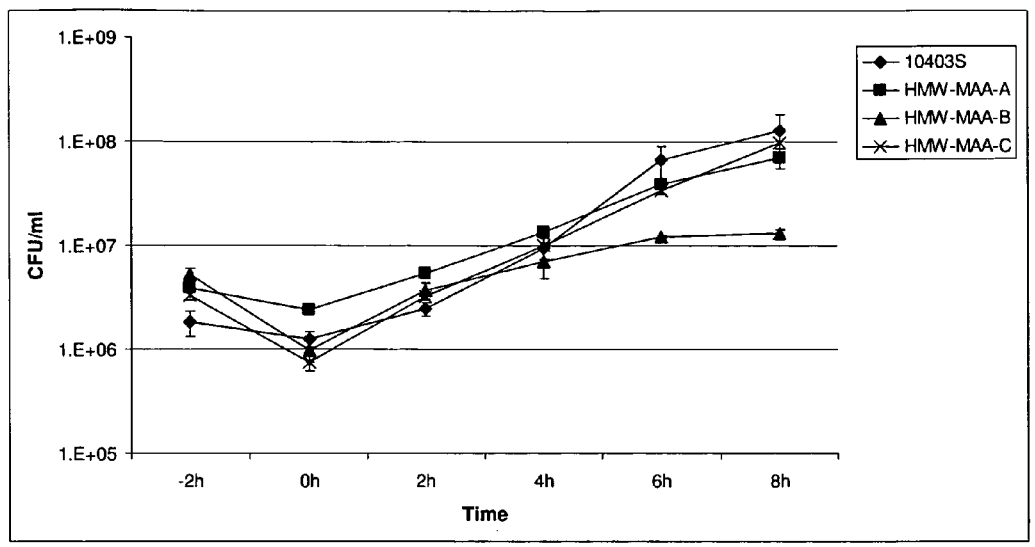

To determine the growth characteristics and virulence of *Listeria* strains expressing LLO-HMW-MAA constructs, the growth rate of *Listeria* strains from the previous Example in BHI media was measured. Each of the strains grew with kinetics very similar to wild-type (10403S) *Listeria* (FIG. 3A). Next, J774 cells were incubated with the *Listeria* strains, and intracellular growth was measured. Intracellular growth was very similar to wild-type for each strain (FIG. 3B).

Thus, *Listeria* strains expressing LLO-HMW-MAA constructs maintain their ability to grow in media, to infect cells, and to grow intracellularly.

Example 4

Vaccination with HMW-MAA-Expressing Lm Impedes B16F0-OVA Tumor Growth Materials and Experimental Methods Measurement of Tumor Growth Tumors were measured every second day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Results

Figure 4A:
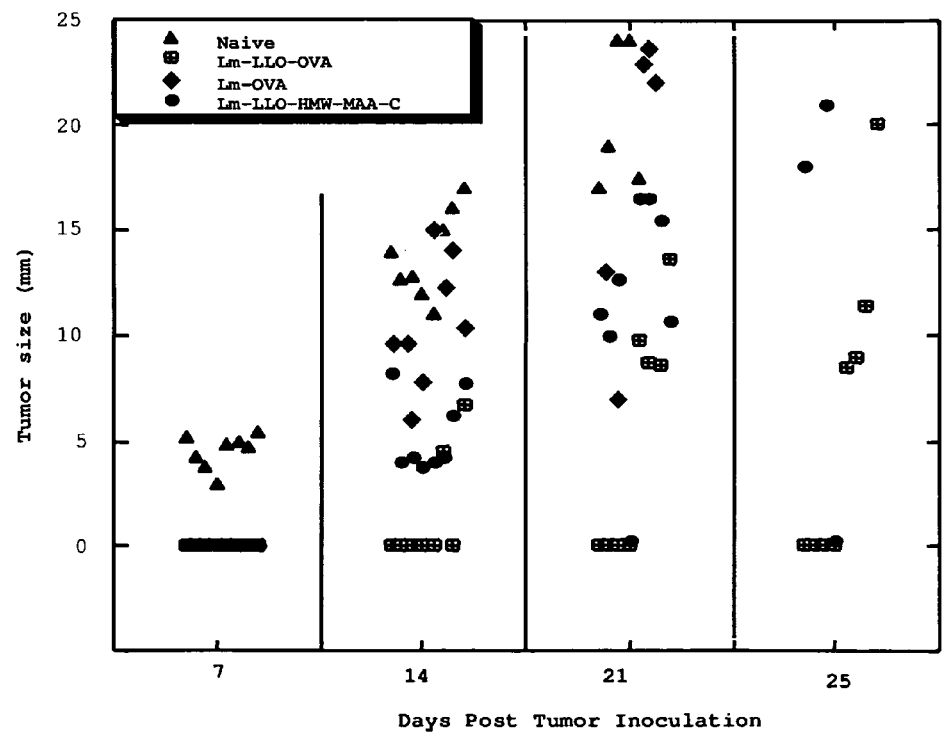
FIG. 4. HMW-MAA-expressing Lm impedes the growth of tumors, even in tumor cells that do not express HMW-MAA. $10^8$ cfu of Lm-HMW-MAA-C impedes B16F0-Ova tumor growth as measured by tumor size (A) and volume (B) significantly compared to the naïve group. Similar effects on tumor diameter and volume were observed with all three Lm-LLO-HMW-MAA strains after inoculation of C57BL/6 mice with B16F0-Ova (C) and RENCA (D and E) tumor cells.
Figure 4B:
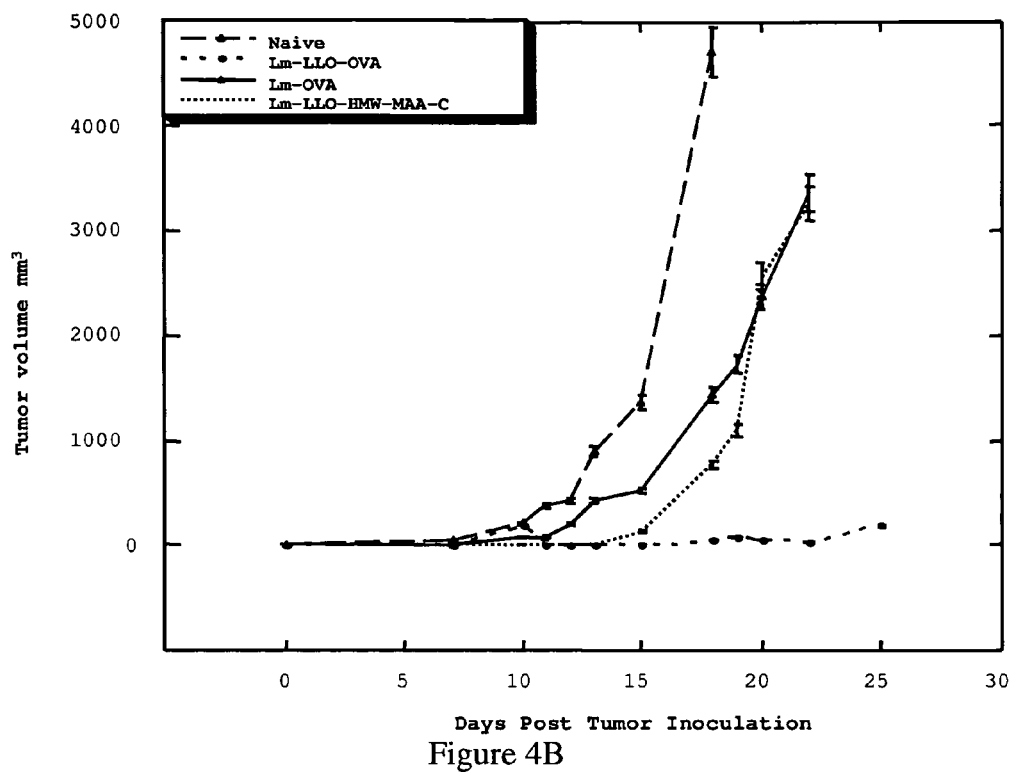
Figure 4C:
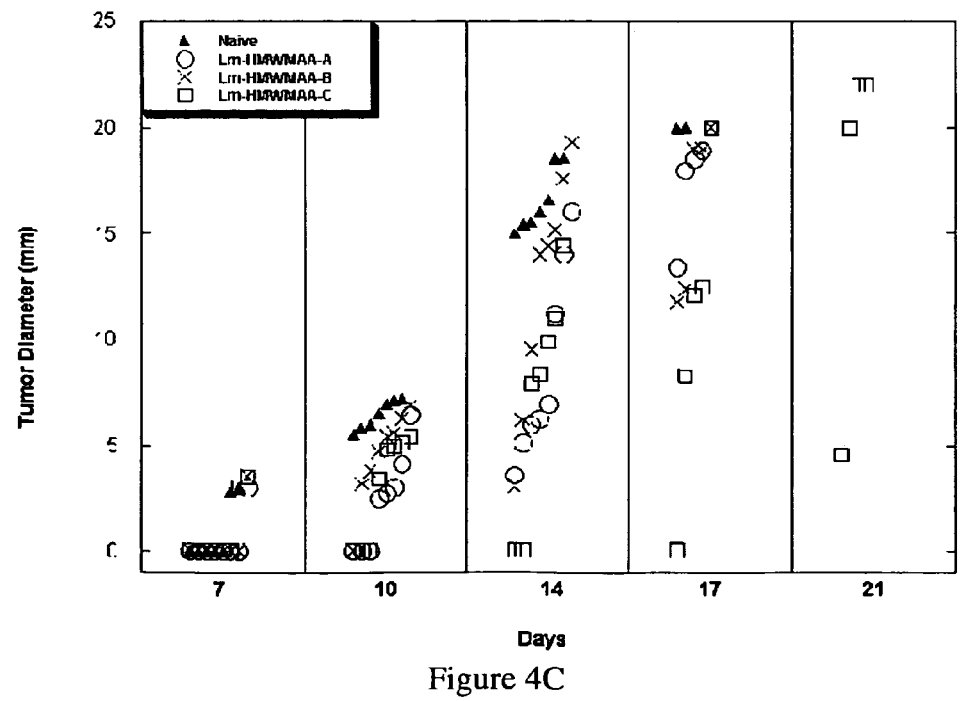

32 C57BL/6 mice (n=8 per group) were inoculated with $5 \times 10^5$ B16F0-Ova. On days 3, 10 and 17 the mice were immunized with one of 3 constructs, Lm-OVA ($10^6$ cfu), Lm-LLO-OVA ($10^8$ cfu; positive control), and Lm-LLO-HMW-MAA-C ($10^8$ cfu). Despite the lack of expression of HMW-MAA by the tumor cells, Lm-LLO-HMW-MAA-C vaccination impeded tumor growth, significantly, but to a lesser extent than Lm-LLO-OVA (FIGS. 4A-B). In an additional experiment, similar results were observed with all three Lm-LLO-HMW-MAA strains ($2.5 \times 10^7$ cfu each of A and C; $1 \times 10^8$ cfu of B; FIG. 4C).

Figure 4D:
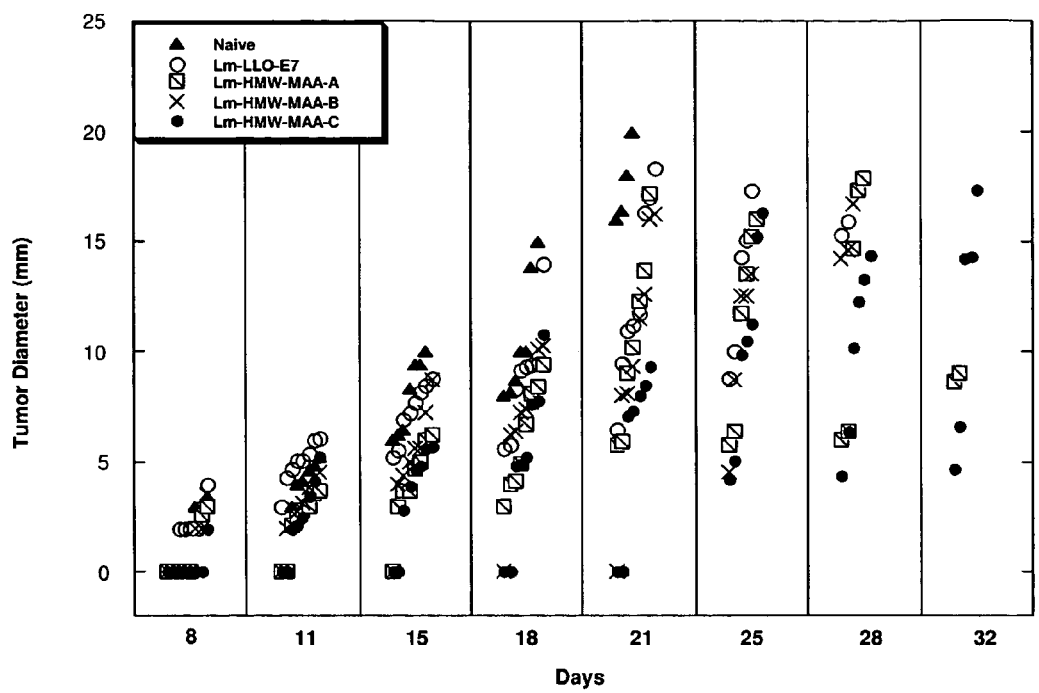
Figure 4E:
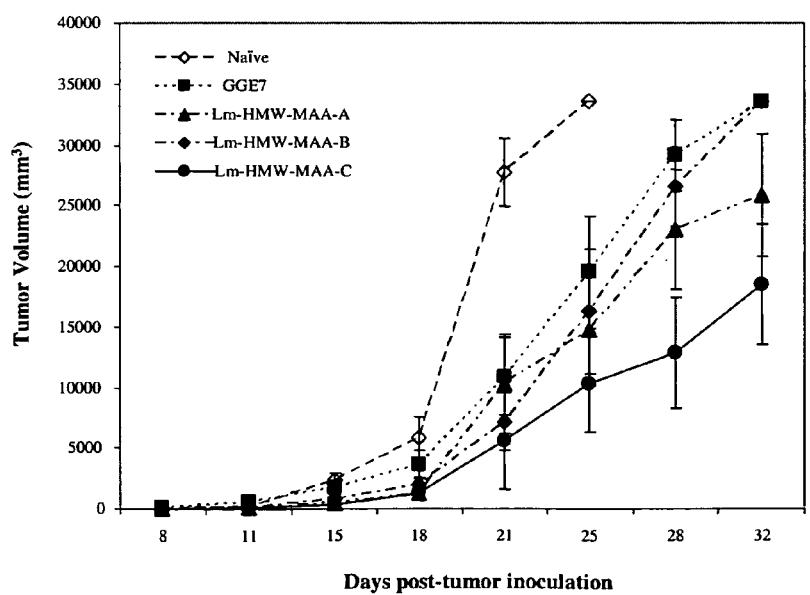

A similar experiment was performed with RENCA cells. 40 BALB/c mice (n=8 per group) were inoculated with $2 \times 10^5$ RENCA tumor cells. On days 3, 10, and 17, the mice were immunized with one of four constructs, Lm-HMW-MAA-A, B, or C (($2.5 \times 10^7$ cfu each of A and C; $1 \times 10^8$ cfu of B), or GGE7 (Lm-LLO-E7; $1.0 \times 10^8$ cfu), or were left unvaccinated (naïve). All three Lm-LLO-HMW-MAA strains impeded tumor growth, with Lm-HMW-MAA-C exerting the strongest effect (FIGS. 4D-4E).

Thus, vaccination with HMW-MAA-expressing Lm impedes the growth of tumors, even in the absence of expression of HMW-MAA by the tumor cells.

Example 5

Figure 5:
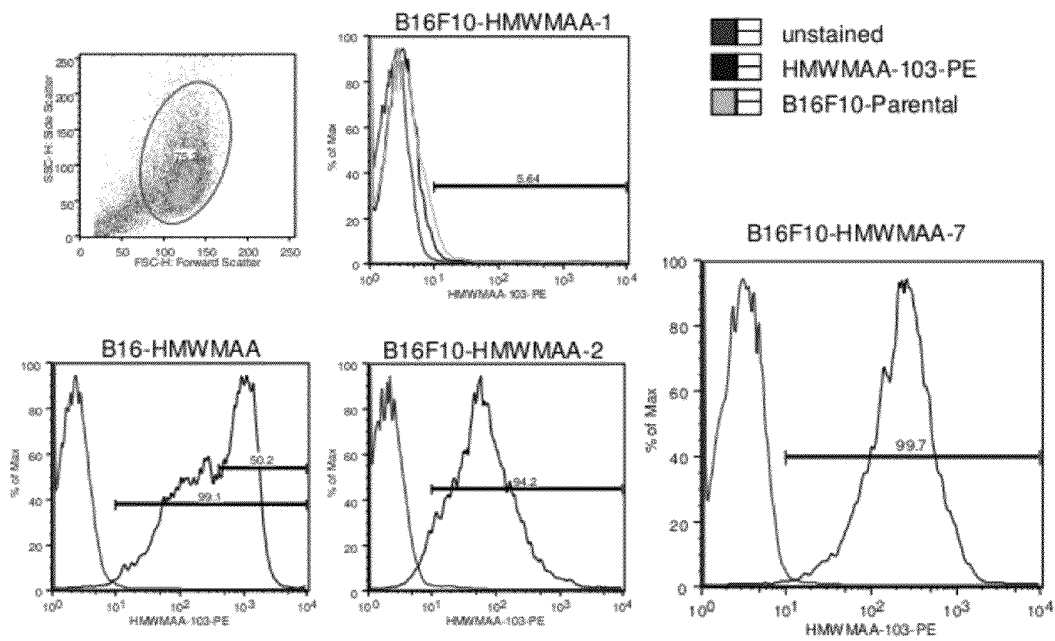
FIG. 5. Selection of HMW-MAA-expressing B16F10 murine tumor cell clones.

Vaccination with HMW-MAA-Expressing Lm Impedes B16F10-HMW-MAA Tumor Growth via CD4+ AND CD8+ Cells Materials and Experimental Methods Engineering of B16 and B16F10 Murine Tumor Cell Lines to Express HMW-MAA The B16F10 melanoma was chosen as a mouse tumor model to test the therapeutic efficacy of the Lm-LLO-HMW-MAA vaccine because HMW-MAA is expressed in a high proportion of melanoma lesions in humans. The B16F10 cell line, which does not express the mouse HMW-MAA homolog AN2, was transfected with the full-length HMW-MAA gene. B16F10 cells were transfected with pcDNA3.1-HMW-MAA plasmid, containing the full-length HMW-MAA cDNA expressed under the control of the CMV promoter. Stably transfected cells were selected by resistance to G418 antibiotic, and clones were subsequently grown from single cells by limiting dilution. Selected clones were tested by flow cytometry for HMW-MAA expression using the HMW-MAA specific monoclonal antibody VT80.12. Based on the flow cytometry results, B16F10-HMW-MAA clone 7 was selected for future experiments (FIG. 5).

CD4+ and CD8+ Depletion

32 C57BL/6 mice were inoculated with $2 \times 10^5$ B16F10-HMW-MAA/CMV7. On days 3, 10 and 17 the mice were immunized with Lm-HMW-MAA-C ($2.5 \times 10^7$ cfu), except the control naïve group. For CD4 and CD8 depletions, 500 µg of GK1.5 and 2.43 were given i.p. on days 1, 2, 6 and 9, as well as the control antibody G1. For CD25 depletion, 500 µg of CP61 was given i.p. on days 0 and 2.

Immunization of HLA A2/$K^b$ Transgenic Mice with Lm-HMW-MAA-B or Lm-HMW-MAA-C

HLA A2/$K^b$ transgenic mice express a chimeric class I molecule composed of the α1 and α2 domains of the human A*0201 allele and the α3 domains of the mouse H-2K$^b$ class I molecules. HLA-A2/K$^b$ transgenic mice were immunized once with either $1.0\times10^8$ cfu of Lm-HMW-MAA-B or $2.5\times10^7$ cfu of Lm-HMW-MAA-C. Nine days later, splenocytes were stimulated in vitro with peptide B$_1$ (ILSNLSFPV; SEQ ID NO: 43; corresponds to HMW-MAA$_{769-777}$), peptide B$_2$ (LLFGSIVAV; SEQ ID NO: 44; corresponds to HMW-MAA$_{1063-1071}$), or peptide C (LILPLLFYL; SEQ ID NO: 45; corresponds to HMW-MAA$_{2238-2246}$) for 5 hours in the presence of monensin. Cells were gated on CD8+-CD62L$^{low}$ and IFN-γ intracellular staining was measured.

In a separate experiment, mice were immunized twice (day 0 and day 7) with either Lm-HMW-MAA-B or Lm-HMW-MAA-C and splenocytes harvested on day 14 for in vitro stimulation with fragment B1 or C of Lm-HMW-MAA. IFN-γ levels were measured using IFN-γ Elispot.

Results

Figure 6:
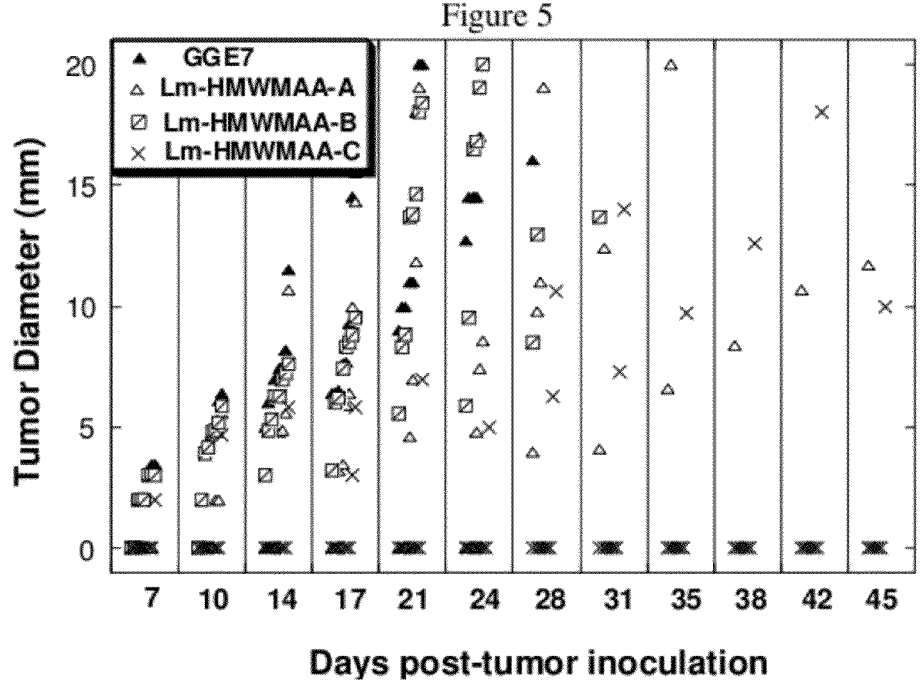
FIG. 6. Lm-HMW-MAA constructs induced antigen-specific immune responses that impede tumor growth.

C57BL/6 mice (n=8 per group) were inoculated with $2\times10^5$ B16F10-HMW-MAA/CMV7. On days 3, and 17, mice were immunized with one of three constructs, Lm-HMW-MAA-A ($2.5\times10^7$ cfu), Lm-HMW-MAA-B ($1\times10^8$ cfu), Lm-HMW-MAA-C ($2.5\times10^7$ cfu). The control group was vaccinated with Lm-GGE7 ($1\times10^8$ cfu). All three Lm-HMW-MAA constructs exerted significant anti-tumor effects (FIG. 6).

Figure 7:
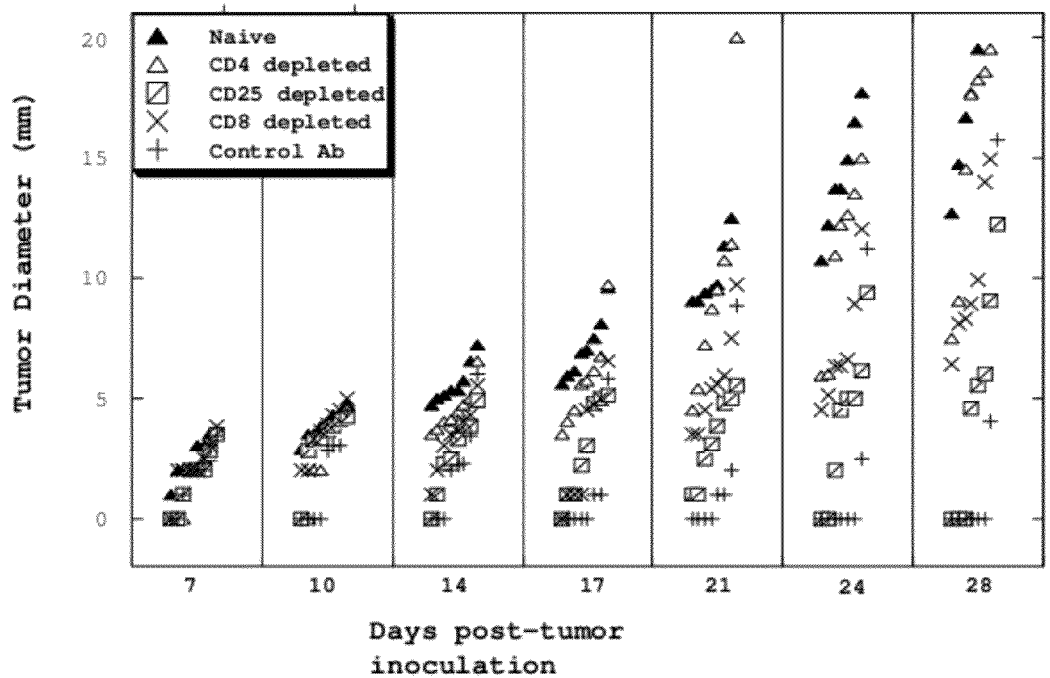
FIG. 7. In vivo depletion of either CD4+ or CD8+ cells abrogated the efficacy of Lm-HMW-MAA-C vaccine.

To determine the role of CD4+ and CD8+ cells in the anti-tumor effect of Lm-HMW-MAA, CD4+ or CD8+, cells were depleted by antibody administration in C57BL/6 mice who had been innoculated with B16F10-HMW-MAA/CMV7B and immunized on days 3, 10, and 17 with Lm-HMW-MAA-C ($2.5\times10^7$ cfu). CD4+ or CD8+ depletion abrogated the efficacy of LM-HMW-MAA-C vaccine (FIG. 7). In the non-immunized control group, all mice developed tumors, whereas 50% of the mice immunized with Lm-LLO-HMW-MAA-C and given a control antibody remained tumor-free for at least 56 days after tumor-challenge. On the other hand, none of the mice receiving either the anti-CD8 or anti-CD4 antibodies could control the tumor growth, showing that both cells types play an important role in the anti-tumor immunity generated by the Lm-LLO-HMW-MAA-C vaccine (FIG. 7). However, administration of the anti-CD25 antibody did not improve the efficacy of the Lm-LLO-HMW-MAA-C vaccine, suggesting that the subset of CD4$^+$ CD25$^+$ T regulatory cells does not have a significant influence in this model (FIG. 7).

Figure 8:
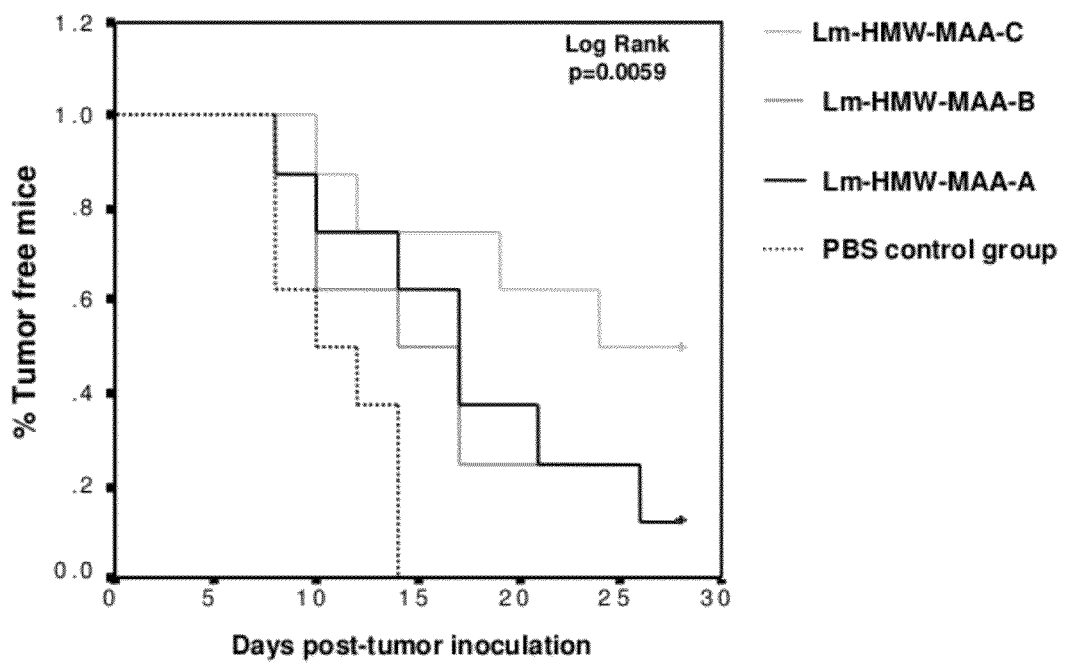
FIG. 8. CD8+ T cells from mice vaccinated with Lm-HMW-MAA-C mice inhibited the growth of B16F10 HMW-MAA tumors in vivo.

Lm vectors are recognized for their ability to generate strong CD8$^+$ T cell responses, which are important for tumor rejection. To verify if the CD8$^+$ T cells generated upon immunization with Lm-LLO-HMW-MAA-C had anti-tumor activity against the B16F10-HMW-MAA cell line, CD8$^+$ T cells ($2\times10^6$ cells per mouse) were purified from the spleens of mice from each treatment group, mixed with B16F10-HMW-MAA tumor cells ($2\times10^5$ per mouse), and then subcutaneously injected in mice (8 per group). Mice were observed for 28 days and examined every 2 days for tumor growth. CD8$^+$ T cells from Lm-HMW-MAA-C-vaccinated mice inhibited the growth of B16F10 HMW-MAA tumors in vivo (FIG. 8). When mixed with CD8$^+$ T cells from mice immunized with Lm-LLO-HMW-MAA-C, 50% of the naïve animals did not develop tumors in four weeks, as compared to none in the control group ($P\leq0.05$). This result indicates that vaccination with Lm-LLO-HMW-MAA-C induces CD8$^+$ T cells able to inhibit the in vivo growth of the B16F10-HMW-MAA cell line.

Figure 9:
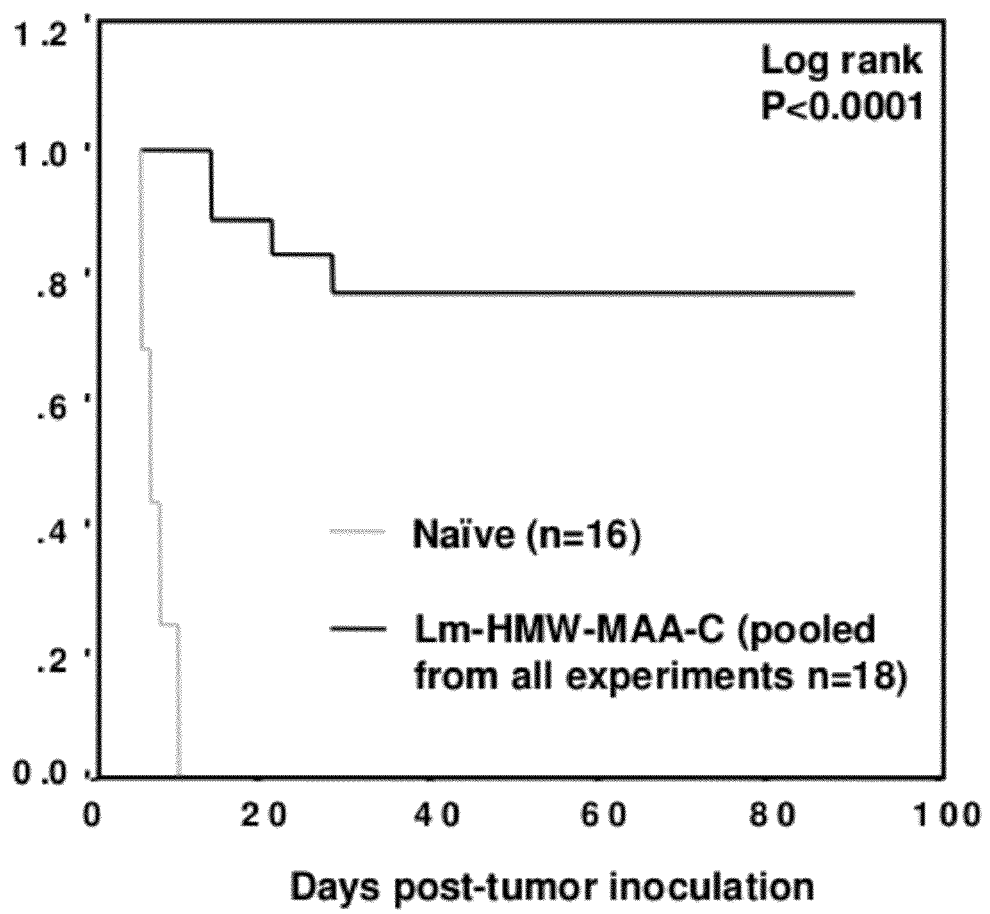
FIG. 9. Mice vaccinated with Lm-HMW-MAA-C that eliminated the B16F10-HMW-MAA tumor were protected against a second challenge with the same tumor.

Mice that had been inoculated with $2\times10^5$ B16F10-HMW-MAA/CMV7 and vaccinated with Lm-HMW-MAA-C as described above and remained tumor-free after 7 weeks were re-challenged with $2\times10^5$ B16F10-HMW-MAA cells 7 weeks after the first tumor injection. Vaccinated mice were protected against a second challenge with B16F10-HMW-MAA/CMV7 tumor cells (FIG. 9).

Figure 10A:
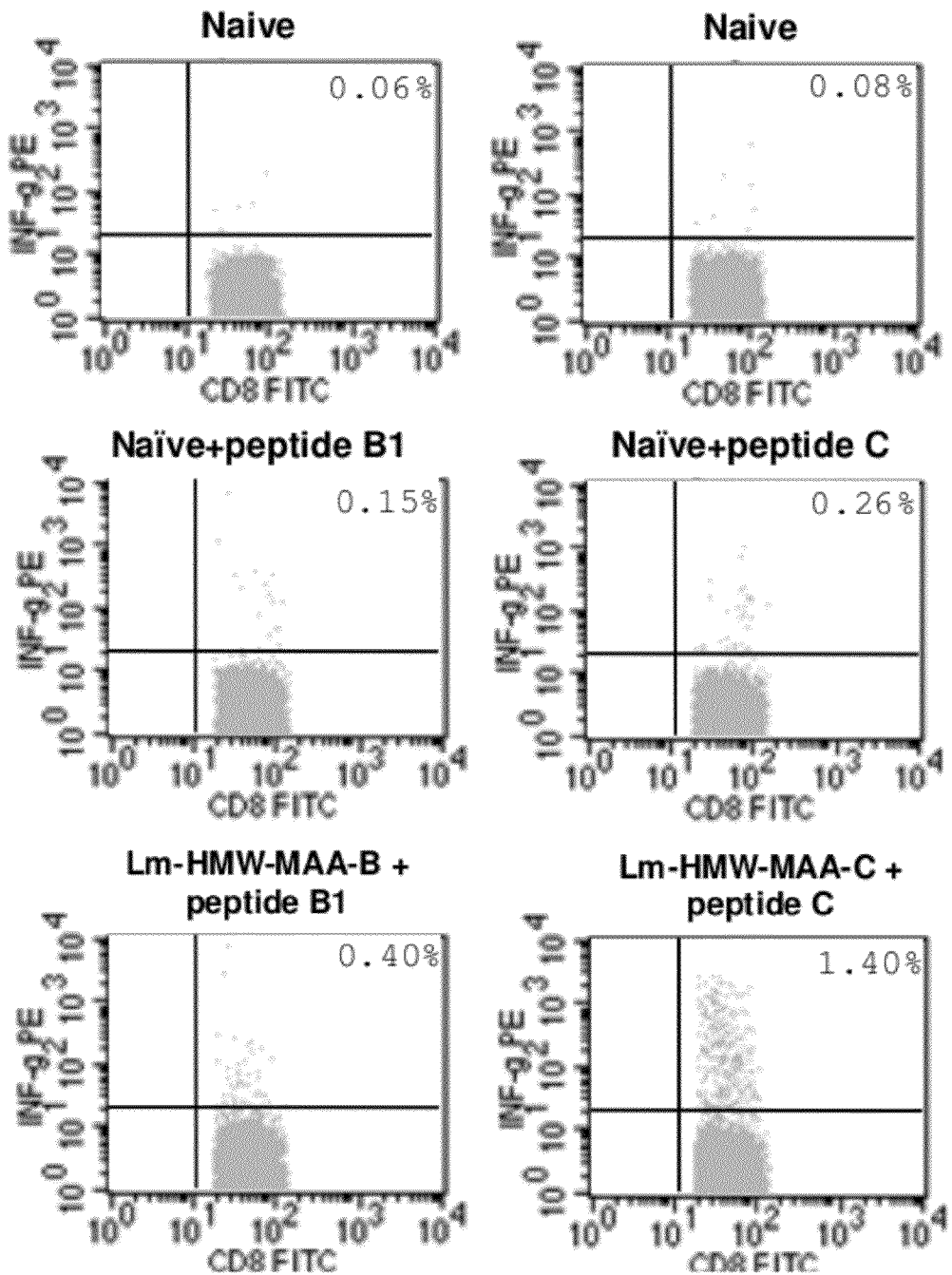
FIG. 10. Immunization of HLA-A2/Kb transgenic mice with Lm-HMW-MAA-B and Lm-HMW-MAA-C induced detectable immune responses against two characterized HMW-MAA HLA-A2 epitopes in fragments B and C.
Figure 10B:
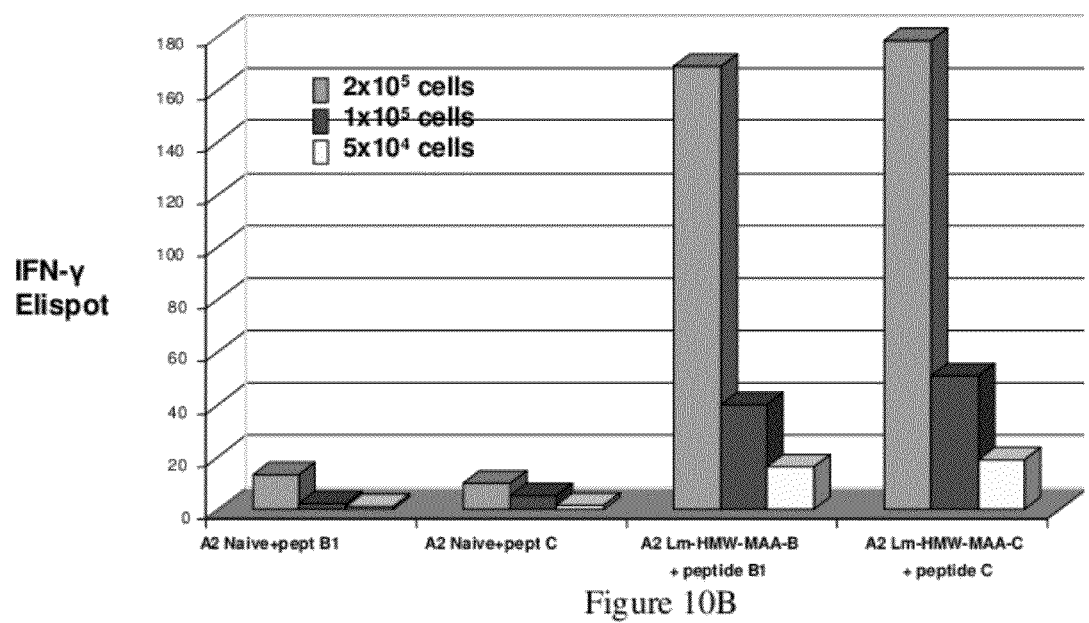

Immunization of HLA-A2/K$^b$ transgenic mice with Lm-HMW-MAA-B and Lm-HMW-MAA-C induces detectable immune responses against two characterized HMW-MAA HLA-A2 epitopes in fragments B and C both after one (FIG. 10A) or two immunizations (FIG. 10B).

Figure 11A:
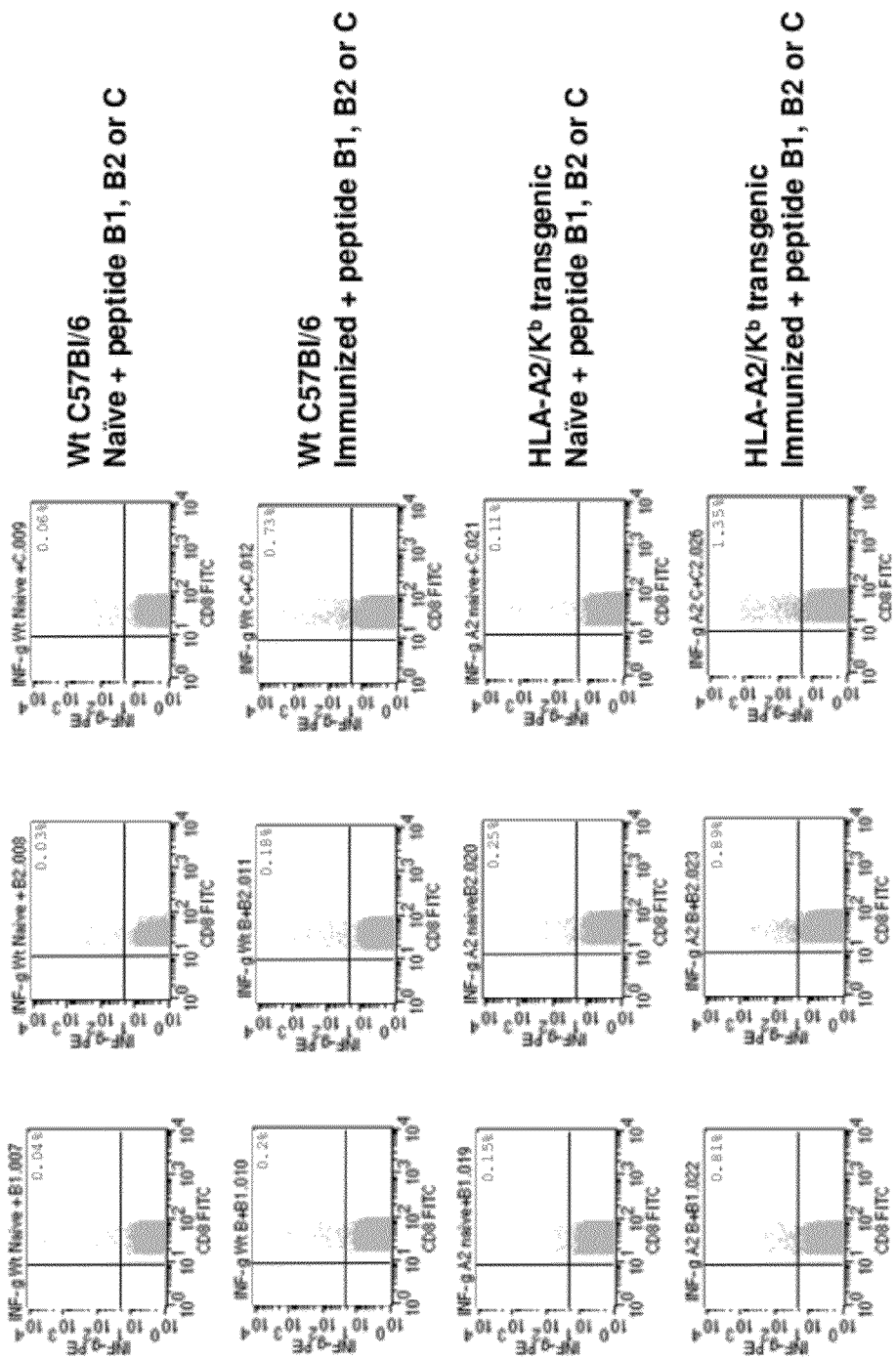
FIG. 11. IFN-γ secretion by T cells stimulated with an HLA-A2 restricted peptide from fragment C of HMW-MAA after one immunization with Lm-HMW-MAA-C in HLA-A2/Kb and wild-type C57B1/6 mice.
Figure 11B:
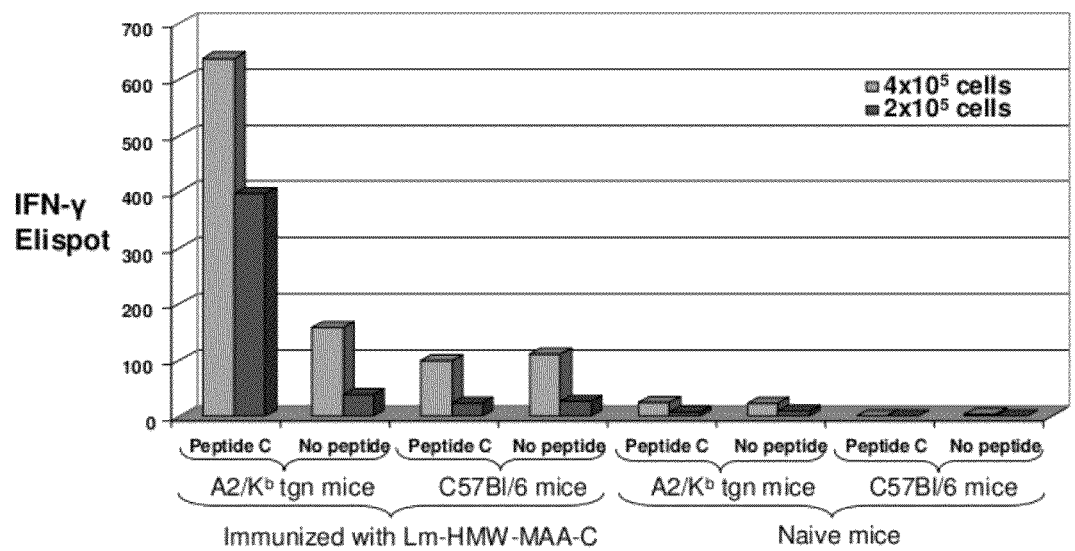

HLA-A2/K$^b$ and wild-type C57Bl/6 mice were immunized once with Lm-HMW-MAA-B or Lm-HMW-MAA-C, and IFN-γ secretion by T cells stimulated with an HLA-A2 restricted peptide from fragment C was measured with IFN-γ Elispot. IFN-γ secretion was increased in Lm-HMW-MAA-C-immunized HLA-A2/K$^b$ transgenic mice stimulated with Peptide C compared to unstimulated transgenic mice, compared to Peptide C-stimulated non-transgenic mice and compared to non-immunized transgenic and control mice (FIGS. 11A and 11B).

The HMW-MAA fragment expressed and secreted by the Lm-LLO-HMW-MAA-C vaccine contains the HLA-A2-restricted epitope $_{2238}$LILPLLFYL$_{2246}$. To test whether immunization with Lm-LLO-HMW-MAA-C was able to induce immune responses against this epitope, we vaccinated either HLA-A2/K$^b$ transgenic mice or C57BL/6 mice with Lm-LLO-HMW-MAA-C and analyzed the production of IFN-γ by ELISpot after stimulation with HMW-MAA$_{2238-2246}$ peptide. Following two immunizations, a significantly higher number of SFC was detected in splenocytes from the HLA-A2/K$^b$ transgenic mice, but not in the C57BL/6 mice. Similar results were obtained using intracellular staining for IFN-γ. After one immunization with Lm-LLO-HMW-MAA-C, IFN-γ production was detected in 0.51% of the CD8$^+$ T cells from the HLA-A2/K$^b$ transgenic mice stimulated with the HMW-MAA$_{2238-2246}$ peptide, compared to 0.06% in the absence of the peptide. No responses could be detected in non-transgenic C57Bl/6 mice (data not shown). These results show that immunization with the Lm-LLO-HMW-MAA-C vaccine can induce CD8$^+$ T cell responses against a HMW-MAA epitope restricted to the HLA-A2 molecule.

Thus, Lm-HMW-MAA constructs induce antigen-specific immune responses that impede tumor growth. In addition, the Lm-HMW-MAA constructs exhibit anti-tumor activity even against tumors not expressing HMW-MAA.

Example 6

Vaccination with HMW-MAA-Expressing Lm Induces Breast Tumor Regression

FVB/N 6-8 week old female mice were injected subcutaneously with $1\times10^6$ NT-2 tumor cells suspended in 1×PBS at a total volume of 200 μl. Mice were immunized with either $1\times10^7$ Lm-LLO-NYESO-1 *Listeria* vaccine or $2.5\times10^7$ Lm-LLO-HMWMAA-C *Listeria* vaccine in 1×PBS, 200l total volume, i.p. on days 7, 14 and 21. Tumors were measured every week started from day 7. The NYESO-1 group were 8 mice total, the HMWMAA-C group was 5 mice total.

Figure 12:
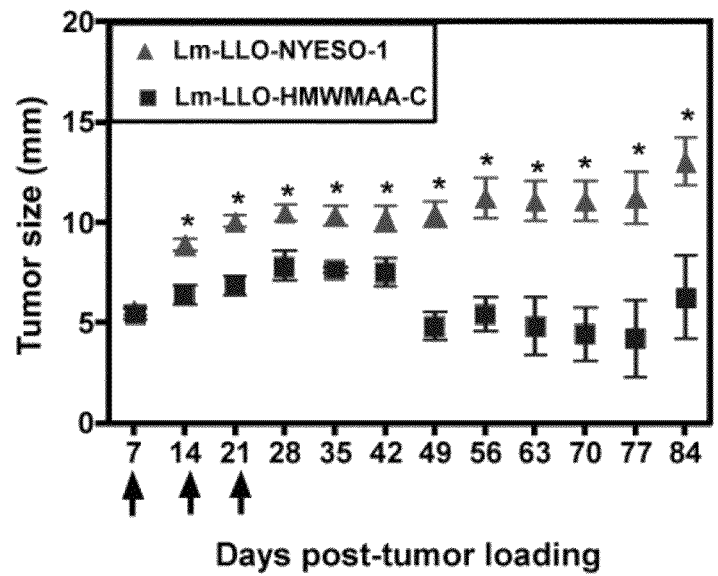
FIG. 12. Vaccination of mice with Lm-HMW-MAA-C impairs the growth of NT-2 tumors. In the NYESO-1-vaccinated group, 0/8 showed total tumor regression; 2/5 mice in the HMWMAA group had complete tumor regression (size=0.0 mm). Mice were observed out to 84 days post initial tumor load. Significance determined using the two-tailed Mann-Whitney statistical test, *p<0.05 for NYESO-1 compared to HMWMAA-C on that particular day.

From the NYESO-1 group, 0/8 showed total tumor regression; 2/5 mice in the HMWMAA group had complete tumor regression (size=0.0 mm). The group immunized with Lm-LLO-HMWMAA-C had significantly decreased tumor size compared to the group immunized with Lm-LLO-NYESO-1 (FIG. 12).

Interestingly, we observed that immunization of mice with Lm-LLO-HMW-MAA-C could impact the growth of several different tumors that were not engineered to express HMW-MAA, such as the parental B16F10, RENCA and NT-2 tumors, which were derived from distinct mouse strains. In the RENCA, which is a spontaneous renal carcinoma cell line derived from the BALB/c mouse, and B16F10 models, mice were immunized weekly with Lm-LLO-HMW-MAA-C three times, starting 3 days after tumor challenge. Immunization with Lm-LLO-HMW-MAA-C significantly delayed the growth of these tumors (FIGS. 13A and B). In the NT-2 tumor model, which is a mammary carcinoma cell line expressing the rat HER-2/neu protein and is derived from the FVB/N HER-2/neu transgenic mice, immunization with Lm-LLO-HMW-MAA-C 7 days after tumor inoculation not only impaired tumor growth but also induced regression of the tumor in 1 out of 5 mice (FIG. 13C). Furthermore, these results could not be attributed to a non-specific Lm effect since a control Lm vaccine strain did not impact on the growth of B16F10, RENCA (FIG. 13B) or NT-2 tumors (FIG. 13C). We also evaluated the effect of Lm-LLO-HMW-MAA-C immunization in a spontaneous tumor model using the FVB/N HER-2/neu transgenic mouse. These mice express the rat HER-2/neu proto-oncogene under the control of the mouse mammary tumor virus (MMTV) promoter. In this transgenic mouse strain, over 90% of the females develop focal mammary tumors after a latency of about 4-6 months. Immunization with Lm-LLO-HMW-MAA-C significantly delayed the median time for the onset of mammary tumors in these mice (39 weeks), as compared to a control Lm vaccine (25 weeks) (FIG. 13D).

Figure 14:
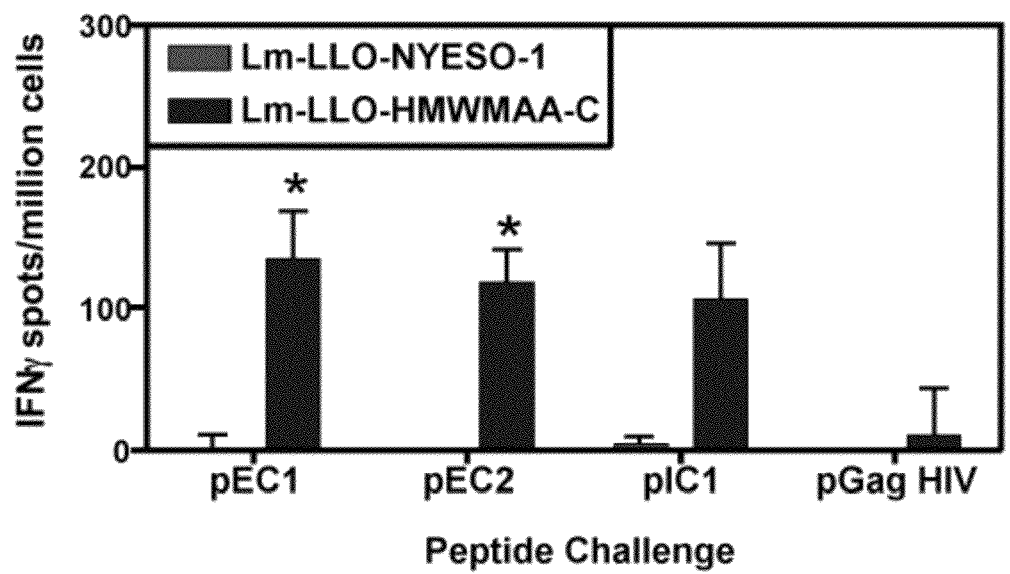
FIG. 14. Detection antibodies for anti-IFNgamma. Peptides were added to corresponding wells for a final concentration of 2 uM. Background spots (medium alone) were subtracted from values shown. Statistical test, Mann-Whitney, two-tailed, was performed to determine statistical significance. A p value less than 0.05 was considered to be significant. *p<0.05, is significant for the HMWMAA-C group compared NYESO-1. pEC1=PYNYLSTEV, pEC2=PDSLRDLSVF, plC1=PNQAQMRIL.

Thereafter, spleens taken from 84 day mice were glass homogenized and washed, RBC-lysed, then counted for Elispots. Splenocytes were placed in Elispot wells and titrated, primary and detection antibodies were anti-IFN-gamma. Peptides were added to corresponding wells for a final concentration of 2 µM. Background spots (medium alone) were subtracted from values shown. Statistical test, Mann-Whitney, two-tailed, was performed to determine statistical significance (FIG. 14).

Figure 15:
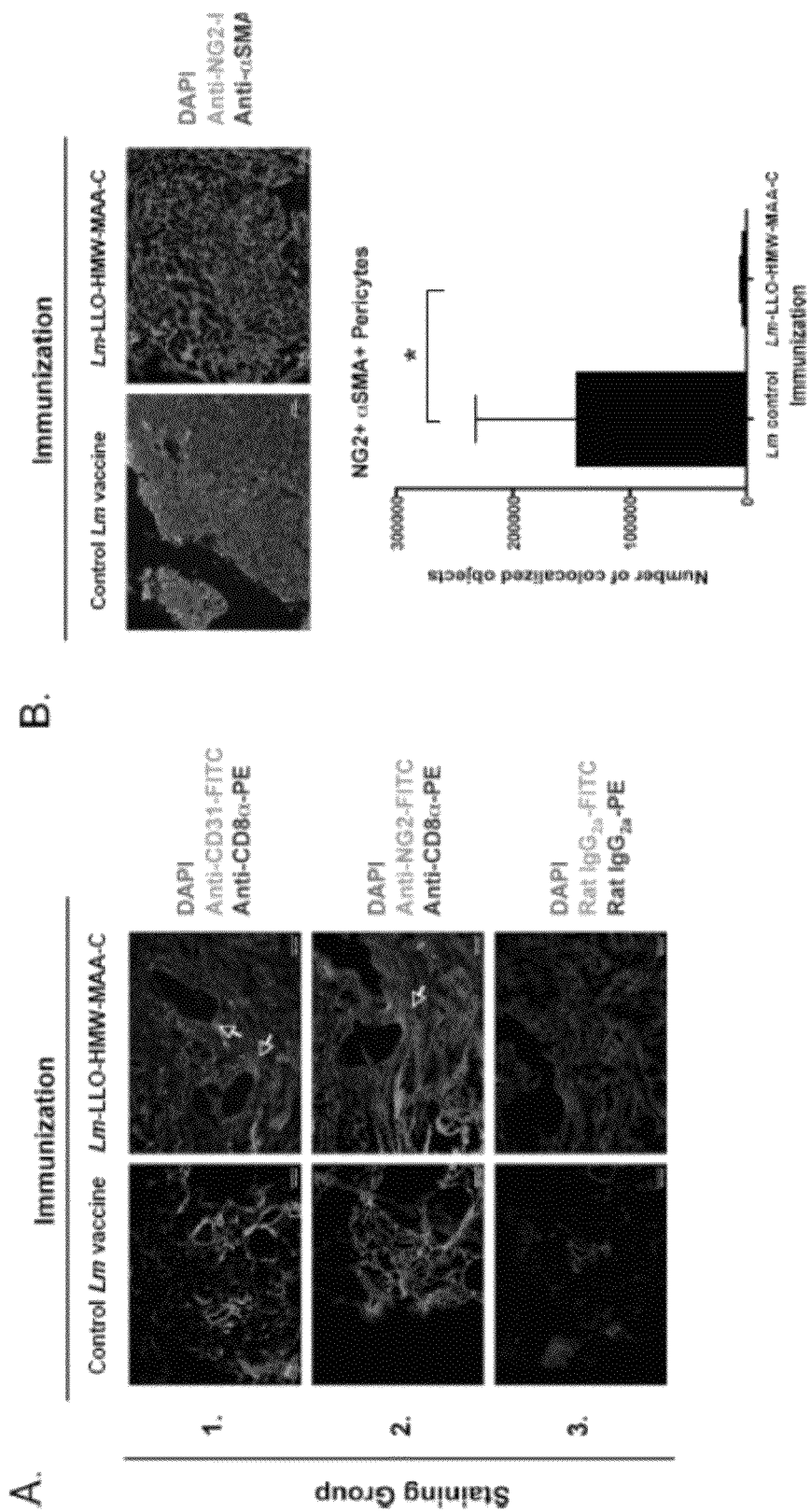
FIG. 15. Immunization with Lm-HMW-MAA-C promotes tumor infiltration by CD8+ cells and decreases the number of pericytes in blood vessels. A, NT-2 tumors were removed and sectioned for immunofluorescence. Staining groups are numbered (1-3) and each stain is indicated on the left. Sequential tissues were either stained with the pan-vessel marker anti-CD31 or the anti-NG2 antibody for the HMW-MAA mouse homolog AN2, in conjunction with anti-CD8α for possible TILs. Group 3 shows isotype controls for the above antibodies and DAPI staining used as a nuclear marker. A total of 5 tumors were analyzed and a single representative image from each group is shown. CD8+ cells around blood vessels are indicated by arrows. B, sequential sections were stained for pericytes by using the anti-NG2 and anti-alpha-smooth-muscle-cell-actin (αSMA) antibodies. Double staining/colocalization of these two antibodies (yellow in merge image) are indicative of pericyte staining (top). Pericyte colocalization was quantitated using Image Pro Software and the number of colocalized objects is shown in the graph (bottom). A total of 3 tumors were analyzed and a single representative image from each group is shown. *, P≦0.05, Mann-Whitney test. Graph shows mean±SEM.

Although NT-2 cells do not express the HMW-MAA homolog AN2, immunization of FVB/N mice with Lm-LLO-HMW-MAA-C significantly impaired the growth of NT-2 tumors and eventually led to tumor regression (FIG. 13C). One hypothesis is that activated pericytes present in tumor blood vessels, which express the AN2/HMW-MAA marker, could be a potential target for HMW-MAA vaccines. Because Lm-LLO-HMW-MAA-C vaccination had a pronounced effect in NT-2 tumors, we used this tumor model to evaluate $CD8^+$ T cells and pericytes in the tumor site by immunofluorescence. Staining of NT-2 tumor sections for CD8 showed infiltration of $CD8^+$ T cells into the tumors and around blood vessels in mice immunized with the Lm-LLO-HMW-MAA-C vaccine, but not in mice immunized with the control vaccine (FIG. 15A). We also analyzed pericytes in NT-2 tumors by double staining with αSMA and NG2 antibodies. The NG2 protein is the rat homolog of HMW-MAA and the NG2 antibody used in this study has been shown to cross-react with the mouse homolog AN2. Data analysis from 3 independent NT-2 tumors showed a significant decrease in the number of pericytes in mice immunized with Lm-LLO-HMW-MAA-C, as compared to control ($P \leq 0.05$) (FIG. 15B). Similar results were obtained when the analysis was restricted to cells stained for αSMA, which is not targeted by the vaccine (data not shown). This finding is in agreement with the hypothesis that Lm-LLO-HMW-MAA-C vaccination might potentially impact blood vessel formation in the tumor site by targeting pericytes.

Immunization with HMW-MAA-C has no impact on wound healing, pregnancy and fertility in mice. To evaluate whether Lm-LLO-HMW-MAA-C causes toxicity that is associated with angiogenesis inhibition, we studied wound healing, pregnancy and fertility in immunized mice. No significant difference was observed in the time required for wound closure in mice immunized with Lm-LLO-HMW-MAA-C as compared to a control Lm vaccine or saline injection (FIG. 16A). Similarly, Lm-LLO-HMW-MAA-C immunization had no impact on fertility, gestation length and pup mass at birth (FIG. 16B). Thus, despite its effect on tumor vasculature, we did not observe toxicity associated with blood vessel damage in mice immunized with Lm-HMW-MAA-C, such as wound healing, pregnancy or fertility problems.

These findings demonstrated that a breast tumor, NT-2, which expresses HER-2/neu, can be eliminated by the vaccine of the invention. Lm-LLO-HMW-MAA fragment C (residues 2160-2258, SEQ ID NO: 3) is effective at controlling a breast tumor growth. In addition, the present findings demonstrate the dual action of the vaccine in spreading the immune response from HMW-MAA to the HER-2/neu antigen expressed by the breast tumor cells. Immunohistochemical staining indicated that the anti-HMW-MAA CTL induced is found located around the tumor blood vessels, confirming that the immune response targets the tumor vasculature. Since tumors need vasculature to grow, vaccination with Lm-LLO-HMW-2160-2258 is effective against all tumor types. However, Lm-LLO-HMW-2160-2258 is particularly effective in tumors expressing HER-2/neu.

Example 7

Fusion of E7 to LLO or ActA Enhances E7-Specific Immunity and Generates Tumor-Infiltrating E7-Specific $CD8^+$ Cells Materials and Experimental Methods Construction of Lm-actA-E7

Lm-actA-E7 was generated by introducing a plasmid vector pDD-1 constructed by modifying pDP-2028 into LM. pDD-1 comprises an expression cassette expressing a copy of the 310 bp hly promoter and the hly signal sequence (ss), which drives the expression and secretion of actA-E7; 1170 bp of the actA gene that comprises 4 PEST sequences (SEQ ID NO: 5) (the truncated ActA polypeptide consists of the first 390 AA of the molecule, SEQ ID NO: 4); the 300 bp HPV E7 gene; the 1019 bp prfA gene (controls expression of the virulence genes); and the CAT gene (chloramphenicol resistance gene) for selection of transformed bacteria clones.

pDD-1 was created from pDP2028 (encoding ΔLLO-NP), which was in turn created from pDP1659 as follows:

Construction of pDP1659: The DNA fragment encoding the first 420 AA of LLO and its promoter and upstream regulatory sequences was PCR amplified with LM genomic DNA used as a template and ligated into pUC19. PCR primers used were 5'-GGCCCGGGCCCCCTCCTTTGAT-3' (SEQ ID No: 30) and 5'-GGTCTAGATCATAATTTACTTCATCC-3' (SEQ ID No: 31). The DNA fragment encoding NP was similarly PCR amplified from linearized plasmid pAPR501 (obtained from Dr. Peter Palese, Mt. Sinai Medical School, New York) and subsequently ligated as an in-frame translational fusion into pUC19 downstream of the hemolysin gene fragment. PCR primers used were 5'-GGTCTAGAGAATTC-CAGCAAAAGCAG-3' (SEQ ID No: 32) and 5'-GGGTC-GACAAGGGTATTTTCTTTAAT-3' (SEQ ID No: 33). The fusion was then subcloned into the EcoRV and SalI sites of pAM401. Plasmid pDP2028 was constructed by subcloning the prfA gene into the SalI site of pDP1659.

pDD-1 was created from pDP-2028 (Lm-LLO-NP) as follows:

The hly promoter (pHly) and gene fragment (441 AA) were PCR amplified from pGG55 using primer 5'-GGGG TCTAGACCTCCTTTGATTAGTATATTC-3' (Xba I site is underlined; SEQ ID NO: 34) and primer 5'-ATCTTCGC-TATCTGTCGC CGCGGCGCGTGCTTCAGTTTGTTGCGC-'3 (Not I site is underlined. The first 18 nucleotides are the ActA gene overlap; SEQ ID NO: 35). The actA gene was PCR amplified from the LM 10403s wildtype genome using primer 5'-GCGCAA-CAAACTGAAGCAGC GGCCGCGGCGACAGATAGCGAAGAT-3' (NotI site is underlined; SEQ ID NO: 36) and primer 5'-TGTAGGTG-TATCTCCATGCTCGAGAGCTAGGCGATCAATTTC-3' (XhoI site is underlined; SEQ ID NO: 37). The E7 gene was PCR amplified from pGG55 using primer 5'-GGAAT-TGATCGCCTAGCT CTCGAGCATGGAGATACACCTACA-3' (XhoI site is underlined; SEQ ID NO: 38) and primer 5'-AAACGGATT-TATTTAGATCCCGGGTTATGGTTTCTGAGAACA-3' (XmaI site is underlined; SEQ ID NO: 39). The prfA gene was PCR amplified from the LM 10403s wild-type genome using primer 5'-TGTTCTCAGAAACCATAA CCCGGGATCTAAATAAATCCGTTT-3' (XmaI site is underlined; SEQ ID NO: 40) and primer 5'-GGGGG TCGACCAGCTCTTCTTGGTGAAG-3' (SalI site is underlined; SEQ ID NO: 41). The hly promoter-actA gene fusion (pHly-actA) was PCR generated and amplified from purified pHly and actA DNA using the upstream pHly primer (SEQ ID NO: 34) and downstream actA primer (SEQ ID NO: 37).

The E7 gene fused to the prfA gene (E7-prfA) was PCR generated and amplified from purified E7 and prfA DNA using the upstream E7 primer (SEQ ID NO: 38) and downstream prfA gene primer (SEQ ID NO: 41).

The pHly-actA fusion product fused to the E7-prfA fusion product was PCR generated and amplified from purified fused pHly-actA and E7-prfA DNA products using the upstream pHly primer (SEQ ID NO: 34) and downstream prfA gene primer (SEQ ID NO: 41) and ligated into pCR11 (Invitrogen, La Jolla, Calif.). Competent E. coli (TOP10'F, Invitrogen, La Jolla, Calif.) were transformed with pCRII-ActAE7. After lysis and isolation, the plasmid was screened by restriction analysis using BamHI (expected fragment sizes 770 and 6400 bp) and BstXI (expected fragment sizes 2800 and 3900) and screened by PCR using the above-described upstream pHly primer and downstream prfA gene primer.

The pHly-ActA-E7-PrfA DNA insert was excised from pCRII by XbaI/SalI digestion with and ligated into XbaI/Sal I digested pDP-2028. After transforming TOP10'F competent E. coli (Invitrogen, LaJolla, Calif.) with expression system pHly-ActA-E7, chloramphenicol resistant clones were screened by PCR analysis using the above-described upstream pHly primer and downstream prfA gene primer. A clone containing pHly-ActA-E7 was amplified, and midiprep DNA was isolated (Promega, Madison, Wis). XFL-7 was transformed with pHly-ActA-E7, and clones were selected for the retention of the plasmid in vivo. Clones were grown in brain heart infusion medium (Difco, Detroit, Mich.) with 20 mcg (microgram)/ml (milliliter) chloramphenicol at 37° C. Bacteria were frozen in aliquots at −80° C.

In Vivo Experiments 500 mcL of MATRIGEL®, containing 100 mcL of phosphate buffered saline (PBS) with $2 \times 10^5$ TC-1 tumor cells, plus 400 mcL of MATRIGEL®, (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor Matrigels were removed from the mice and incubated at 4° C. overnight in tubes containing 2 ml RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcL of anti-mouse Fc receptor supernatant (2.4 G2) for 1 hour or overnight at 4° C. Cells were stained for surface molecules CD8 and CD62L, permeabilized, fixed using the permeabilization kit GOLGI-STOP® or GOLGI-PLUG® (Pharmingen, San Diego, Calif.), and stained for IFN-gamma 500,000 events were acquired using two-laser flow cytometer FACSCalibur and analyzed using Cellquest Software (Becton Dickinson, Franklin Lakes, N.J.). Percentages of IFN-gamma secreting cells within the activated ($CD62L^{low}$) $CD8^+$T cells were calculated.

For tetramer staining, $H-2D^b$ tetramer was loaded with phycoerythrin (PE)-conjugated E7 peptide (RAHYNIVTF, SEQ ID NO: 42), stained at rt for 1 hour, and stained with anti-allophycocyanin (APC) conjugated MEL-14 (CD62L) and FITC-conjugated CD8β at 4° C. for 30 min. Cells were analyzed comparing tetramer$^+$CD8$^+$ $CD62L^{low}$ cells in the spleen and in the tumor.

Results

Figure 17:
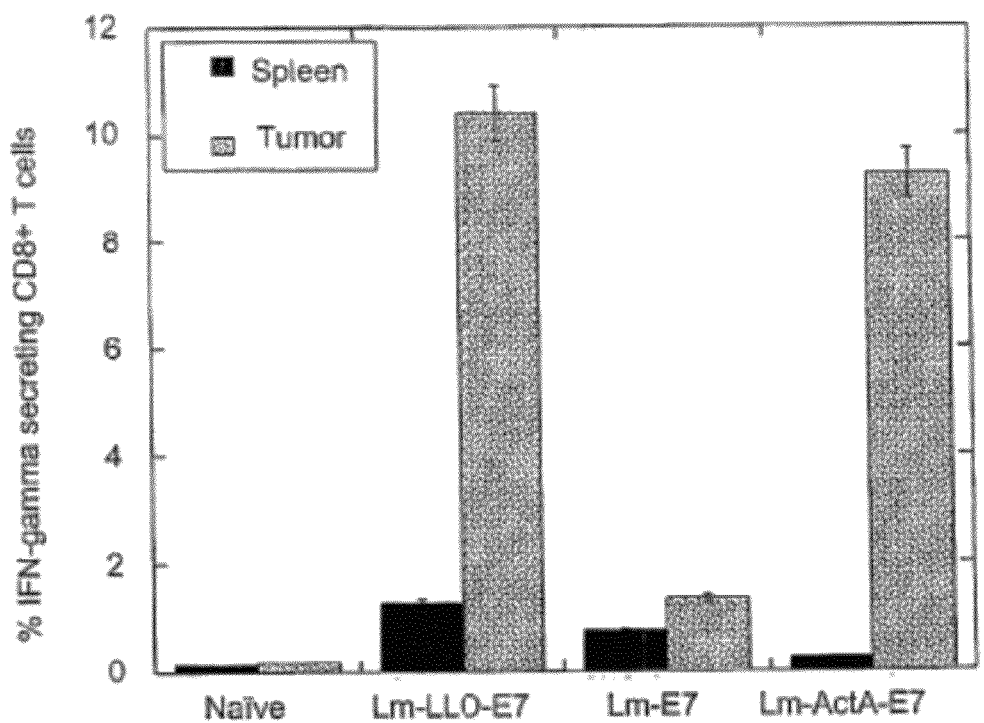
FIG. 17. Depiction of vaccinia virus constructs expressing different forms of HPV16 E7 protein.
Figure 18:
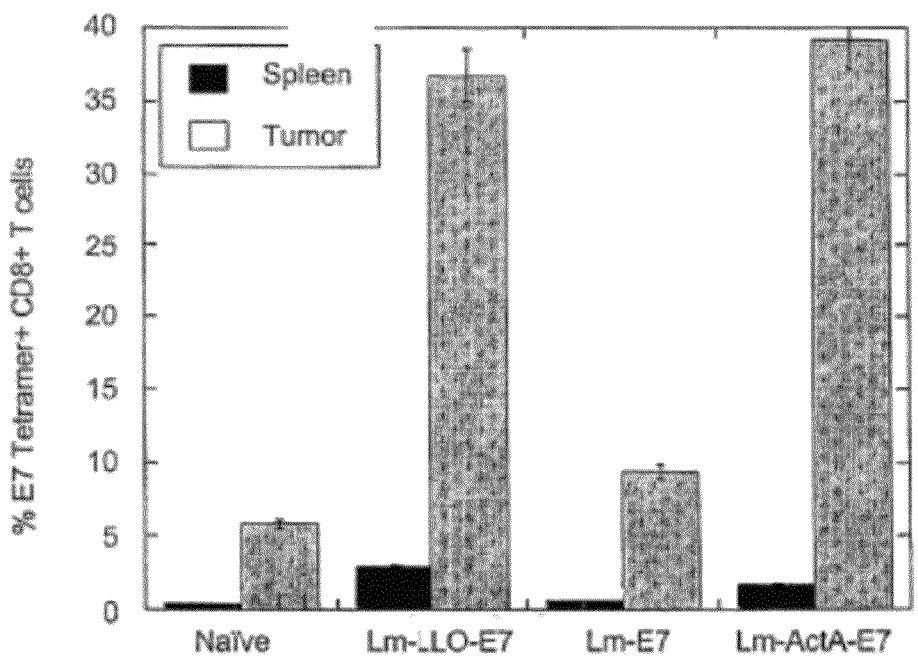
FIG. 18. Induction and penetration of E7 specific CD8+ T cells in the spleens and tumors of mice administered TC-1 cells and subsequently administered a recombinant *Listeria* vaccine (naive, Lm-LLO-E7, Lm-E7, Lm-ActA-E7).

To analyze the ability of LLO and ActA fusions to enhance antigen specific immunity, mice were implanted with TC-1 tumor cells and immunized with either Lm-LLO-E7 ($1 \times 10^7$ CFU), Lm-E7 ($1 \times 10^6$ CFU), or Lm-ActA-E7 ($2 \times 10^8$ CFU), or were untreated (naïve). Tumors of mice from the Lm-LLO-E7 and Lm-ActA-E7 groups contained a higher percentage of IFN-gamma-secreting CD8$^+$ T cells (FIG. 17) and tetramer-specific CD8$^+$ cells (FIG. 18) than in mice administered Lm-E7 or naïve mice.

Thus, Lm-LLO-E7 and Lm-ActA-E7 are both efficacious at induction of tumor-infiltrating CD8$^+$ T cells and tumor regression. Accordingly, LLO and ActA fusions are effective in methods and compositions of the present invention.

Example 8

Fusion to a Pest-Like Sequence Enhances E7-Specific Immunity Materials and Experimental Methods Constructs Lm-PEST-E7, a *Listeria* strain identical to Lm-LLO-E7, except that it contains only the promoter and the first 50 AA of the LLO, was constructed as follows:

The hly promoter and PEST regions were fused to the full-length E7 gene by splicing by overlap extension (SOE) PCR. The E7 gene and the hly-PEST gene fragment were amplified from the plasmid pGG-55, which contains the first 441 amino acids of LLO, and spliced together by conventional PCR techniques. pVS16.5, the hly-PEST-E7 fragment and the LM transcription factor prfA were subcloned into the plasmid pAM401. The resultant plasmid was used to transform XFL-7.

Lm-E7$_{epi}$ is a recombinant strain that secretes E7 without the PEST region or an LLO fragment. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7$_{epi}$ is completely isogenic to Lm-LLO-E7 and Lm-PEST-E7, except for the form of the E7 antigen expressed.

Recombinant strains were grown in brain heart infusion (BHI) medium with chloramphenicol (20 mcg/mL). Bacteria were frozen in aliquots at −80° C.

Results

Figure 19:
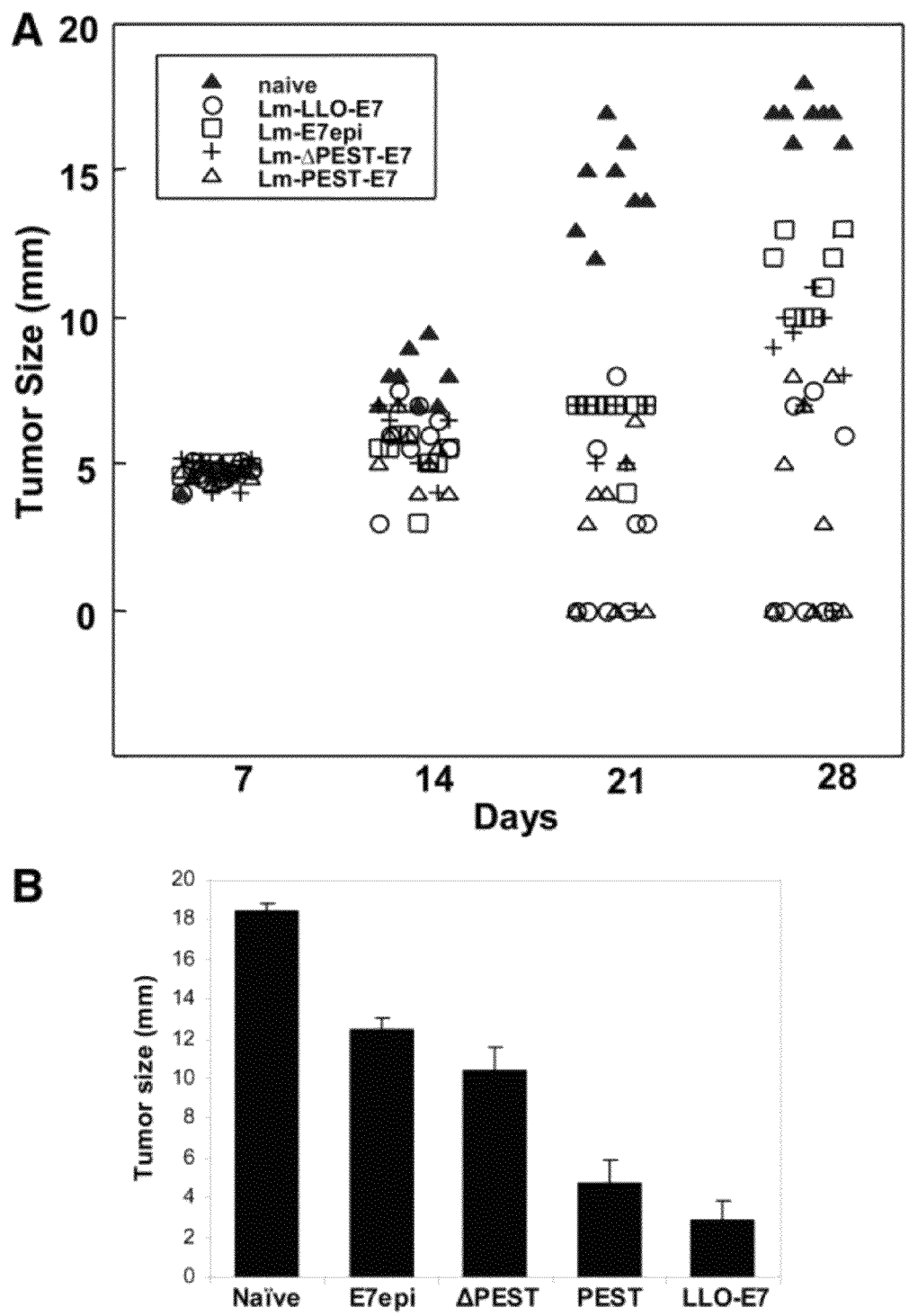
FIG. 19. A. *Listeria* constructs containing PEST regions lead to greater tumor regression. B. average tumor size in mice treated with *Listeria* vaccines.

To test the effect on antigenicity of fusion to a PEST-like sequence, the LLO PEST-like sequence was fused to E7. Tumor regression studies were performed, as described for Example 1, in parallel with *Listeria* strain expressing LLO-E7 and E7 alone. Lm-LLO-E7 and Lm-PEST-E7 caused the regression 5/8 and 3/8 established tumors, respectively (FIG. 19). By contrast, Lm-E7epi only caused tumor regression in 1/8 mice. A statistically significant difference in tumor sizes was observed between tumors treated with PEST-containing constructs (Lm-LLO-E7 or Lm-PEST-E7) and those treated with Lm-E7epi (Student's t test).

Figure 20:
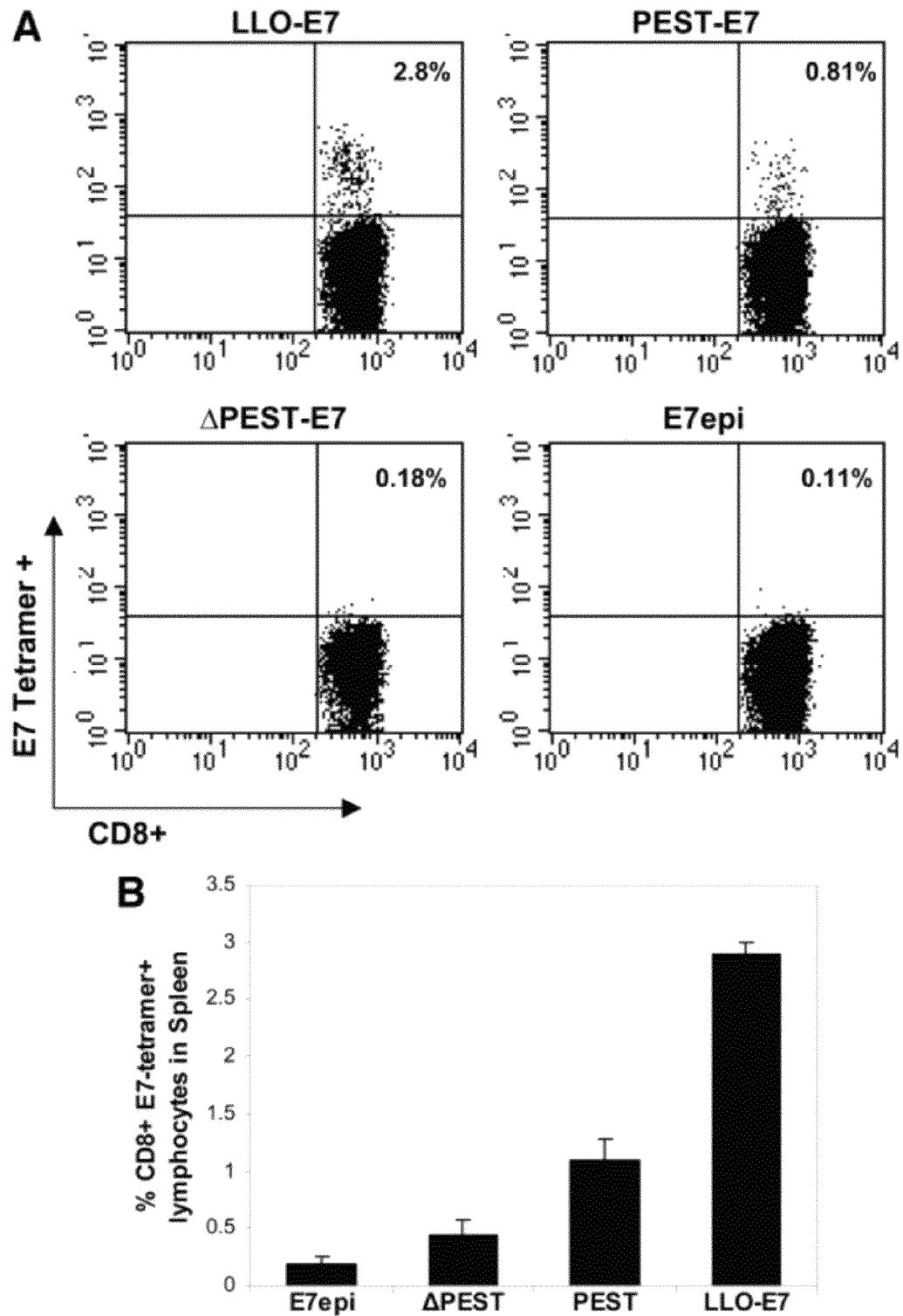
FIG. 20. *Listeria* constructs containing PEST regions induce a higher percentage of E7-specific lymphocytes in the spleen. A. Data from 1 representative experiment. B. Average and SE of data from 3 experiments.
Figure 21:
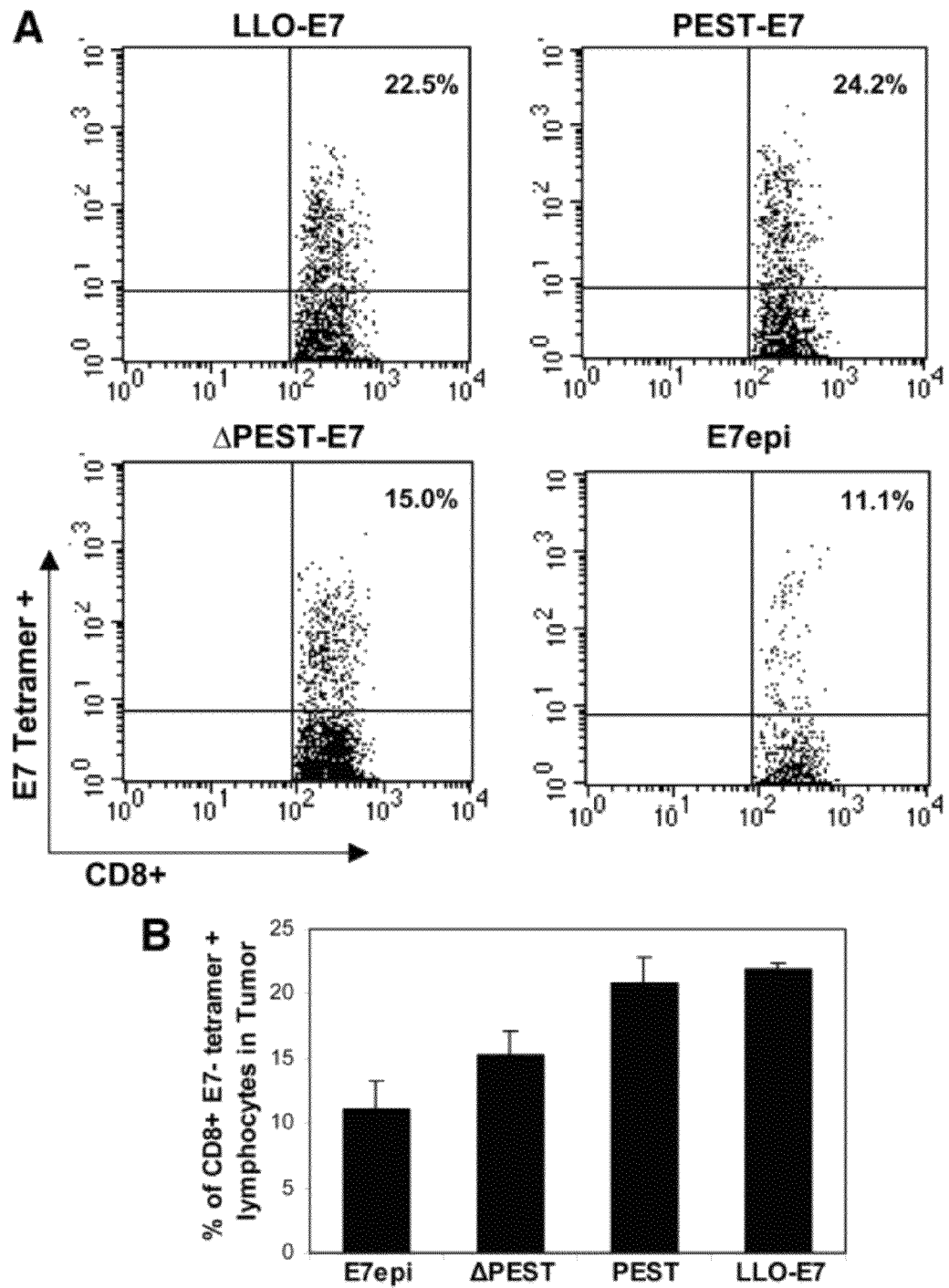
FIG. 21. *Listeria* constructs containing PEST regions induce a higher percentage of E7-specific lymphocytes within the tumor. A. Data from 1 representative experiment. B. Average and SE of data from 3 experiments.

To compare the levels of E7-specific lymphocytes generated by the vaccines in the spleen, spleens were harvested on day 21 and stained with antibodies to CD62L, CD8, and the E7/Db tetramer. Lm-E7epi induced low levels of E7 tetramer-positive activated CD8$^+$ T cells in the spleen, while Lm-PEST-E7 and Lm-LLO-E7 induced 5 and 15 times more cells, respectively (FIG. 20A), a result that was reproducible over 3 separate experiments. Thus, fusion to PEST-like sequences increased induction of tetramer-positive splenocytes. The mean and SE of data obtained from the 3 experiments (FIG. 20B) demonstrate the significant increase in tetramer-positive CD8$^+$ cells by Lm-LLO-E7 and Lm-PEST-E7 over Lm-E7epi (P<0.05 by Student's t test). Similarly, the number of tumor-infiltrating antigen-specific CD8$^+$ T cells was higher in mice vaccinated with Lm-LLO-E7 and Lm-PEST-E7, reproducibly over 3 experiments (FIG. 21A-B). Average values of tetramer-positive CD8$^+$ TILs were significantly higher for Lm-LLO-E7 than Lm-E7epi (P<0.05; Student's t test).

Thus, PEST-like sequences confer increased immunogenicity to antigens.

Example 9

Figure 22:
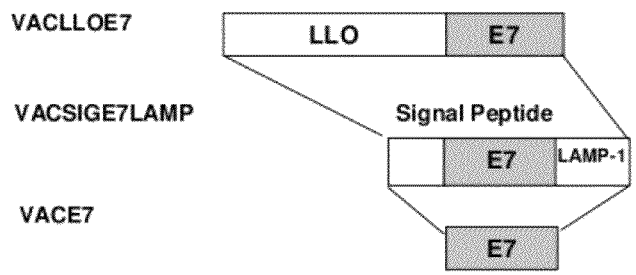
FIG. 22. Depiction of vaccinia virus constructs expressing different forms of HPV16 E7 protein.

Enhancement of Immunogenicity by Fusion of an Antigen to LLO does not Require a Listeria Vector
Materials and Experimental Methods Construction of Vac-SigE7Lamp The WR strain of vaccinia was used as the recipient, and the fusion gene was excised from the Listerial plasmid and inserted into pSC11 under the control of the p75 promoter. This vector was chosen because it is the transfer vector used for the vaccinia constructs Vac-SigE7Lamp and Vac-E7 and therefore allowed direct comparison with Vac-LLO-E7. In this way all 3 vaccinia recombinants were expressed under control of the same early/late compound promoter p7.5. In addition, SC11 allows the selection of recombinant viral plaques to TK selection and beta-galactosidase screening. FIG. 22 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resulting pSC1 1-E7 construct was used to transfect the TK-ve cell line CV1 that had been infected with the wild-type vaccinia strain, WR. Cell lysates obtained from this co-infection/transfection step contain vaccinia recombinants that were plaque-purified 3 times. Expression of the LLO-E7 fusion product by plaque-purified vaccinia was verified by Western blot using an antibody directed against the LLO protein sequence. Ability of Vac-LLO-E7 to produce CD8$^+$ T cells specific to LLO and E7 was determined using the LLO (91-99) and E7 (49-57) epitopes of Balb/c and C57/BL6 mice, respectively. Results were confirmed in a chromium release assay.

Results

Figure 23:
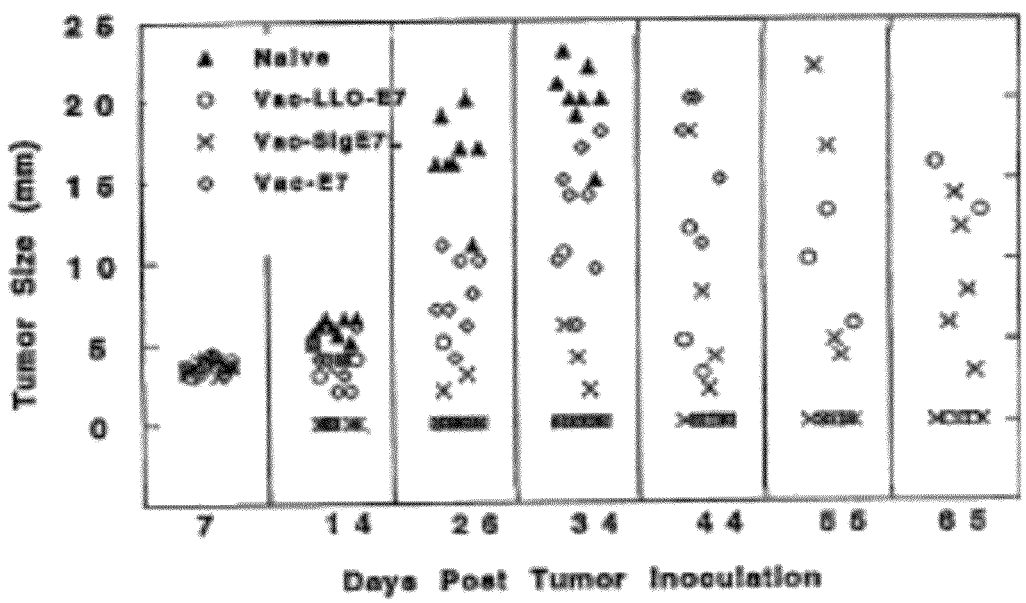
FIG. 23. VacLLOE7 induces long-term regression of tumors established from $2 \times 10^5$ TC-1 cells in C57BL/6 mice. Mice were injected 11 and 18 days after tumor challenge with $10^7$ PFU of VacLLOE7, VacSigE7LAMP-1, or VacE7/mouse i.p. or were left untreated (naive). 8 mice per treatment group were used, and the cross section for each tumor (average of 2 measurements) is shown for the indicated days after tumor inoculation.

To determine whether enhancement of immunogenicity by fusion of an antigen to LLO requires a *Listeria* vector, a vaccinia vector expressing E7 as a fusion protein with a non-hemolytic truncated form of LLO was constructed. Tumor rejection studies were performed with TC-1 as described in above Examples, but initiating treatment when the tumors were 3 mm in diameter (FIG. 23). By day 76, 50% of the Vac-LLO-E7 treated mice were tumor free, while only 25% of the Vac-SigE7Lamp mice were tumor free. In other experiments, LLO-antigen fusions were shown to be more immunogenic than E7 peptide mixed with SBAS2 or unmethylated CpG oligonucleotides in a side-by-side comparison. These results show that (a) LLO-antigen fusions are immunogenic not only in the context of *Listeria*, but also in other contexts; and (b) the immunogenicity of LLO-antigen fusions compares favorably with other vaccine approaches known to be efficacious.

What is claimed is:

1. A method of delaying progression of a breast tumor in a subject, said method comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against a HMW-MAA-expressing pericyte of a vasculature of said tumor, whereby said subject mounts an immune response against said pericyte of said vasculature of said tumor, thereby delaying progression of a breast tumor in a subject.

2. A method of treating, suppressing, or inhibiting a breast cancer in a subject, whereby said breast cancer is associated with expression of HER-2/neu antigen in said subject, said method comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against HER-2/neu-expressing tumor, thereby treating, suppressing, or inhibiting a breast cancer in a subject.

3. A method of inducing a breast anti-tumor immune response in a subject comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against a HMW-MAA-expressing pericyte of a vasculature of said tumor, whereby said composition kills the vasculature of said tumor and induces the release of a tumor antigen, thereby inducing a breast anti-tumor immune response.

4. A method of delaying progression of a breast tumor in a subject, said method comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against a HMW-MAA-expressing pericyte of a vasculature of said tumor, whereby said subject mounts an immune response against a pericyte of a vasculature of said tumor, thereby delaying progression of a breast tumor in a subject.

5. A method of treating, suppressing, or inhibiting a breast cancer in a subject, whereby said cancer is associated with expression of HER-2/neu antigen in a subject, said method comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against a HMW-MAA-expressing pericyte of a vasculature of a tumor from said cancer, thereby treating, suppressing, or inhibiting a breast cancer in a subject.

6. A method of inducing a breast anti-tumor immune response in a subject comprising the step of administering to said subject a composition comprising a recombinant *Listeria* strain expressing a recombinant nucleotide sequence encoding a recombinant polypeptide comprising a fragment of a High Molecular Weight Melanoma-Associated Antigen (HMW-MAA) protein fused to a listeriolysin (LLO) protein, an ActA protein, or a PEST sequence, wherein said recombinant nucleotide sequence encoding said fragment is selected from the group consisting of SEQ ID NOs 21, 22, or 23, whereby said subject mounts an immune response against a HMW-MAA-expressing pericyte of a vasculature of said tumor, whereby said composition kills the vasculature of said tumor and induces the release of a tumor antigen, thereby inducing a breast anti-tumor immune response.

7. A method for treating breast tumor cells expressing HER-2/neu in a subject, said method comprising administering to said subject a composition comprising a recombinant *Listeria* strain expressing a nucleotide sequence encoding a recombinant polypeptide, said recombinant nucleotide sequence is encoded by SEQ ID NO: 23 linked to an LLO polypeptide.

* * * * *

SEQUENCE LISTING

<160> NUMBER OF SEQ ID NOS: 48

<210> SEQ ID NO 1
<211> LENGTH: 529
<212> TYPE: PRT
<213> ORGANISM: Listeria monocytogenes

<400> SEQUENCE: 1

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                      70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
        210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Ser Lys Ala Tyr Thr Asp
            405                 410                 415

Gly Lys Ile Asn Ile Asp His Ser Gly Gly Tyr Val Ala Gln Phe Asn
```

```
                     420              425              430
Ile Ser Trp Asp Glu Val Asn Tyr Asp Pro Glu Gly Asn Glu Ile Val
        435              440              445

Gln His Lys Asn Trp Ser Glu Asn Asn Lys Ser Lys Leu Ala His Phe
    450              455              460

Thr Ser Ser Ile Tyr Leu Pro Gly Asn Ala Arg Asn Ile Asn Val Tyr
465              470              475              480

Ala Lys Glu Cys Thr Gly Leu Ala Trp Glu Trp Trp Arg Thr Val Ile
            485              490              495

Asp Asp Arg Asn Leu Pro Leu Val Lys Asn Arg Asn Ile Ser Ile Trp
        500              505              510

Gly Thr Thr Leu Tyr Pro Lys Tyr Ser Asn Lys Val Asp Asn Pro Ile
        515              520              525

Glu

<210> SEQ ID NO 2
<211> LENGTH: 441
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Ala Ser Pro Pro Ala Ser
        35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270
```

```
Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
        420                 425                 430

Ile Ser Trp Asp Glu Val Asn Tyr Asp
        435                 440

<210> SEQ ID NO 3
<211> LENGTH: 416
<212> TYPE: PRT
<213> ORGANISM: Listeria monocytogenes

<400> SEQUENCE: 3

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205
```

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 4
<211> LENGTH: 390
<212> TYPE: PRT
<213> ORGANISM: Listeria monocytogenes

<400> SEQUENCE: 4

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Lys Val Ala Lys Glu Ser Val Ala
                165                 170                 175

```
Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
                275                 280                 285

Pro Ser Ser Phe Glu Phe Pro Pro Pro Thr Asp Glu Glu Leu Arg
        290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Glu Leu Asn
    370                 375                 380

Gly Arg Gly Gly Arg Pro
385                 390

<210> SEQ ID NO 5
<211> LENGTH: 1170
<212> TYPE: DNA
<213> ORGANISM: Listeria monocytogenes

<400> SEQUENCE: 5
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata aagtgagaaa tacgaacaaa     240
gcagacctaa tagcaatgtt gaaagaaaaa gcagaaaaag gtccaaatat caataataac     300
aacagtgaac aaaactgagaa tgcggctata atgaagagg cttcaggagc cgaccgacca     360
gctatacaag tggagcgtcg tcatccagga ttgccatcgg atagcgcagc ggaaattaaa     420
aaaagaagga aagccatagc atcatcggat agtgagcttg aaagccttac ttatccggat     480
aaaccaacaa aagtaaataa gaaaaaagtg gcgaaagagt cagttgcgga tgcttctgaa     540
agtgacttag attctagcat gcagtcagca gatgagtctt cacccaaacc tttaaaagca     600
aaccaacaac attttttccc taaagtattt aaaaaaataa agatgcgggg gaaatgggta     660
cgtgataaaa tcgacgaaaa tcctgaagta agaaagcga ttgttgataa agtgcaggg      720 ttaattgacc aattattaac caaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat ttccaccacc acctacggat     900
```

-continued

```
gaagagttaa gacttgcttt gccagagacg ccaatgcttc ttggttttaa tgctcctgct    960
acatcggaac cgagctcgtt cgaatttcca ccgcctccaa cagaagatga actagaaatc    1020
atccgggaaa cagcatcctc gctagattct agttttacaa gagggatttt agctagtttg    1080
agaaatgcta ttaatcgcca tagtcaaaat ttctctgatt tcccaccaat cccaacagaa    1140
gaagagttga acgggagagg cggtagacca                                      1170
```

<210> SEQ ID NO 6
<211> LENGTH: 32
<212> TYPE: PRT
<213> ORGANISM: Listeria monocytogenes

<400> SEQUENCE: 6

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 7
<211> LENGTH: 19
<212> TYPE: PRT
<213> ORGANISM: Listeria monocytogenes

<400> SEQUENCE: 7

Lys Glu Asn Ser Ile Ser Ser Met Ala Pro Pro Ala Ser Pro Pro Ala
1               5                   10                  15

Ser Pro Lys

<210> SEQ ID NO 8
<211> LENGTH: 14
<212> TYPE: PRT
<213> ORGANISM: Listeria monocytogenes

<400> SEQUENCE: 8

Lys Thr Glu Glu Gln Pro Ser Glu Val Asn Thr Gly Pro Arg
1               5                   10

<210> SEQ ID NO 9
<211> LENGTH: 28
<212> TYPE: PRT
<213> ORGANISM: Listeria monocytogenes

<400> SEQUENCE: 9

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 10
<211> LENGTH: 20
<212> TYPE: PRT
<213> ORGANISM: Listeria monocytogenes

<400> SEQUENCE: 10

Lys Asn Glu Glu Val Asn Ala Ser Asp Phe Pro Pro Pro Pro Thr Asp
1               5                   10                  15

Glu Glu Leu Arg
            20

<210> SEQ ID NO 11
<211> LENGTH: 33

```
<212> TYPE: PRT
<213> ORGANISM: Listeria monocytogenes

<400> SEQUENCE: 11

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 12
<211> LENGTH: 19
<212> TYPE: PRT
<213> ORGANISM: Listeria seeligeri

<400> SEQUENCE: 12

Arg Ser Glu Val Thr Ile Ser Pro Ala Glu Thr Pro Glu Ser Pro Pro
1               5                   10                  15

Ala Thr Pro

<210> SEQ ID NO 13
<211> LENGTH: 17
<212> TYPE: PRT
<213> ORGANISM: Streptococcus pyogenes

<400> SEQUENCE: 13

Lys Gln Asn Thr Ala Ser Thr Glu Thr Thr Thr Thr Asn Glu Gln Pro
1               5                   10                  15

Lys

<210> SEQ ID NO 14
<211> LENGTH: 17
<212> TYPE: PRT
<213> ORGANISM: Streptococcus equisimilis

<400> SEQUENCE: 14

Lys Gln Asn Thr Ala Asn Thr Glu Thr Thr Thr Thr Asn Glu Gln Pro
1               5                   10                  15

Lys

<210> SEQ ID NO 15
<211> LENGTH: 2322
<212> TYPE: PRT
<213> ORGANISM: Homo sapiens

<400> SEQUENCE: 15

Met Gln Ser Gly Arg Gly Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110
```

```
Val Leu Thr Val Val Glu Gly Trp Ala Thr Leu Ser Val Asp Gly Phe
            115                 120                 125
Leu Asn Ala Ser Ser Ala Val Pro Gly Ala Pro Leu Glu Val Pro Tyr
        130                 135                 140
Gly Leu Phe Val Gly Thr Gly Thr Leu Gly Leu Pro Tyr Leu Arg
145                 150                 155                 160
Gly Thr Ser Arg Pro Leu Arg Gly Cys Leu His Ala Ala Thr Leu Asn
                165                 170                 175
Gly Arg Ser Leu Leu Arg Pro Leu Thr Pro Asp Val His Glu Gly Cys
            180                 185                 190
Ala Glu Glu Phe Ser Ala Ser Asp Val Ala Leu Gly Phe Ser Gly
        195                 200                 205
Pro His Ser Leu Ala Ala Phe Pro Ala Trp Gly Thr Gln Asp Glu Gly
        210                 215                 220
Thr Leu Glu Phe Thr Leu Thr Thr Gln Ser Arg Gln Ala Pro Leu Ala
225                 230                 235                 240
Phe Gln Ala Gly Gly Arg Arg Gly Asp Phe Ile Tyr Val Asp Ile Phe
                245                 250                 255
Glu Gly His Leu Arg Ala Val Val Glu Lys Gly Gln Gly Thr Val Leu
            260                 265                 270
Leu His Asn Ser Val Pro Val Ala Asp Gly Gln Pro His Glu Val Ser
        275                 280                 285
Val His Ile Asn Ala His Arg Leu Glu Ile Ser Val Asp Gln Tyr Pro
    290                 295                 300
Thr His Thr Ser Asn Arg Gly Val Leu Ser Tyr Leu Glu Pro Arg Gly
305                 310                 315                 320
Ser Leu Leu Leu Gly Gly Leu Asp Ala Glu Ala Ser Arg His Leu Gln
                325                 330                 335
Glu His Arg Leu Gly Leu Thr Pro Glu Ala Thr Asn Ala Ser Leu Leu
            340                 345                 350
Gly Cys Met Glu Asp Leu Ser Val Asn Gly Gln Arg Arg Gly Leu Arg
        355                 360                 365
Glu Ala Leu Leu Thr Arg Asn Met Ala Ala Gly Cys Arg Leu Glu Glu
        370                 375                 380
Glu Glu Tyr Glu Asp Asp Ala Tyr Gly His Tyr Glu Ala Phe Ser Thr
385                 390                 395                 400
Leu Ala Pro Glu Ala Trp Pro Ala Met Glu Leu Pro Glu Pro Cys Val
                405                 410                 415
Pro Glu Pro Gly Leu Pro Pro Val Phe Ala Asn Phe Thr Gln Leu Leu
            420                 425                 430
Thr Ile Ser Pro Leu Val Val Ala Glu Gly Gly Thr Ala Trp Leu Glu
        435                 440                 445
Trp Arg His Val Gln Pro Thr Leu Asp Leu Met Glu Ala Glu Leu Arg
        450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
            500                 505                 510
Asp Thr Ser Asp Gln Leu Val Leu Glu Val Ser Val Thr Ala Arg Val
        515                 520                 525
Pro Met Pro Ser Cys Leu Arg Arg Gly Gln Thr Tyr Leu Leu Pro Ile
```

```
                530                 535                 540
Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
                580                 585                 590

Gln Val Leu Gly Thr Ser Ser Gly Leu Pro Val Glu Arg Arg Asp Gln
                595                 600                 605

Pro Gly Glu Pro Ala Thr Glu Phe Ser Cys Arg Glu Leu Glu Ala Gly
                610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
                660                 665                 670

Leu Ala Gln Gly Ser Ala Met Pro Ile Leu Pro Ala Asn Leu Ser Val
                675                 680                 685

Glu Thr Asn Ala Val Gly Gln Asp Val Ser Val Leu Phe Arg Val Thr
690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
                740                 745                 750

Tyr Asp Thr Val Glu Asn Leu Ala Leu Glu Val Gln Val Gly Gln Glu
                755                 760                 765

Ile Leu Ser Asn Leu Ser Phe Pro Val Thr Ile Gln Arg Ala Thr Val
770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
                820                 825                 830

Asn Leu Gln Leu Gln Gly Thr Arg Leu Ser Asp Gly Gln Gly Phe Thr
                835                 840                 845

Gln Asp Asp Ile Gln Ala Gly Arg Val Thr Tyr Gly Ala Thr Ala Arg
850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
                900                 905                 910

Gly Glu Gly Val Leu Ser Ala Asp His Leu Phe Val Lys Ser Leu Asn
                915                 920                 925

Ser Ala Ser Tyr Leu Tyr Glu Val Met Glu Arg Pro Arg His Gly Arg
                930                 935                 940

Leu Ala Trp Arg Gly Thr Gln Asp Lys Thr Thr Met Val Thr Ser Phe
945                 950                 955                 960
```

-continued

Thr Asn Glu Asp Leu Leu Arg Gly Arg Leu Val Tyr Gln His Asp Asp
            965                 970                 975

Ser Glu Thr Thr Glu Asp Asp Ile Pro Phe Val Ala Thr Arg Gln Gly
        980                 985                 990

Glu Ser Ser Gly Asp Met Ala Trp Glu Glu Val Arg Gly Val Phe Arg
        995                 1000                1005

Val Ala Ile Gln Pro Val Asn Asp His Ala Pro Val Gln Thr Ile
    1010            1015            1020

Ser Arg Ile Phe His Val Ala Arg Gly Gly Arg Leu Leu Thr
    1025            1030            1035

Thr Asp Asp Val Ala Phe Ser Asp Ala Asp Ser Gly Phe Ala Asp
    1040            1045            1050

Ala Gln Leu Val Leu Thr Arg Lys Asp Leu Leu Phe Gly Ser Ile
    1055            1060            1065

Val Ala Val Asp Glu Pro Thr Arg Pro Ile Tyr Arg Phe Thr Gln
    1070            1075            1080

Glu Asp Leu Arg Lys Arg Arg Val Leu Phe Val His Ser Gly Ala
    1085            1090            1095

Asp Arg Gly Trp Ile Gln Leu Gln Val Ser Asp Gly Gln His Gln
    1100            1105            1110

Ala Thr Ala Leu Leu Glu Val Gln Ala Ser Glu Pro Tyr Leu Arg
    1115            1120            1125

Val Ala Asn Gly Ser Ser Leu Val Val Pro Gln Gly Gly Gln Gly
    1130            1135            1140

Thr Ile Asp Thr Ala Val Leu His Leu Asp Thr Asn Leu Asp Ile
    1145            1150            1155

Arg Ser Gly Asp Glu Val His Tyr His Val Thr Ala Gly Pro Arg
    1160            1165            1170

Trp Gly Gln Leu Val Arg Ala Gly Gln Pro Ala Thr Ala Phe Ser
    1175            1180            1185

Gln Gln Asp Leu Leu Asp Gly Ala Val Leu Tyr Ser His Asn Gly
    1190            1195            1200

Ser Leu Ser Pro Arg Asp Thr Met Ala Phe Ser Val Glu Ala Gly
    1205            1210            1215

Pro Val His Thr Asp Ala Thr Leu Gln Val Thr Ile Ala Leu Glu
    1220            1225            1230

Gly Pro Leu Ala Pro Leu Lys Leu Val Arg His Lys Lys Ile Tyr
    1235            1240            1245

Val Phe Gln Gly Glu Ala Ala Glu Ile Arg Arg Asp Gln Leu Glu
    1250            1255            1260

Ala Ala Gln Glu Ala Val Pro Pro Ala Asp Ile Val Phe Ser Val
    1265            1270            1275

Lys Ser Pro Pro Ser Ala Gly Tyr Leu Val Met Val Ser Arg Gly
    1280            1285            1290

Ala Leu Ala Asp Glu Pro Pro Ser Leu Asp Pro Val Gln Ser Phe
    1295            1300            1305

Ser Gln Glu Ala Val Asp Thr Gly Arg Val Leu Tyr Leu His Ser
    1310            1315            1320

Arg Pro Glu Ala Trp Ser Asp Ala Phe Ser Leu Asp Val Ala Ser
    1325            1330            1335

Gly Leu Gly Ala Pro Leu Glu Gly Val Leu Val Glu Leu Glu Val
    1340            1345            1350

Leu Pro Ala Ala Ile Pro Leu Glu Ala Gln Asn Phe Ser Val Pro
    1355            1360            1365

```
Glu Gly Gly Ser Leu Thr Leu Ala Pro Pro Leu Arg Val Ser
    1370            1375            1380

Gly Pro Tyr Phe Pro Thr Leu Leu Gly Leu Ser Leu Gln Val Leu
    1385            1390            1395

Glu Pro Pro Gln His Gly Ala Leu Gln Lys Glu Asp Gly Pro Gln
    1400            1405            1410

Ala Arg Thr Leu Ser Ala Phe Ser Trp Arg Met Val Glu Glu Gln
    1415            1420            1425

Leu Ile Arg Tyr Val His Asp Gly Ser Glu Thr Leu Thr Asp Ser
    1430            1435            1440

Phe Val Leu Met Ala Asn Ala Ser Glu Met Asp Arg Gln Ser His
    1445            1450            1455

Pro Val Ala Phe Thr Val Thr Val Leu Pro Val Asn Asp Gln Pro
    1460            1465            1470

Pro Ile Leu Thr Thr Asn Thr Gly Leu Gln Met Trp Glu Gly Ala
    1475            1480            1485

Thr Ala Pro Ile Pro Ala Glu Ala Leu Arg Ser Thr Asp Gly Asp
    1490            1495            1500

Ser Gly Ser Glu Asp Leu Val Tyr Thr Ile Glu Gln Pro Ser Asn
    1505            1510            1515

Gly Arg Val Val Leu Arg Gly Ala Pro Gly Thr Glu Val Arg Ser
    1520            1525            1530

Phe Thr Gln Ala Gln Leu Asp Gly Gly Leu Val Leu Phe Ser His
    1535            1540            1545

Arg Gly Thr Leu Asp Gly Gly Phe Arg Phe Arg Leu Ser Asp Gly
    1550            1555            1560

Glu His Thr Ser Pro Gly His Phe Phe Arg Val Thr Ala Gln Lys
    1565            1570            1575

Gln Val Leu Leu Ser Leu Lys Gly Ser Gln Thr Leu Thr Val Cys
    1580            1585            1590

Pro Gly Ser Val Gln Pro Leu Ser Ser Gln Thr Leu Arg Ala Ser
    1595            1600            1605

Ser Ser Ala Gly Thr Asp Pro Gln Leu Leu Leu Tyr Arg Val Val
    1610            1615            1620

Arg Gly Pro Gln Leu Gly Arg Leu Phe His Ala Gln Gln Asp Ser
    1625            1630            1635

Thr Gly Glu Ala Leu Val Asn Phe Thr Gln Ala Glu Val Tyr Ala
    1640            1645            1650

Gly Asn Ile Leu Tyr Glu His Glu Met Pro Pro Glu Pro Phe Trp
    1655            1660            1665

Glu Ala His Asp Thr Leu Glu Leu Gln Leu Ser Ser Pro Pro Ala
    1670            1675            1680

Arg Asp Val Ala Ala Thr Leu Ala Val Ala Val Ser Phe Glu Ala
    1685            1690            1695

Ala Cys Pro Gln Arg Pro Ser His Leu Trp Lys Asn Lys Gly Leu
    1700            1705            1710

Trp Val Pro Glu Gly Gln Arg Ala Arg Ile Thr Val Ala Ala Leu
    1715            1720            1725

Asp Ala Ser Asn Leu Leu Ala Ser Val Pro Ser Pro Gln Arg Ser
    1730            1735            1740

Glu His Asp Val Leu Phe Gln Val Thr Gln Phe Pro Ser Arg Gly
    1745            1750            1755

Gln Leu Leu Val Ser Glu Glu Pro Leu His Ala Gly Gln Pro His
```

-continued

```
            1760                1765                1770

Phe Leu Gln Ser Gln Leu Ala  Ala Gly Gln Leu Val  Tyr Ala His
    1775                1780                1785

Gly Gly Gly Gly Thr Gln Gln  Asp Gly Phe His Phe  Arg Ala His
    1790                1795                1800

Leu Gln Gly Pro Ala Gly Ala  Ser Val Ala Gly Pro  Gln Thr Ser
    1805                1810                1815

Glu Ala Phe Ala Ile Thr Val  Arg Asp Val Asn Glu  Arg Pro Pro
    1820                1825                1830

Gln Pro Gln Ala Ser Val Pro  Leu Arg Leu Thr Arg  Gly Ser Arg
    1835                1840                1845

Ala Pro Ile Ser Arg Ala Gln  Leu Ser Val Val Asp  Pro Asp Ser
    1850                1855                1860

Ala Pro Gly Glu Ile Glu Tyr  Glu Val Gln Arg Ala  Pro His Asn
    1865                1870                1875

Gly Phe Leu Ser Leu Val Gly  Gly Leu Gly Pro Val  Thr Arg
    1880                1885                1890

Phe Thr Gln Ala Asp Val Asp  Ser Gly Arg Leu Ala  Phe Val Ala
    1895                1900                1905

Asn Gly Ser Ser Val Ala Gly  Ile Phe Gln Leu Ser  Met Ser Asp
    1910                1915                1920

Gly Ala Ser Pro Pro Leu Pro  Met Ser Leu Ala Val  Asp Ile Leu
    1925                1930                1935

Pro Ser Ala Ile Glu Val Gln  Leu Arg Ala Pro Leu  Glu Val Pro
    1940                1945                1950

Gln Ala Leu Gly Arg Ser Ser  Leu Ser Gln Gln Gln  Leu Arg Val
    1955                1960                1965

Val Ser Asp Arg Glu Glu Pro  Glu Ala Ala Tyr Arg  Leu Ile Gln
    1970                1975                1980

Gly Pro Gln Tyr Gly His Leu  Leu Val Gly Gly Arg  Pro Thr Ser
    1985                1990                1995

Ala Phe Ser Gln Phe Gln Ile  Asp Gln Gly Glu Val  Val Phe Ala
    2000                2005                2010

Phe Thr Asn Phe Ser Ser Ser  His Asp His Phe Arg  Val Leu Ala
    2015                2020                2025

Leu Ala Arg Gly Val Asn Ala  Ser Ala Val Val Asn  Val Thr Val
    2030                2035                2040

Arg Ala Leu Leu His Val Trp  Ala Gly Gly Pro Trp  Pro Gln Gly
    2045                2050                2055

Ala Thr Leu Arg Leu Asp Pro  Thr Val Leu Asp Ala  Gly Glu Leu
    2060                2065                2070

Ala Asn Arg Thr Gly Ser Val  Pro Arg Phe Arg Leu  Leu Glu Gly
    2075                2080                2085

Pro Arg His Gly Arg Val Val  Arg Val Pro Arg Ala  Arg Thr Glu
    2090                2095                2100

Pro Gly Gly Ser Gln Leu Val  Glu Gln Phe Thr Gln  Gln Asp Leu
    2105                2110                2115

Glu Asp Gly Arg Leu Gly Leu  Glu Val Gly Arg Pro  Glu Gly Arg
    2120                2125                2130

Ala Pro Gly Pro Ala Gly Asp  Ser Leu Thr Leu Glu  Leu Trp Ala
    2135                2140                2145

Gln Gly Val Pro Pro Ala Val  Ala Ser Leu Asp Phe  Ala Thr Glu
    2150                2155                2160
```

-continued

| | | | | | | | | | |
|---|---|---|---|---|---|---|---|---|---|
| Pro | Tyr | Asn | Ala | Ala | Arg | Pro | Tyr | Ser | Val | Ala | Leu | Leu | Ser | Val |
| | 2165 | | | | 2170 | | | | 2175 |

Pro Tyr Asn Ala Ala Arg Pro Tyr Ser Val Ala Leu Leu Ser Val
    2165                2170                2175

Pro Glu Ala Ala Arg Thr Glu Ala Gly Lys Pro Glu Ser Ser Thr
    2180                2185                2190

Pro Thr Gly Glu Pro Gly Pro Met Ala Ser Ser Pro Glu Pro Ala
    2195                2200                2205

Val Ala Lys Gly Gly Phe Leu Ser Phe Leu Glu Ala Asn Met Phe
    2210                2215                2220

Ser Val Ile Ile Pro Met Cys Leu Val Leu Leu Leu Ala Leu
    2225                2230                2235

Ile Leu Pro Leu Leu Phe Tyr Leu Arg Lys Arg Asn Lys Thr Gly
    2240                2245                2250

Lys His Asp Val Gln Val Leu Thr Ala Lys Pro Arg Asn Gly Leu
    2255                2260                2265

Ala Gly Asp Thr Glu Thr Phe Arg Lys Val Glu Pro Gly Gln Ala
    2270                2275                2280

Ile Pro Leu Thr Ala Val Pro Gly Gln Gly Pro Pro Pro Gly Gly
    2285                2290                2295

Gln Pro Asp Pro Glu Leu Leu Gln Phe Cys Arg Thr Pro Asn Pro
    2300                2305                2310

Ala Leu Lys Asn Gly Gln Tyr Trp Val
    2315                2320

<210> SEQ ID NO 16
<211> LENGTH: 7011
<212> TYPE: DNA
<213> ORGANISM: Homo sapiens

<400> SEQUENCE: 16

```
atgcagtccg gccgcggccc cccacttcca gccccggcc tggccttggc tttgaccctg      60
actatgttgg ccagacttgc atccgcggct tccttcttcg gtgagaacca cctggaggtg     120
cctgtggcca cggctctgac cgacatagac ctgcagctgc agttctccac gtcccagccc     180
gaagccctcc ttctcctggc agcaggccca gctgaccacc tcctgctgca gctctactct     240
ggacgcctgc aggtcagact tgttctgggc caggaggagc tgaggctgca gactccagca     300
gagacgctgc tgagtgactc catccccac actgtggtgc tgactgtcgt agagggctgg     360
gccacgttgt cagtcgatgg gttttctgaac gcctcctcag cagtcccagg agccccccta     420
gaggtcccct atgggctctt tgttgggggc actgggaccc ttggcctgcc ctacctgagg     480
ggaaccagcc gaccctgag gggttgcctc catgcagcca cctcaatgg ccgcagcctc     540
ctccggcctc tgaccccga tgtgcatgag ggctgtgctg aagagttttc tgccagtgat     600
gatgtggccc tgggcttctc tgggccccac tctctggctg ccttccctgc ctggggcact     660
caggacgaag gaaccctaga gtttacactc accacacaga gccggcaggc acccttggcc     720
ttccaggcag ggggccggcg tgggacttc atctatgtgg acatatttga gggccacctg     780
cgggccgtgg tggagaaggg ccagggtacc gtattgctcc acaacagtgt gcctgtggcc     840
gatgggcagc ccatgaggt cagtgtccac atcaatgctc accggctgga aatctccgtg     900
gaccagtacc ctacgcatac ttcgaaccga ggagtcctca gctacctgga gccacggggc     960
agtctccttc tcgggggggct ggatgcagag gcctctcgtc acctccagga cacccgcctg    1020
ggcctgacac cagaggccac caatgcctcc ctgctgggct gcatggaaga cctcagtgtc    1080
aatggccaga ggcgggggct gcgggaagct ttgctgacgc gcaacatggc agccggctgc    1140
aggctggagg aggaggagta tgaggacgat gcctatggac attatgaagc tttctccacc    1200
```

```
ctggccctg aggcttggcc agccatggag ctgcctgagc catgcgtgcc tgagccaggg    1260
ctgcctcctg tctttgccaa tttcacccag ctgctgacta tcagcccact ggtggtggcc    1320 gagggggca cagcctggct tgagtggagg catgtgcagc ccacgctgga cctgatggag    1380
gctgagctgc gcaaatccca ggtgctgttc agcgtgaccc gaggggcacg ccatggcgag    1440
ctcgagctgg acatcccggg agcccaggca cgaaaaatgt tcaccctcct ggacgtggtg    1500
aaccgcaagg cccgcttcat ccacgatggc tctgaggaca cctccgacca gctggtgctg    1560
gaggtgtcgg tgacggctcg ggtgcccatg ccctcatgcc ttcggagggg ccaaacatac    1620
ctcctgccca tccaggtcaa ccctgtcaat gacccacccc acatcatctt cccacatggc    1680
agcctcatgg tgatcctgga acacacgcag aagccgctgg ggcctgaggt tttccaggcc    1740
tatgacccgg actctgcctg tgagggcctc accttccagg tccttggcac ctcctctggc    1800
ctccccgtgg agcgccgaga ccagcctggg gagccggcga ccgagttctc ctgccgggag    1860
ttggaggccg gcagcctagt ctatgtccac cgcggtggtc ctgcacagga cttgacgttc    1920
cgggtcagcg atggactgca ggccagcccc ccggccacgc tgaaggtggt ggccatccgg    1980
ccggccatac agatccaccg cagcacaggg ttgcgactgg cccaaggctc tgccatgccc    2040
atcttgcccg ccaacctgtc ggtggagacc aatgccgtgg ggcaggatgt gagcgtgctg    2100
ttccgcgtca ctggggccct gcagtttggg gagctgcaga agcaggggc aggtggggtg    2160 gagggtgctg agtggtgggc cacacaggcg ttccaccagc gggatgtgga gcagggccgc    2220
gtgaggtacc tgagcactga cccacagcac cacgcttacg acaccgtgga aacctggcc    2280 ctggaggtgc aggtgggcca ggagatcctg agcaatctgt ccttcccagt gaccatccag    2340
agagccactg tgtggatgct gcggctggag ccactgcaca ctcagaacac ccagcaggag    2400
accctcacca cagcccacct ggaggccacc ctggaggagg caggcccaag ccccccaacc    2460
ttccattatg aggtggttca ggctcccagg aaaggcaacc ttcaactaca gggcacaagg    2520
ctgtcagatg ccagggcttc acccaggat gacatacagg ctggccgggt gacctatggg    2580
gccacagcac gtgcctcaga ggcagtcgag gacaccttcc gtttccgtgt cacagctcca    2640
ccatatttct ccccactcta taccttcccc atccacattg gtggtgaccc agatgcgcct    2700
gtcctcacca atgtcctcct cgtggtgcct gagggtggtg agggtgtcct ctctgctgac    2760
cacctctttg tcaagagtct caacagtgcc agctacctct atgaggtcat ggagcggccc    2820
cgccatggga ggttggcttg gcgtgggaca caggacaaga ccactatggt gacatccttc    2880
accaatgaag acctgttgcg tggccggctg gtctaccagc atgatgactc cgagaccaca    2940
gaagatgata tcccatttgt tgctacccgc cagggcgaga gcagtggtga catggcctgg    3000
gaggaggtac ggggtgtctt ccgagtggcc atccagcccg tgaatgacca cgcccctgtg    3060
cagaccatca gccggatctt ccatgtggcc cggggtgggc ggcggctgct gactacagac    3120
gacgtggcct tcagcgatgc tgactcgggc tttgctgacg cccagctggt gcttacccgc    3180
aaggacctcc tctttggcag tatcgtggcc gtagatgagc ccacgcggcc catctaccgc    3240
ttcacccagg aggacctcag gaagaggcga gtactgttcg tgcactcagg gctgaccgt    3300 ggctggatcc agctgcaggt gtccgacggg caacaccagg ccactgcgct gctggaggtg    3360
caggcctcgg aaccctacct ccgtgtgcc aacggctcca gccttgtggt ccctcaaggg    3420 gccagggca ccatcgacac ggccgtgctc cacctggaca ccaacctcga catccgcagt    3480
ggggatgagg tccactacca cgtcacagct ggccctcgct ggggacagct agtccgggct    3540
ggtcagccag ccacagcctt ctcccagcag gacctgctgg atgggccgt tctctatagc    3600
```

```
cacaatggca gcctcagccc ccgcgacacc atggccttct ccgtggaagc agggccagtg    3660
cacacggatg ccaccctaca agtgaccatt gccctagagg gcccactggc cccactgaag    3720
ctggtccggc acaagaagat ctacgtcttc cagggagagg cagctgagat cagaagggac    3780
cagctggagg cagcccagga ggcagtgcca cctgcagaca tcgtattctc agtgaagagc    3840
ccaccgagtg ccggctacct ggtgatggtg tcgcgtggcg ccttggcaga tgagccaccc    3900
agcctggacc ctgtgcagag cttctcccag gaggcagtgg acacaggcag ggtcctgtac    3960
ctgcactccc gccctgaggc ctggagcgat gccttctcgc tggatgtggc ctcaggcctg    4020
ggtgctcccc tcgagggcgt ccttgtggag ctggaggtgc tgcccgctgc catcccacta    4080
gaggcgcaaa acttcagcgt ccctgagggt ggcagcctca ccctggcccc tccactgctc    4140
cgtgtctccg ggccctactt ccccactctc ctggcctca gcctgcaggt gctggagcca    4200
ccccagcatg gagccctgca gaaggaggac ggacctcaag ccaggaccct cagcgccttc    4260
tcctggagaa tggtggaaga gcagctgatc cgctacgtgc atgacgggag cgagacactg    4320
acagacagtt ttgtcctgat ggctaatgcc tccgagatgg atcgccagag ccatcctgtg    4380
gccttcactg tcactgtcct gcctgtcaat gaccaacccc ccatcctcac tacaaacaca    4440
ggcctgcaga tgtgggaggg ggccactgcg cccatccctg cggaggctct gaggagcacg    4500
gacggcgact ctgggtctga ggatctggtc tacaccatcg agcagccag caacgggcgg    4560 gtagtgctgc ggggggcgcc gggcactgag gtgcgcagct tcacgcaggc ccagctggac    4620
ggcgggctcg tgctgttctc acacagagga accctggatg gaggcttccg cttccgcctc    4680
tctgacggcg agcacacttc ccccggacac ttcttccgag tgacggccca gaagcaagtg    4740
ctcctctcgc tgaagggcag ccagacactg actgtctgcc cagggtccgt ccagccactc    4800
agcagtcaga ccctcagggc cagctccagc gcaggcactg accccagct cctgctctac    4860 cgtgtggtgc ggggcccca gctaggccgg ctgttccacg cccagcagga cagcacaggg    4920
gaggccctgg tgaacttcac tcaggcagag gtctacgctg gaatattct gtatgagcat    4980 gagatgcccc ccgagccctt tgggaggcc catgataccc tagagctcca gctgtcctcg    5040
ccgcctgccc gggacgtggc cgccaccctt gctgtggctg tgtcttttga ggctgcctgt    5100
ccccagcgcc ccagccacct ctggaagaac aaaggtctct gggtccccga gggcagcgg    5160 gccaggatca ccgtggctgc tctggatgcc tccaatctct tggccagcgt tccatcaccc    5220
cagcgctcag agcatgatgt gctcttccag gtcacacagt tccccagccg gggccagctg    5280
ttggtgtccg aggagcccct ccatgctggg cagccccact tcctgcagtc ccagctggct    5340
gcagggcagc tagtgtatgc ccacggcggt gggggcaccc agcaggatgg cttccacttt    5400
cgtgcccacc tccaggggcc agcaggggcc tccgtggctg accccaaaac ctcagaggcc    5460
tttgccatca cggtgaggga tgtaaatgag cggcccctc agccacaggc ctctgtccca    5520
ctccggctca cccgaggctc tcgtgcccc atctcccggg cccagctgag tgtggtggac    5580
ccagactcag ctcctgggga gattgagtac gaggtccagc gggcaccca caacggcttc    5640 ctcagcctgg tgggtggtgg cctggggccc gtgaccgct tcacgcaagc cgatgtggat    5700
tcagggcggc tggccttcgt ggccaacggg agcagcgtgg caggcatctt ccagctgagc    5760
atgtctgatg gggccagccc acccctgccc atgtccctgg ctgtggacat ctaccatcc    5820 gccatcgagg tgcagctgcg ggcacccctg gaggtgcccc aagctttggg gcgctcctca    5880
ctgagccagc agcagctccg ggtggttca gatcggagg agccagaggc agcataccgc    5940
ctcatccagg gaccccagta tgggcatctc ctggtgggcg ggcggcccac ctcggccttc    6000
```

-continued

```
agccaattcc agatagacca gggcgaggtg gtctttgcct tcaccaactt ctcctcctct   6060
catgaccact tcagagtcct ggcactggct aggggtgtca atgcatcagc cgtagtgaac   6120
gtcactgtga gggctctgct gcatgtgtgg gcaggtgggc catggcccca gggtgccacc   6180
ctgcgcctgg accccaccgt cctagatgct ggcgagctgg ccaaccgcac aggcagtgtg   6240
ccgcgcttcc gcctcctgga gggaccccgg catggccgcg tggtccgcgt gccccgagcc   6300
aggacggagc ccgggggcag ccagctggtg gagcagttca ctcagcagga ccttgaggac   6360
gggaggctgg ggctggaggt gggcaggcca gaggggaggg ccccggcccc gcaggtgac   6420 agtctcactc tggagctgtg ggcacagggc gtcccgcctg ctgtggcctc cctggacttt   6480
gccactgagc cttacaatgc tgcccggccc tacagcgtgg ccctgctcag tgtccccgag   6540
gccgcccgga cggaagcagg gaagccagag agcagcaccc ccacaggcga gccaggcccc   6600
atggcatcca gccctgagcc cgctgtggcc aagggaggct tcctgagctt ccttgaggcc   6660
aacatgttca gcgtcatcat ccccatgtgc ctggtacttc tgctcctggc gctcatcctg   6720
cccctgctct tctacctccg aaaacgcaac aagacgggca agcatgacgt ccaggtcctg   6780
actgccaagc cccgcaacgg cctggctggt gacaccgaga cctttcgcaa ggtggagcca   6840
ggccaggcca tcccgctcac agctgtgcct ggccagggc cccctccagg aggccagcct   6900
gacccagagc tgctgcagtt ctgccggaca cccaaccctg cccttaagaa tggccagtac   6960
tgggtgtgag gcctggcctg ggcccagatg ctgatcgggc cagggacagg c             7011
```

```
<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
ggcccgggcc ccctcctttg at                                              22

<210> SEQ ID NO 18
<211> LENGTH: 26
<212> TYPE: DNA
<213> ORGANISM: artificial
<220> FEATURE:
<223> OTHER INFORMATION: primer

<400> SEQUENCE: 18
ggtctagatc ataatttact tcatcc                                          26

<210> SEQ ID NO 19
<211> LENGTH: 22
<212> TYPE: DNA
<213> ORGANISM: artificial
<220> FEATURE:
<223> OTHER INFORMATION: Primer

<400> SEQUENCE: 19
ggctcgagca tggagataca cc                                              22

<210> SEQ ID NO 20
<211> LENGTH: 28
<212> TYPE: DNA
<213> ORGANISM: Artificial
<220> FEATURE:
<223> OTHER INFORMATION: Primer

<400> SEQUENCE: 20
```

```
ggggactagt ttatggtttc tgagaaca                                          28

<210> SEQ ID NO 21
<211> LENGTH: 585
<212> TYPE: DNA
<213> ORGANISM: Homo sapiens

<400> SEQUENCE: 21
ttcaatggcc agaggcgggg gctgcgggaa gctttgctga cgcgcaacat ggcagccggc        60
tgcaggctgg aggaggagga gtatgaggac gatgcctatg acattatga agctttctcc       120 accctggccc ctgaggcttg gccagccatg gagctgcctg agccatgcgt gcctgagcca       180 ggctgcctc ctgtctttgc caatttcacc cagctgctga ctatcagccc actggtggtg       240
gccgaggggg gcacagcctg gcttgagtgg aggcatgtgc agcccacgct ggacctgatg       300
gaggctgagc tgcgcaaatc ccaggtgctg ttcagcgtga cccgaggggc acgccatggc       360
gagctcgagc tggacatccc gggagcccag gcacgaaaaa tgttcaccct cctggacgtg       420
gtgaaccgca aggcccgctt catccacgat ggctctgagg acacctccga ccagctggtg       480
ctggaggtgt cggtgacggc tcgggtgccc atgccctcat gccttcggag gggccaaaca       540
tacctcctgc ccatccaggt caaccctgtc aatgacccac cccac                      585

<210> SEQ ID NO 22
<211> LENGTH: 1290
<212> TYPE: DNA
<213> ORGANISM: Homo sapiens

<400> SEQUENCE: 22
gtccgcgtca ctggggccct gcagtttggg gagctgcaga aacacggggc aggtgggtg         60 gagggtgctg agtggtgggc cacacaggcg ttccaccagc gggatgtgga gcagggccgc       120
gtgaggtacc tgagcactga cccacagcac cacgcttacg acaccgtgga aacctggcc        180 ctggaggtgc aggtgggcca ggagatcctg agcaatctgt ccttcccagt gaccatccag       240
agagccactg tgtggatgct gcggctggag ccactgcaca ctcagaacac ccagcaggag       300
accctcacca cagcccacct ggaggccacc ctggaggagg caggcccaag ccccccaacc       360
ttccattatg aggtggttca ggctcccagg aaaggcaacc ttcaactaca gggcacaagg       420
ctgtcagatg gccagggctt cacccaggat gacatacagg ctggccgggt gacctatggg       480
gccacagcac gtgcctcaga ggcagtcgag gacaccttcc gtttccgtgt cacagctcca       540
ccatatttct ccccactcta taccttcccc atccacattg gtggtgaccc agatgcgcct       600
gtcctcacca atgtcctcct cgtggtgcct gagggtggtg agggtgtcct ctctgctgac       660
cacctctttg tcaagagtct caacagtgcc agctacctct atgaggtcat ggagcggccc       720
cgccatggga ggttggcttg gcgtgggaca caggacaaga ccactatggt gacatccttc       780
accaatgaag acctgttgcg tggccggctg gtctaccagc atgatgactc cgagaccaca       840
gaagatgata tcccatttgt tgctacccgc cagggcgaga gcagtggtga catggcctgg       900
gaggaggtac ggggtgtctt ccgagtggcc atccagcccg tgaatgacca cgcccctgtg       960
cagaccatca gccggatctt ccatgtggcc cggggtgggc ggcggctgct gactacagac      1020
gacgtggcct tcagcgatgc tgactcgggc tttgctgacg cccagctggt gcttaccgc       1080 aaggacctcc tctttggcag tatcgtggcc gtagatgagc ccacgcggcc catctaccgc      1140
ttcacccagg aggacctcag gaagaggcga gtactgttcg tgcactcagg ggctgaccgt      1200
ggctggatcc agctgcaggt gtccgacggg caacaccagg ccactgcgct gctggaggtg      1260
```

```
caggcctcgg aaccctacct ccgtgtggcc                                        1290

<210> SEQ ID NO 23
<211> LENGTH: 294
<212> TYPE: DNA
<213> ORGANISM: Homo sapiens

<400> SEQUENCE: 23
gccactgagc cttacaatgc tgcccggccc tacagcgtgg ccctgctcag tgtccccgag         60
gccgcccgga cggaagcagg gaagccagag agcagcaccc ccacaggcga gccaggcccc        120
atggcatcca gccctgagcc cgctgtggcc aagggaggct tcctgagctt ccttgaggcc        180
aacatgttca gcgtcatcat ccccatgtgc ctggtacttc tgctcctggc gctcatcctg        240
cccctgctct tctacctccg aaaacgcaac aagacgggca agcatgacgt ccag              294

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
tcctcgaggt caatggccag aggcggggg                                           29

<210> SEQ ID NO 25
<211> LENGTH: 54
<212> TYPE: DNA
<213> ORGANISM: Artificial
<220> FEATURE:
<223> OTHER INFORMATION: primer

<400> SEQUENCE: 25
cccgggttac tacttatcgt cgtcatcctt gtaatcgtgg ggtgggtcat tgac               54

<210> SEQ ID NO 26
<211> LENGTH: 29
<212> TYPE: DNA
<213> ORGANISM: Artificial
<220> FEATURE:
<223> OTHER INFORMATION: primer

<400> SEQUENCE: 26
gcctcgagtt ccgcgtcact ggggccctg                                           29

<210> SEQ ID NO 27
<211> LENGTH: 57
<212> TYPE: DNA
<213> ORGANISM: Artificial
<220> FEATURE:
<223> OTHER INFORMATION: primer

<400> SEQUENCE: 27
actagtttac tacttatcgt cgtcatcctt gtaatcggcc acacggaggt agggttc            57

<210> SEQ ID NO 28
<211> LENGTH: 32
<212> TYPE: DNA
<213> ORGANISM: artificial
<220> FEATURE:
<223> OTHER INFORMATION: primer

<400> SEQUENCE: 28
tgctcgaggc cactgagcct tacaatgctg cc                                       32
```

<210> SEQ ID NO 29
<211> LENGTH: 56
<212> TYPE: DNA
<213> ORGANISM: Artificial
<220> FEATURE:
<223> OTHER INFORMATION: primer

<400> SEQUENCE: 29
cccgggttac tacttatcgt cgtcatcctt gtaatcctgg acgtcatgct tgcccg        56

<210> SEQ ID NO 30
<211> LENGTH: 22
<212> TYPE: DNA
<213> ORGANISM: Artificial
<220> FEATURE:
<223> OTHER INFORMATION: primer

<400> SEQUENCE: 30
ggcccgggcc ccctcctttg at        22

<210> SEQ ID NO 31
<211> LENGTH: 26
<212> TYPE: DNA
<213> ORGANISM: Artificial
<220> FEATURE:
<223> OTHER INFORMATION: primer

<400> SEQUENCE: 31
ggtctagatc ataatttact tcatcc        26

<210> SEQ ID NO 32
<211> LENGTH: 26
<212> TYPE: DNA
<213> ORGANISM: Artificial
<220> FEATURE:
<223> OTHER INFORMATION: primer

<400> SEQUENCE: 32
ggtctagaga attccagcaa aagcag        26

<210> SEQ ID NO 33
<211> LENGTH: 27
<212> TYPE: DNA
<213> ORGANISM: Artificial
<220> FEATURE:
<223> OTHER INFORMATION: primer

<400> SEQUENCE: 33
gggtcgacaa gggtattttt ctttaat        27

<210> SEQ ID NO 34
<211> LENGTH: 31
<212> TYPE: DNA
<213> ORGANISM: Artificial
<220> FEATURE:
<223> OTHER INFORMATION: primer

<400> SEQUENCE: 34
ggggtctaga cctcctttga ttagtatatt c        31

<210> SEQ ID NO 35
<211> LENGTH: 45
<212> TYPE: DNA
<213> ORGANISM: Artificial
<220> FEATURE:
<223> OTHER INFORMATION: primer

```
<400> SEQUENCE: 35
atcttcgcta tctgtcgccg cggcgcgtgc ttcagtttgt tgcgc          45

<210> SEQ ID NO 36
<211> LENGTH: 45
<212> TYPE: DNA
<213> ORGANISM: Artificial
<220> FEATURE:
<223> OTHER INFORMATION: primer

<400> SEQUENCE: 36
gcgcaacaaa ctgaagcagc ggccgcggcg acagatagcg aagat          45

<210> SEQ ID NO 37
<211> LENGTH: 42
<212> TYPE: DNA
<213> ORGANISM: Artificial
<220> FEATURE:
<223> OTHER INFORMATION: primer

<400> SEQUENCE: 37
tgtaggtgta tctccatgct cgagagctag gcgatcaatt tc             42

<210> SEQ ID NO 38
<211> LENGTH: 42
<212> TYPE: DNA
<213> ORGANISM: Artificial
<220> FEATURE:
<223> OTHER INFORMATION: primer

<400> SEQUENCE: 38
ggaattgatc gcctagctct cgagcatgga gatacaccta ca             42

<210> SEQ ID NO 39
<211> LENGTH: 42
<212> TYPE: DNA
<213> ORGANISM: Artificial
<220> FEATURE:
<223> OTHER INFORMATION: primer

<400> SEQUENCE: 39
aaacggattt atttagatcc cgggttatgg tttctgagaa ca             42

<210> SEQ ID NO 40
<211> LENGTH: 42
<212> TYPE: DNA
<213> ORGANISM: Artificial
<220> FEATURE:
<223> OTHER INFORMATION: primer

<400> SEQUENCE: 40
tgttctcaga aaccataacc cgggatctaa ataaatccgt tt             42

<210> SEQ ID NO 41
<211> LENGTH: 28
<212> TYPE: DNA
<213> ORGANISM: Artificial
<220> FEATURE:
<223> OTHER INFORMATION: primer

<400> SEQUENCE: 41
gggggtcgac cagctcttct tggtgaag                             28

<210> SEQ ID NO 42
<211> LENGTH: 9
```

```
<212> TYPE: PRT
<213> ORGANISM: Human papilloma virus

<400> SEQUENCE: 42

Arg Ala His Tyr Asn Ile Val Thr Phe
1               5

<210> SEQ ID NO 43
<211> LENGTH: 9
<212> TYPE: PRT
<213> ORGANISM: Homo sapiens

<400> SEQUENCE: 43

Ile Leu Ser Asn Leu Ser Phe Pro Val
1               5

<210> SEQ ID NO 44
<211> LENGTH: 9
<212> TYPE: PRT
<213> ORGANISM: Homo sapiens

<400> SEQUENCE: 44

Leu Leu Phe Gly Ser Ile Val Ala Val
1               5

<210> SEQ ID NO 45
<211> LENGTH: 9
<212> TYPE: PRT
<213> ORGANISM: Homo sapiens

<400> SEQUENCE: 45

Leu Ile Leu Pro Leu Leu Phe Tyr Leu
1               5

<210> SEQ ID NO 46
<211> LENGTH: 28
<212> TYPE: PRT
<213> ORGANISM: Listeria monocytogenes

<400> SEQUENCE: 46

Lys Glu Ser Val Val Asp Ala Ser Glu Ser Asp Leu Asp Ser Ser Met
1               5                   10                  15

Gln Ser Ala Asp Glu Ser Thr Pro Gln Pro Leu Lys
            20                  25

<210> SEQ ID NO 47
<211> LENGTH: 20
<212> TYPE: PRT
<213> ORGANISM: Listeria monocytogenes

<400> SEQUENCE: 47

Lys Ser Glu Glu Val Asn Ala Ser Asp Phe Pro Pro Pro Pro Thr Asp
1               5                   10                  15

Glu Glu Leu Arg
            20
```

```
<210> SEQ ID NO 48
<211> LENGTH: 33
<212> TYPE: PRT
<213> ORGANISM: Listeria monocytogenes

<400> SEQUENCE: 48

Arg Gly Gly Arg Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg
```